United States Patent
Cameron et al.

(10) Patent No.: US 6,531,485 B2
(45) Date of Patent: *Mar. 11, 2003

(54) PROSTAGLANDIN AGONISTS

(75) Inventors: Kimberly O. Cameron, East Lyme, CT (US); Paul A. DaSilva-Jardine, Providence, RI (US)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 51 days.

(21) Appl. No.: 09/446,099

(22) PCT Filed: Jun. 4, 1998

(86) PCT No.: PCT/IB98/00866

§ 371 (c)(1),
(2), (4) Date: Dec. 16, 1999

(87) PCT Pub. No.: WO98/58911

PCT Pub. Date: Dec. 30, 1998

(65) Prior Publication Data

US 2003/0008895 A1 Jan. 9, 2003

Related U.S. Application Data

(60) Provisional application No. 60/050,575, filed on Jun. 23, 1997.

(51) Int. Cl.[7] .................. A61K 31/5575; A61K 31/559; C07C 405/00; C07C 61/16; C07C 69/74; A61P 19/10

(52) U.S. Cl. .................. 514/307; 514/340; 514/354; 514/356; 514/381; 514/364; 514/365; 514/464; 514/419; 514/415; 514/456; 514/439; 514/530; 514/570; 546/147; 546/268.4; 546/269.1; 546/269.4; 548/494; 548/204; 548/252; 548/253; 548/131; 548/132; 549/447; 549/79; 549/399; 562/503; 562/504; 560/121; 560/118

(58) Field of Search .................. 562/503, 504; 560/121, 118; 549/447, 79, 399; 548/494, 204, 252, 253, 131, 132; 546/147, 268.4, 269.1, 269.4; 514/570, 530, 419, 415, 365, 456, 439, 307, 340, 354, 356, 381, 364, 464

(56) References Cited

U.S. PATENT DOCUMENTS

| | | | |
|---|---|---|---|
| 3,888,905 A | 6/1975 | Miyano | 260/471 |
| 3,932,389 A | 1/1976 | Johnson et al. | 260/240 |
| 3,980,700 A | 9/1976 | Miyano | 260/520 |
| 4,097,601 A | 6/1978 | Schaaf | 424/269 |
| 4,197,407 A | 4/1980 | Wissner et al. | 560/118 |

FOREIGN PATENT DOCUMENTS

| | | | |
|---|---|---|---|
| DE | 2434133 | * | 1/1976 |
| DK | 2548955 | | 10/1975 |
| GB | 1521688 | | 11/1974 |
| WO | WO9731640 | | 9/1997 |

OTHER PUBLICATIONS

King FD. Medicinal Chemistry: Principles and Practice. Pub;osjed by The Royal Society of Chemistry. pp. 206–209, 1994.*

* cited by examiner

*Primary Examiner*—Evelyn Mei Huang
(74) *Attorney, Agent, or Firm*—Peter C. Richardson; Gregg C. Benson; Todd M. Crissey

(57) ABSTRACT

This invention relates to prostaglandin agonists, methods of using such prostaglandin agonists, pharmaceutical compositions containing such prostaglandin agonists and kits containing such prostaglandin agonists. The prostaglandin agonists are useful for the treatment of bone disorders including osteoporosis.

7 Claims, No Drawings

PROSTAGLANDIN AGONISTS

This application is the national stage of copending International Patent Application Number PCT/IB98/00866, filed Jun. 4, 1998, which is a continuation of U.S. Provisional Application No. 60/050,575, filed Jun. 23, 1997.

BACKGROUND OF INVENTION

This invention relates to prostaglandin agonists, pharmaceutical compositions containing such agonists and the use of such agonists to prevent bone loss or restore or augment bone mass including the treatment of conditions which present with low bone mass in mammals, including humans.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

There are currently two main types of pharmaceutical therapy for the treatment of osteoporosis. The first is the use of anti-resorptive compounds to reduce the resorption of bone tissue.

Estrogen is an example of an anti-resorptive agent. It is known that estrogen reduces fractures. In addition, Black, et al. in EP 0605193A1 report that estrogen, particularly when taken orally, lowers plasma levels of LDL and raises those of the beneficial high density lipoproteins (HDL's). However, estrogen failed to restore bone back to young adult levels in the established osteoporotic skeleton. Furthermore, long-term estrogen therapy, however, has been implicated in a variety of disorders, including an increase in the risk of uterine cancer, endometrial cancer and possibly breast cancer, causing many women to avoid this treatment. The significant undesirable effects associated with estrogen therapy support the need to develop alternative therapies for osteoporosis that have the desirable effect on serum LDL but do not cause undesirable effects.

A second type of pharmaceutical therapy for the treatment of osteoporosis is the use of anabolic agents to promote bone formation and increase bone mass. This class of agents is expected to restore bone to the established osteoporotic skeleton.

U.S. Pat. No. 3,932,389, incorporated herein by reference, discloses certain tetrazolyl prostaglandin derivatives as vasodilators, bronchodilators, antiulcer and antisecretory agents.

U.S. Pat. No. 4,097,601, incorporated herein by reference, discloses selected compounds from U.S. Pat. No. 3,932,389 as having utility in the treatment of bone disorders.

British patent number GB 1 521 688 discloses certain cyclopentanones for the production of hypotension, bronchodilation, inhibition of gastric acid secretion, healing of gastric ulcers, luteolysis and the stimulation of uterine contraction.

U.S. Pat. No. 3,980,700, incorporated herein by reference, discloses certain cyclopentanones as antibacterial agents.

U.S. Pat. No. 4,197,407, incorporated herein by reference, discloses certain cyclopentanones as smooth muscle stimulants, arterial blood pressure lowering agents and antagonists of epinephrine-induced mobilization of free fatty acid.

In addition to osteoporosis, approximately 20–25 million women and an increasing number of men have detectable vertebral fractures as a consequence of reduced bone mass, with an additional 250,000 hip fractures reported yearly in America alone. The latter case is associated with a 12% mortality rate within the first two years and with a 30% rate of patients requiring nursing home care after the fracture. While this is already significant, the economic and medical consequences of convalescence due to slow or imperfect healing of these bone fractures is expected to increase, due to the aging of the general population. While there are several promising therapies (bis-phosphonates, etc.) in development to prevent bone loss with age and thus reduce the probability of incurring debilitating fractures, these therapies are not indicated for restoration of bone mass once the fracture has occurred.

Estrogens have been shown (Bolander et al., 38th Annual Meeting Orthopedic Research Society, 1992) to improve the quality of the healing of appendicular fractures. Therefore, estrogen replacement therapy might appear to be a method for the treatment of fracture repair. However, patient compliance with estrogen therapy is relatively poor due to its side effects, including the resumption of menses, mastodynia, an increased risk of uterine cancer, an increased perceived risk of breast cancer, and the concomitant use of progestins. In addition, men are likely to object to the use of estrogen treatment. Clearly the need exists for a therapy which would be beneficial to patients who have suffered debilitating bone fractures and which would increase patient compliance.

Although there are a variety of osteoporosis therapies there is a continuing need and a continuing search in this field of art for alternative osteoporosis therapies. In addition, there is a need for bone fracture healing therapies.

SUMMARY OF THE INVENTION

This invention is directed to compounds of Formula I

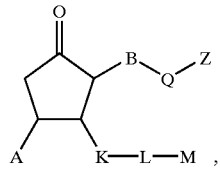

Formula I prodrugs thereof and pharmaceutically acceptable salts of said compounds and prodrugs wherein A is hydrogen or hydroxy;
B is propylene, propenylene or propynylene;
Q is propylene, —$CH_2OCH_2$—, thiazolyl, pyridyl, phenyl or thienyl;
Z is carboxyl, ($C_1$–$C_6$)alkoxycarbonyl, tetrazolyl, 1,2,4-oxadiazolyl or 5-oxo-1,2,4-oxadiazolyl;

K is ethylene or ethenylene;
L is a bond or —CO—;
M is —Ar, —Ar$^1$—V—Ar$^2$, —Ar$^1$—S—Ar$^2$ or —Ar$^1$—O—Ar$^2$ wherein
  Ar and Ar$^1$ are either (1) each independently a fully unsaturated five to eight membered ring optionally having one to four heteroatoms selected independently from oxygen, sulfur and nitrogen, or a bicyclic ring consisting of two fused partially saturated, fully saturated or fully unsaturated five and/or six membered rings, taken independently, optionally having one to four heteroatoms selected independently from nitrogen, sulfur and oxygen, or a tricyclic ring consisting of three fused partially saturated, fully saturated or fully unsaturated five and/or six membered rings, taken independently, optionally having one to four heteroatoms selected independently from nitrogen, sulfur and oxygen, any of said partially saturated or fully saturated rings optionally having one or more oxo groups substituted on carbon, or
  (2) each independently a fully saturated five to eight membered ring;
  Ar$^2$ is a partially saturated, fully saturated or fully unsaturated five to eight membered ring optionally having one to four heteroatoms selected independently from oxygen, sulfur and nitrogen, or a bicyclic ring consisting of two fused partially saturated, fully saturated or fully unsaturated five and/or six membered rings, taken independently, optionally having one to four heteroatoms selected independently from nitrogen, sulfur and oxygen, or a tricyclic ring consisting of three fused partially saturated, fully saturated or fully unsaturated five and/or six membered rings, taken independently, optionally having one to four heteroatoms selected independently from nitrogen, sulfur and oxygen, any of said partially saturated or fully saturated rings optionally having one or more oxo groups substituted on carbon;
  said Ar and Ar$^1$ moieties, when a fully unsaturated five to eight membered ring, a bicyclic ring or a tricyclic ring, and said Ar$^2$ moieties are each independently optionally substituted on carbon, on one ring if the moiety is monocyclic, on one or both rings if the moiety is bicyclic, or on one, two or three rings if the moiety is tricyclic, with up to three substituents selected from R$^1$, R$^2$ and R$^3$ wherein R$^1$, R$^2$ and R$^3$ are independently hydroxy, nitro, halo, (C$_1$–C$_7$) alkoxy, (C$_1$–C$_4$)alkoxy(C$_1$–C$_4$)alkyl, (C$_1$–C$_4$) alkoxycarbonyl, (C$_1$–C$_7$)alkyl, (C$_2$–C$_7$)alkenyl, (C$_2$–C$_7$)alkynyl, (C$_3$–C$_7$)cycloalkyl, (C$_3$–C$_7$)cycloalkyl(C$_1$–C$_4$)alkyl, (C$_3$–C$_7$)cycloalkyl(C$_1$–C$_4$) alkanoyl, formyl, (C$_1$–C$_8$)alkanoyl, (C$_1$–C$_6$)alkanoyl (C$_1$–C$_6$)alkyl, aminocarbonylamino or mono-N-, di-N,N-, di-N,N'- or tri-N,N,N'-(C$_1$–C$_4$)alkyl substituted aminocarbonylamino, (C$_1$–C$_4$)alkanoylamino, (C$_1$–C$_4$)alkoxycarbonylamino, sulfonamido, hydroxysulfonyl, (C$_1$–C$_4$)alkylsulfonamido, amino, mono-N- or di-N,N—(C$_1$–C$_4$)alkylamino, carbamoyl, mono-N- or di-N,N—(C$_1$–C$_4$) alkylcarbamoyl, cyano, thiol, (C$_1$–C$_6$)alkylthio, (C$_1$–C$_6$)alkylsulfinyl, (C$_1$–C$_4$)alkylsulfonyl or mono-N- or di-N,N—(C$_1$–C$_4$)alkylaminosulfinyl;
  R$^1$, R$^2$ and R$^3$, when containing an alkyl, alkenyl, alkylene or alkenylene moiety, are optionally straight or branched and are optionally mono-, di- or tri-substituted on carbon independently with halo or hydroxy; and
  V is a bond, —CO— or (C$_1$–C$_3$)alkylene optionally mono- or di-substituted independently with hydroxy or fluoro,
provided that (1) when L is —CO—, A is hydroxyl; (2) when L is a bond and M is phenyl, said phenyl is substituted with one to three substitutes selected from R$^1$, R$^2$ and R$^3$; and (3) when M is monosubstituted phenyl, M is not methylphenyl.

A preferred group of compounds, designated the A Group, contains those compounds having the Formula I as shown above, and pharmaceutically acceptable salts thereof, wherein L is absent, B and Q are each n-propylene and Z is carboxy, (C$_1$–C$_3$)alkoxycarbonyl or tetrazolyl.

A group of compounds which is preferred within the A Group, designated the B Group, contains those compounds, and pharmaceutically acceptable salts thereof, wherein A is OH.

A group of compounds which is preferred within the B Group, designated the C Group, contains those compounds, and pharmaceutically acceptable salts thereof, wherein M is thiazolyl or pyridyl optionally substituted with up to three substituents independently selected from R$^1$, R$^2$ and R$^3$; or M is phenyl substituted with one to three substituents independently selected from R$^1$, R$^2$ and R$^3$.

A group of compounds which is preferred within the C Group, designated the D Group, contains those compounds, and pharmaceutically acceptable salts thereof, wherein K is ethenylene.

A group of compounds which is preferred within the D group, designated the E Group, contains those compounds, and pharmaceutically acceptable salts thereof, wherein M is phenyl substituted with one to three groups selected from R$^1$, R$^2$ and R$^3$, wherein R$^1$, R$^2$ and R$^3$ are independently selected from (C$_1$–C$_7$) alkoxy, hydroxy, trifluoromethyl, trifluoromethoxy, halo and (C$_1$–C$_6$) alkyl.

A group of compounds which is preferred within the E group designated the F Group, contains those compounds, and pharmaceutically acceptable salts thereof, wherein R$^1$, R$^2$ and R$^3$ are independently chloro and Z is carboxy, ethoxycarbonyl or tetrazolyl.

Especially preferred compounds within the F Group are those compounds, and pharmaceutically acceptable salts thereof, wherein said phenyl group is substituted with 3-chloro or 3,5-dichloro.

Another group of preferred compounds within the A Group, designated the G Group, contains those compounds, and pharmaceutically acceptable salts thereof, wherein A is H.

A group of compounds which is preferred within the G Group, designated the H Group, contains those compounds, and pharmaceutically acceptable salts thereof, wherein M is thiazolyl or pyridyl optionally substituted with up to three substituents independently selected from R$^1$, R$^2$ and R$^3$; or M is phenyl substituted with one to three substituents independently selected from R$^1$, R$^2$ and R$^3$.

A group of compounds which is preferred within the H Group, designated the J Group, contains those compounds, and pharmaceutically acceptable salts thereof, wherein K is ethenylene.

A group of compounds which is preferred within the J Group, designated the K Group, contains those compounds, and pharmaceutically acceptable salts thereof, wherein M is phenyl substituted with one to three groups selected from R$^1$, R$^2$ and R$^3$, wherein R$^1$, R$^2$ and R$^3$ are independently selected from (C$_1$–C$_7$) alkoxy, hydroxy, trifluoromethyl, trifluoromethoxy, halo and (C$_1$–C$_6$) alkyl.

A group of compounds which is preferred within the K Group, designated the L Group, contains those compounds, and pharmaceutically acceptable salts thereof, wherein $R^1$, $R^2$ and $R^3$ are independently chloro, fluoro or trifluoromethyl and Z is carboxy, ethoxycarbonyl or tetrazolyl.

Especially preferred compounds within the K Group are trans-7-(2-(2-(3,5-bis-trifluoromethyl-phenyl)-vinyl)-5-oxo-cyclopentyl)-heptanoic acid; trans-7-(2-(2-(4-chloro-3-trifluoromethyl-phenyl)-vinyl)-5-oxo-cyclopentyl)-heptanoic acid; trans-7-(2-(2-(3,5-dichlorophenyl)-vinyl)-5-oxo-cyclopentyl)-heptanoic acid; trans-7-(2-(2-(3-chlorophenyl)-vinyl)-5-oxo-cyclopentyl)-heptanoic acid; trans-7-(2-oxo-5-(2-(3-trifluoromethyl-phenyl)-vinyl)-cyclopentyl)-heptanoic acid; and trans-7-(2-(2-(4-fluoro-phenyl)-vinyl)-5-oxo-cyclopentyl)-heptanoic acid; and pharmaceutically acceptable salts thereof.

Another group of compounds which is preferred within the L Group, designated the M Group, contains those compounds, and pharmaceutically acceptable salts thereof, wherein Z is carboxy.

An especially preferred compound within the M Group is the compound wherein M is 3,5-bis-trifluoromethylphenyl.

Another especially preferred compound within the M Group is the compound wherein M is 4-chloro-3-trifluoromethylphenyl.

Another especially preferred compound within the M Group is the compound wherein M is 3,5-dichlorophenyl.

Another especially preferred compound within the M Group is the compound wherein M is 3-chlorophenyl.

Another especially preferred compound within the M Group is the compound wherein M is 3-trifluoromethylphenyl.

Another especially preferred compound within the M Group is the compound wherein M is 4-fluorophenyl.

Other especially preferred compounds within the K Group are ethyl trans-7-(2-(2-(3,5-bis-trifluoromethyl-phenyl)-vinyl)-5-oxo-cyclopentyl)-heptanoate; ethyl trans-7-(2-(2-(4-chloro-3-trifluoromethyl-phenyl)-vinyl)-5-oxo-cyclopentyl)-heptanoate; ethyl trans-7-(2-(2-(3,5-dichlorophenyl)-vinyl)-5-oxo-cyclopentyl)-heptanoate; ethyl trans-7-(2-(2-(3-chlorophenyl)-vinyl)-5-oxo-cyclopentyl)-heptanoate; ethyl trans-7-(2-oxo-5-(2-(3-trifluoromethyl-phenyl)-vinyl)-cyclopentyl)-heptanoate; and ethyl trans-7-(2-(2-(4-fluoro-phenyl)-vinyl)-5-oxo-cyclopentyl)-heptanoate; and pharmaceutically acceptable salts thereof.

Another group of compounds which is preferred within the L Group, designated the N Group, contains those compounds, and pharmaceutically acceptable salts thereof, wherein Z is ethoxycarbonyl.

An especially preferred compound within the N Group is the compound wherein M is 3,5-bis-trifluoromethylphenyl.

Another especially preferred compound within the N Group is the compound wherein M is 4-chloro-3-trifluoromethylphenyl.

Another especially preferred compound within the N Group is the compound wherein M is 3,5-dichlorophenyl.

Another especially preferred compound within the N Group is the compound wherein M is 3-chlorophenyl.

Another especially preferred compound within the N Group is the compound wherein M is 3-trifluoromethylphenyl.

Another especially preferred compound within the N Group is the compound wherein M is 4-fluorophenyl.

Other especially preferred compounds within the K Group are trans-3-(2-(3,5-bis-trifluoromethyl-phenyl)-vinyl)-2-(6-(2-H-tetrazol-5-yl)-hexyl)-cyclopentanone; trans-3-(2-(4-chloro-3-trifluoromethylphenyl)-vinyl)-2-(6-(2H-tetrazol-5-yl)-cyclopentanone; trans-3-(2-(3,5-dichloro-phenyl)-vinyl)-2-(6-(2H-tetrazol-5-yl)-hexyl)-cyclopentanone; trans-3-(2-(3-chloro-phenyl)-vinyl)-2-(6-(2H-tetrazol-5-yl)-hexyl)-cyclopentanone; trans-3-(2-(3-trifluoromethyl-phenyl)-vinyl)-2-(6-(2H-tetrazol-5-yl)-hexyl)-cyclopentanone; and trans-3-(2-(4-fluoro-phenyl)-vinyl)-2-(6-(2H-tetrazol-5-yl)-hexyl)-cyclopentanone; and pharmaceutically acceptable salts thereof.

Another group of compounds which is preferred within the L Group, designated the P Group, contains those compounds wherein Z is tetrazolyl.

An especially preferred compound within the P Group is the compound wherein M is 3,5-bis-trifluoromethylphenyl.

Another especially preferred compound within the P Group is the compound wherein M is 4-chloro-3-trifluoromethylphenyl.

Another especially preferred compound within the P Group is the compound wherein M is 3,5-dichlorophenyl.

Another especially preferred compound within the P Group is the compound wherein M is 5-chlorophenyl.

Another especially preferred compound within the P Group is the compound wherein M is 3-trifluoromethylphenyl.

Another especially preferred compound within the P Group is the compound wherein M is 4-fluorophenyl.

Another preferred group of compounds of Formula I, designated the Q Group, contains those compounds, and pharmaceutically acceptable salts thereof, having the Formula I as shown above wherein L is —CO—, B and Q are each n-propylene and Z is carboxy, $(C_1-C_3)$alkoxycarbonyl or tetrazolyl.

A group of compounds which is preferred within the Q Group, designated the S Group, contains those compounds, and pharmaceutically acceptable salts thereof, wherein A is OH.

A group of compounds which is preferred within the S Group, designated the T Group, contains those compounds, and pharmaceutically acceptable salts thereof, wherein M is thiazolyl or pyridyl optionally substituted with up to three substituents independently selected from $R^1$, $R^2$ and $R^3$; or M is phenyl substituted with one to three substituents independently selected from $R^1$, $R^2$ and $R^3$.

A group of compounds which is preferred within the T Group, designated the U Group, contains those compounds, and pharmaceutically acceptable salts thereof, wherein K is ethenylene.

A group of compounds which is preferred within the U Group, designated the V Group, contains those compounds, and pharmaceutically acceptable salts thereof, wherein M is phenyl substituted with one to three groups selected from $R^1$, $R^2$ and $R^3$, wherein $R^1$, $R^2$ and $R^3$ are independently selected from $(C_1-C_7)$ alkoxy, hydroxy, trifluoromethyl, trifluoromethoxy, halo and $(C_1-C_6)$ alkyl.

A group of compounds which is preferred within the V Group, designated the X Group, contains those compounds, and pharmaceutically acceptable salts thereof, wherein $R^1$, $R^2$ and $R^3$ are independently chloro and Z is carboxy, ethoxycarbonyl or tetrazolyl.

Especially preferred compounds within the X Group are those compounds, and pharmaceutically acceptable salts thereof, wherein said phenyl group is substituted with 3-chloro or 3,5-dichloro.

This invention is also directed to methods for augmenting and maintaining bone mass and preventing further bone loss in vertebrate, e.g., a mammal, comprising administering to a mammal a therapeutically effective amount of a compound of Formula I$^A$

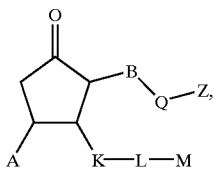

prodrugs thereof or pharmaceutically acceptable salts of said compounds or said prodrugs wherein A is hydrogen or hydroxy;

B is propylene, propenylene or propynylene;

Q is propylene, —CH$_2$OCH$_2$—, thiazolyl, pyridyl, phenyl or thienyl;

Z is carboxyl, (C$_1$–C$_6$)alkoxycarbonyl, tetrazolyl, 1,2,4-oxadiazolyl or 5-oxo-1,2,4-oxadiazolyl;

K is ethylene or ethenylene;

L is a bond or —CO—;

M is —Ar, —Ar$^1$—V—Ar$^2$, —Ar$^1$—S—Ar$^2$ or —Ar$^1$—O—Ar$^2$ wherein

Ar, Ar$^1$ and Ar$^2$ are each independently a fully saturated, partially unsaturated or fully unsaturated five to eight membered ring optionally having one to four heteroatoms selected independently from oxygen, sulfur and nitrogen, or, a bicyclic ring consisting of two fused partially saturated, fully saturated or fully unsaturated five and/or six membered rings, taken independently, optionally having one to four heteroatoms selected independently from nitrogen, sulfur and oxygen, or, a tricyclic ring consisting of three fused partially saturated, fully saturated or fully unsaturated five and/or six membered rings, taken independently, optionally having one to four heteroatoms selected independently from nitrogen, sulfur and oxygen, any of said partially saturated or fully saturated rings optionally having one or more oxo groups substituted on carbon, said Ar, Ar$^1$ and Ar$^2$ moieties are each independently optionally substituted on carbon, on one ring if the moiety is monocyclic, on one or both rings if the moiety is bicyclic, or on one, two or three rings is the moiety is tricyclic, with up to three substituents independently selected from R$^1$, R$^2$ and R$^3$ wherein R$^1$, R$^2$ and R$^3$ are hydroxy, nitro, halo, (C$_1$–C$_7$)alkoxy, (C$_1$–C$_4$)alkoxy(C$_1$–C$_4$)alkyl, (C$_1$–C$_4$)alkoxycarbonyl, (C$_1$–C$_7$)alkyl, (C$_2$–C$_7$)alkenyl, (C$_2$–C$_7$)alkynyl, (C$_3$–C$_7$)cycloalkyl, (C$_3$–C$_7$)cycloalkyl(C$_1$–C$_4$)alkyl, (C$_3$–C$_7$)cycloalkyl(C$_1$–C$_4$)alkanoyl, formyl, (C$_1$–C$_8$)alkanoyl, (C$_1$–C$_6$)alkanoyl(C$_1$–C$_6$)alkyl, aminocarbonylamino or mono-N-, di-N,N-, di-N,N'- or tri-N,N,N'—(C$_1$–C$_4$)alkyl substituted aminocarbonylamino, (C$_1$–C$_4$)alkanoylamino, (C$_1$–C$_4$)alkoxycarbonylamino, sulfonamido, hydroxysulfonyl, (C$_1$–C$_4$)alkylsulfonamido, amino, mono-N- or di-N,N—(C$_1$–C$_4$)alkylamino, carbamoyl, mono-N- or di-N,N—(C$_1$–C$_4$)alkylcarbamoyl, cyano, thiol, (C$_1$–C$_5$)alkylthio, (C$_1$–C$_6$)alkylsulfinyl, (C$_1$–C$_4$)alkylsulfonyl or mono-N- or di-N,N—(C$_1$–C$_4$)alkylaminosulfinyl;

R$^1$, R$^2$ and R$^3$, when containing an alkyl, alkenyl, alkylene or alkenylene moiety, are optionally straight or branched and are optionally mono-, di- or tri-substituted on carbon independently with halo or hydroxy; and V is a bond, —CO— or (C$_1$–C$_3$)alkylene optionally mono- or di-substituted independently with hydroxy or fluoro.

This invention also directed to methods for treating vertebrates, e.g., a mammal, having a condition which presents with low bone mass comprising administering to vertebrate, e.g., a mammal, having a condition which presents with low bone mass a therapeutically effective amount of a compound of Formula I$^A$ above or a pharmaceutically acceptable salt or prodrug thereof. Preferably postmenopausal women and men over the age of 60 are treated. Also included are individuals regardless of age who have significantly reduced bone mass, i.e., greater than or equal to 1.5 standard deviations below young normal levels.

Yet another aspect of this invention is directed to methods for treating osteoporosis, bone fractures, osteotomy, bone loss associated with periodontitis, or prosthetic ingrowth in vertebrate, e.g., a mammal (including a human being), comprising administering to vertebrate, e.g., a mammal suffering from osteoporosis, bone fracture, osteotomy, bone loss associated with periodontitis, or prosthetic ingrowth an osteoporosis, bone fracture, osteotomy, bone loss associated with periodontitis, or prosthetic ingrowth treating amount of a Formula I$^A$ compound or a pharmaceutically acceptable salt or prodrug thereof.

Yet another aspect of this invention is directed to methods for treating osteoporosis in vertebrate, e.g., a mammal (including a human being), by comprising administering to vertebrate, e.g., a mammal suffering from osteoporosis an osteoporosis treating amount of a Formula I$^A$ compound or a pharmaceutically acceptable salt or prodrug thereof.

Yet another aspect of this invention is directed to method for treating osteotomy bone loss in vertebrate, e.g., a mammal (including a human being), comprising administering to vertebrate, e.g. a mammal suffering from an osteotomy bone loss an osteotomy bone loss treating amount of a Formula I$^A$ compound or a pharmaceutically acceptable salt or prodrug thereof. In one aspect the Formula I$^A$ compound is applied locally to a site of osteotomy.

Yet another aspect of this invention is directed to methods for treating alveolar bone loss in vertebrate, e.g., a mammal (including a human being), comprising administering to vertebrate, e.g., a mammal suffering from an alveolar bone loss an alveolar bone loss treating amount of a Formula I$^A$ compound or a pharmaceutically acceptable salt or prodrug thereof.

Yet another aspect of this invention is directed to methods for treating bone loss associated with periodontitis in vertebrate, e.g., a mammal (including a human being), comprising administering to vertebrate, e.g., mammal suffering from bone loss associated with periodontitis a bone loss associated with periodontitis treating amount of a Formula I$^A$ compound or a pharmaceutically acceptable salt or prodrug thereof.

Yet another aspect of this invention is directed to methods for treating childhood idiopathic bone loss in vertebrate, e.g., a mammal comprising administering to a child suffering from childhood idiopathic bone loss a childhood idiopathic bone loss treating amount of a Formula I$^A$ compound or a pharmaceutically acceptable salt or prodrug thereof.

Yet another aspect of this invention is directed to methods for treating "secondary osteoporosis", which includes glucocorticoid-induced osteoporosis, hyperthyroidism-induced osteoporosis, immobilization-induced osteoporosis, heparin-induced osteoporosis or immunosuppressive-induced osteoporosis in vertebrate, e.g., a mammal (including a human being), by administering to vertebrate, e.g., a mammal suffering from "secondary osteoporosis" a "secondary osteoporosis" treating amount of a Formula $I^A$ compound or a pharmaceutically acceptable salt or prodrug thereof.

Yet another aspect of this invention is directed to methods for treating glucocorticoid-induced osteoporosis in vertebrate, e.g., a mammal (including a human being), comprising administering to vertebrate, e.g., a mammal suffering from glucocorticoid-induced osteoporosis a glucocorticoid-induced osteoporosis treating amount of a Formula $I^A$ compound or a pharmaceutically acceptable salt or prodrug thereof.

Yet another aspect of this invention is directed to methods for treating hyperthyroidism-induced osteoporosis in vertebrate, e.g., a mammal (including a human being), comprising administering to vertebrate, e.g., a mammal suffering from hyperthyroidism-induced osteoporosis a hyperthyroidism-induced osteoporosis treating amount of a Formula $I^A$ compound or a pharmaceutically acceptable salt or prodrug thereof.

Yet another aspect of this invention is directed to methods for treating immobilization-induced osteoporosis in vertebrate, e.g., a mammal (including a human being), comprising administering to vertebrate, e.g., a mammal suffering from immobilization-induced osteoporosis a immobilization-induced osteoporosis treating amount of a Formula $I^A$ compound or a pharmaceutically acceptable salt or prodrug thereof.

Yet another aspect of this invention is directed to methods for treating heparin-induced osteoporosis in vertebrate, e.g., a mammal (including a human being), comprising administering to vertebrate, e.g., a mammal suffering from heparin-induced osteoporosis a heparin-induced osteoporosis treating amount of a Formula $I^A$ compound or a pharmaceutically acceptable salt or prodrug thereof.

Yet another aspect of this invention is directed to methods for treating immunosuppressive-induced osteoporosis in vertebrate, e.g., a mammal (including a human being), comprising administering to vertebrate, e.g., a mammal suffering from immunosuppressive-induced osteoporosis an immunosuppressive-induced osteoporosis treating amount of a Formula $I^A$ compound or a pharmaceutically acceptable salt or prodrug thereof.

Yet another aspect of this invention is directed to methods for treating a bone fracture in vertebrate, e.g., a mammal (including a human being), comprising administering to vertebrate, e.g., a mammal suffering from a bone fracture a bone fracture treating amount of a Formula $I^A$ compound or a pharmaceutically acceptable salt or prodrug thereof. In one aspect of this invention for treating a bone fracture the Formula $I^A$ compound or a pharmaceutically acceptable salt or prodrug thereof is applied locally to the site of bone fracture. In another aspect of this invention the Formula $I^A$ compound or a pharmaceutically acceptable salt or prodrug thereof is administered systemically.

Yet another aspect of this invention is directed to methods for enhancing bone healing following facial reconstruction or maxillary reconstruction or mandibular reconstruction in vertebrate, e.g., a mammal (including a human being), comprising administering to vertebrate, e.g., a mammal which has undergone facial reconstruction or maxillary reconstruction or mandibular reconstruction a bone enhancing amount of a Formula $I^A$ compound or a pharmaceutically acceptable salt or prodrug thereof. In one aspect of this method the Formula $I^A$ compound or a pharmaceutically acceptable salt or prodrug thereof is applied locally to the site of bone reconstruction.

Yet another aspect of this invention is directed to methods for treating prosthetic ingrowth in vertebrate, e.g., a mammal (including a human being), comprising administering to vertebrate, e.g., a mammal suffering from prosthetic ingrowth a prosthetic ingrowth treating amount of a Formula $I^A$ compound or a pharmaceutically acceptable salt or prodrug thereof.

Yet another aspect of this invention is directed to methods for inducing vertebral synostosis in vertebrate, e.g., a mammal (including a human being), comprising administering to vertebrate, e.g., a mammal undergoing surgery for vertebral synostosis a therapeutically effective amount of a Formula $I^A$ compound or a pharmaceutically acceptable salt or prodrug thereof.

Yet another aspect of this invention is directed to methods for enhancing long bone extension in vertebrate, e.g., a mammal (including a human being), comprising administering to vertebrate, e.g., a mammal suffering from an insufficiently sized long bone a long bone enhancing amount of a Formula $I^A$ compound or a pharmaceutically acceptable salt or prodrug thereof.

Yet another aspect of this invention is directed to methods for strengthening a bone graft in vertebrate, e.g., a mammal including a human being), comprising administering to vertebrate, e.g., a mammal in receipt of a bone graft a bone graft strengthening amount of a Formula $I^A$ compound or a pharmaceutically acceptable salt or prodrug thereof. In one aspect of this method the Formula $I^A$ compound or a pharmaceutically acceptable salt or prodrug thereof is applied locally to the site of the bone graft.

A preferred dosage is about 0.001 to 100 mg/kg/day of the Formula $I^A$ compound or a pharmaceutically acceptable salt or prodrug thereof. An especially preferred dosage is about 0.01 to 10 mg/kg/day of the Formula $I^A$ compound or a pharmaceutically acceptable salt or prodrug thereof.

This invention is also directed to pharmaceutical compositions which comprise a therapeutically effective amount of a compound of Formula I or a pharmaceutically acceptable salt or prodrug thereof and a pharmaceutically acceptable carrier.

This invention is also directed to pharmaceutical compositions for the augmentation of bone mass which comprise a bone mass augmenting amount of a compound of Formula I above or a pharmaceutically acceptable salt or prodrug thereof and a pharmaceutically acceptable carrier.

This invention is also directed to pharmaceutical compositions for the treatment of a condition which presents with low bone mass in vertebrate, e.g., a mammal (including a human being), which comprise a low bone mass condition treating amount of a compound of Formula I above or a pharmaceutically acceptable salt or prodrug thereof and a pharmaceutically acceptable carrier.

This invention is also directed to pharmaceutical compositions for the treatment of osteoporosis, bone fractures, osteotomy bone loss, bone loss associated with periodontitis, or prosthetic ingrowth in vertebrate, e.g., a mammal (including a human being), which comprises a therapeutically effective amount of a compound of Formula I above or a pharmaceutically acceptable salt or prodrug thereof and a pharmaceutically acceptable carrier.

This invention is also directed to pharmaceutical compositions for the treatment of "secondary osteoporosis", which includes glucocorticoid-induced osteoporosis, hyperthyroidism-induced osteoporosis, immobilization-induced osteoporosis, heparin-induced osteoporosis or immunosuppressive-induced osteoporosis in vertebrate, e.g., a mammal (including a human being), which comprise a "secondary osteoporosis" treating amount of a compound of Formula I above or a pharmaceutically acceptable salt or prodrug thereof and a pharmaceutically acceptable carrier.

This invention is also directed to pharmaceutical compositions for the treatment of osteoporosis in vertebrate, e.g., a mammal (including a human being), which comprise an osteoporosis treating amount of a compound of the Formula I above or a pharmaceutically acceptable salt or prodrug thereof and a pharmaceutically acceptable carrier.

This invention is also directed to pharmaceutical compositions for enhancing bone fracture healing in vertebrate, e.g., a mammal (including a human being), which comprise a bone fracture treating amount of a compound of the Formula I above or a pharmaceutically acceptable salt or prodrug thereof and a pharmaceutically acceptable carrier.

This invention is also directed to pharmaceutical compositions for the treatment of osteotomy bone loss in vertebrate, e.g., a mammal (including a human being), which comprise an osteotomy bone loss treating amount of a compound of the Formula I above or a pharmaceutically acceptable salt or prodrug thereof and a pharmaceutically acceptable carrier.

This invention is also directed to pharmaceutical compositions for the treatment of alveolar bone loss in vertebrate, e.g., a mammal (including a human being), which comprise an alveolar bone loss treating amount of a compound of the Formula I above or a pharmaceutically acceptable salt or prodrug thereof and a pharmaceutically acceptable carrier.

This invention is also directed to pharmaceutical compositions for the treatment of childhood idiopathic bone loss in a child which comprises a childhood idiopathic bone loss treating amount of a compound of the Formula I above or a pharmaceutically acceptable salt or prodrug thereof and a pharmaceutically acceptable carrier.

This invention is also directed to pharmaceutical compositions for the augmentation of bone healing following facial reconstruction or maxillary reconstruction or mandibular reconstruction in vertebrate, e.g., a mammal (including a human being), which comprise a bone healing amount of a compound of the Formula I above or a pharmaceutically acceptable salt or prodrug thereof and a pharmaceutically acceptable carrier.

This invention is also directed to pharmaceutical compositions for the treatment of bone loss associated with periodontitis in vertebrate, e.g., a mammal (including a human being), which comprise a bone loss associated with periodontitis treating amount of a compound of the Formula I above or a pharmaceutically acceptable salt or prodrug thereof and a pharmaceutically acceptable carrier.

This invention is also directed to pharmaceutical compositions for the treatment of prosthetic ingrowth in vertebrate, e.g., a mammal (including a human being), which comprise a prosthetic ingrowth treating amount of a compound of the Formula I above or a pharmaceutically acceptable salt or prodrug thereof and a pharmaceutically acceptable carrier.

This invention is also directed to pharmaceutical compositions for inducing vertebral synostosis in vertebrate, e.g., a mammal (including a human being), which comprise a therapeutically effective amount of a compound of the Formula I above or a pharmaceutically acceptable salt or prodrug thereof and a pharmaceutically acceptable carrier.

This invention is also directed to pharmaceutical compositions for the augmentation of long bone extension in vertebrate, e.g., a mammal (including a human being), which comprise bone mass augmentation treating amount of a compound of the Formula I above or a pharmaceutically acceptable salt or prodrug thereof and a pharmaceutically acceptable carrier.

This invention is also directed to pharmaceutical compositions for the treatment of glucocorticoid-induced osteoporosis in vertebrate, e.g., a mammal (including a human being), which comprise a glucocorticoid-induced osteoporosis treating amount of a compound of the Formula I above or a pharmaceutically acceptable salt or prodrug thereof and a pharmaceutically acceptable carrier.

This invention is also directed to pharmaceutical compositions for the treatment of hyperthyroidism-induced osteoporosis in vertebrate, e.g., a mammal (including a human being), which comprise a hyperthyroidism-induced osteoporosis treating amount of a compound of the Formula I above or a pharmaceutically acceptable salt or prodrug thereof and a pharmaceutically acceptable carrier.

This invention is also directed to pharmaceutical compositions for the treatment of immobilization-induced osteoporosis in vertebrate, e.g., a mammal (including a human being), which comprise an immobilization-induced osteoporosis treating amount of a compound of the Formula I above or a pharmaceutically acceptable salt or prodrug thereof and a pharmaceutically acceptable carrier.

This invention is also directed to pharmaceutical compositions for the treatment of heparin-induced osteoporosis in vertebrate, e.g., a mammal (including a human being) which comprise a heparin-induced osteoporosis treating amount of a compound of the Formula I above or a pharmaceutically acceptable salt or prodrug thereof and a pharmaceutically acceptable carrier.

This invention is also directed to pharmaceutical compositions for the treatment of immunosuppressive-induced osteoporosis in vertebrate, e.g., a mammal (including a human being) which comprise an immunosuppressive-induced osteoporosis treating amount of a compound of the Formula I above or a pharmaceutically acceptable salt or prodrug thereof and a pharmaceutically acceptable carrier.

Yet another aspect of this invention are combinations of the Formula I compounds or a pharmaceutically acceptable salt or prodrug thereof and other compounds as described below.

Yet another aspect of this invention is directed to pharmaceutical compositions comprising a compound of Formula I above or a pharmaceutically acceptable salt or prodrug thereof and an anti-resorptive agent and for the use of such compositions for the treatment or prevention of conditions which present with low bone mass, including osteoporosis in vertebrates, e.g., mammals (e.g., humans, particularly women) or the use of such compositions for other bone mass augmenting uses.

The combinations of this invention comprise a therapeutically effective amount of a first compound, said first compound being a Formula I compound or a pharmaceutically acceptable salt or prodrug thereof; and a therapeutically effective amount of a second compound, said second compound being an anti-resorptive agent such as an estrogen agonist/antagonist or a bisphosphonate.

Another aspect of this invention are methods for treating vertebrates, e.g., mammals which present with low bone mass comprising administering to vertebrate, e.g., a mammal having a condition which presents with low bone mass
  a. an amount of a first compound, said first compound being a Formula $I^A$ compound or a pharmaceutically acceptable salt or prodrug thereof; and
  b. an amount of a second compound, said second compound being an anti-resorptive agent such as an estrogen agonist/antagonist or a bisphosphonate.

Such compositions and methods may also be used for other bone mass augmenting uses.

A preferred aspect of this method is wherein the condition which presents with low bone mass is osteoporosis.

Another preferred aspect of this method is wherein the first compound and the second compound are administered substantially simultaneously.

Another preferred aspect of this method is wherein the first compound is administered for a period of from about three months to about three years.

Optionally the administration of the first compound is followed by administration of the second compound wherein the second compound is an estrogen agonist/antagonist for a period of from about three months to about three years without the administration of the first compound during the second period of from about three months to about three years.

Alternatively, the administration of the first compound is followed by administration of the second compound wherein the second compound is an estrogen agonist/antagonist for a period greater than about three years without the administration of the first compound during the greater than about three year period.

Another aspect of this invention is a kit comprising:
a. an amount of a Formula I$^A$ compound or a pharmaceutically acceptable salt or prodrug thereof and a pharmaceutically acceptable carrier in a first unit dosage form;
b. an amount of an anti-resorptive agent such as an estrogen agonist/antagonist or a bisphosphonate and a pharmaceutically acceptable carrier in a second unit dosage form; and
c. container means for containing said first and second dosage forms.

Yet another aspect of this invention is directed to pharmaceutical compositions including a compound of Formula I$^A$ above or a pharmaceutically acceptable salt or prodrug thereof and another bone anabolic agent (although the other bone anabolic agent may be a different Formula I compound) and for the use of such compositions for the treatment of conditions which present with low bone mass, including osteoporosis in vertebrates, e.g., mammals (e.g., humans, particularly women) or the use of such compositions for other bone mass augmenting uses.

The combination comprises a therapeutically effective amount of a first compound, said first compound being a Formula I$^A$ compound or a pharmaceutically acceptable salt or prodrug thereof; and a therapeutically effective amount of a second compound, said second compound being another bone anabolic agent.

Another aspect of this invention are methods for treating vertebrates, e.g., mammals which present with low bone mass comprising administering to vertebrate, e.g., a mammal having a condition which presents with low bone mass
a. an amount of a first compound, said first compound being a Formula I$^A$ compound or a pharmaceutically acceptable salt or prodrug therof; and
b. an amount of a second compound, said second compound being another bone anabolic agent other than the Formula I$^A$ compound.

Such compositions and methods may also be used for other bone mass augmenting uses.

A preferred aspect of this method is wherein the condition which presents with low bone mass is osteoporosis.

Another preferred aspect of this method is wherein the first compound and the second compound are administered substantially simultaneously.

Another aspect of this invention is a kit comprising:
a. an amount of a Formula I compound or a pharmaceutically acceptable salt or prodrug thereof and a pharmaceutically acceptable carrier in a first unit dosage form;
b. an amount of a second compound, said second compound being a bone anabolic agent other than the Formula I compound of part a above; and
c. container means for containing said first and second dosage forms.

Where used in any of the above methods, kits and compositions, certain bone anabolic agents, estrogen agonists/antagonists and bisphosphonates are preferred or especially preferred.

Preferred bone anabolic agents include IGF-1, prostaglandin, prostaglandin agonist/antagonist, sodium fluoride, parathyroid hormone (PTH), active fragments of parathyroid hormone, parathyroid hormone related peptides and active fragments and analogues of parathyroid hormone related peptides, growth hormone or growth hormone secretagogues and the pharmaceutically acceptable salts thereof.

Preferred estrogen agonist/antagonists include droloxifene, raloxifene, tamoxifen; 4-hydroxy-tamoxifen; toremifene; centchroman; levormeloxifene; idoxifene; 6-(4-hydroxy-phenyl)-5-[4-(2-piperidin-1-yl-ethoxy)-benzyl]-naphthalen-2-ol; {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone;
cis-6-(4-fluoro-phenyl)-5-[4-(2-piperidin-1-yl-ethoxy)-phenyl]-5,6,7,8-tetrahydro-naphthalene-2-ol;
(−)-cis-6-phenyl-5-[4-(2-pyrrolidin-1-yl-ethoxy)-phenyl]-5,6,7,8-tetrahydro-naphthalene-2-ol;
cis-6-phenyl-5-[4-(2-pyrrolidin-1-yl-ethoxy)-phenyl]-5,6,7,8-tetrahydro-naphthalene-2-ol;
cis-1-[6'-pyrrolodinoethoxy-3'-pyridyl]-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-[4-(2-piperidin-1-yl-ethoxy)-phenyl]-5,6,7,8-tetrahydro-naphthalene-2-ol; and
1-(4'-pyrrolidinolethoxyphenyl)-2-phenyl-6-hydroxy-1,2,3,4-tetrahydroisoquinoline and the pharmaceutically acceptable salts thereof.

Especially preferred estrogen agonist/antagonists include droloxifene;
cis-6-(4-fluoro-phenyl)-5-[4-(2-piperidin-1-yl-ethoxy)-phenyl]-5,6,7,8-tetrahydro-naphthalene-2-ol;
(−)-cis-6-phenyl-5-[4-(2-pyrrolidin-1-yl-ethoxy)-phenyl]-5,6,7,8-tetrahydro-naphthalene-2-ol;
cis-6-phenyl-5-[4-(2-pyrrolidin-1-yl-ethoxy)-phenyl]-5,6,7,8-tetrahydro-naphthalene-2-ol;
cis-1-[6'-pyrrolodinoethoxy-3'-pyridyl]-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-[4-(2-piperidin-1-yl-ethoxy)-phenyl]-5,6,7,8-tetrahydro-naphthalene-2-ol;
1-(4'-Pyrrolidinolethoxyphenyl)-2-phenyl-6-hydroxy-1,2,3,4-tetrahydroisoquinoline; and the pharmaceutically acceptable salts thereof.

Preferred bisphosphonates include, tiludronic acid, alendronic acid, ibandronic acid, risedronic acid, etidronic acid, clodronic acid, and pamidronic acid and their pharmaceutically acceptable salts.

The phrase "condition(s) which presents with low bone mass" refers to a condition where the level of bone mass is below the age specific normal as defined in standards by the World Health Organization "Assessment of Fracture Risk and its Application to Screening for Postmenopausal Osteoporosis (1994). Report of a World Health Organization Study Group. World Health Organization Technical Series 843". Included in "condition(s) which presents with low bone mass" are primary and secondary osteoporosis. Secondary osteoporosis includes glucocorticoid-induced osteoporosis, hyperthyroidism-induced osteoporosis, immobilization-induced osteoporosis, heparin-induced osteoporosis and immunosuppressive-induced osteoporosis. Also included is periodontal disease, alveolar bone loss, osteotomy bone loss and childhood idiopathic bone loss. The phrase "condition(s) which presents with low bone mass" also includes long term complications of osteoporosis such as curvature of the spine, loss of height and prosthetic surgery.

The phrase "condition which presents with low bone mass" also refers to vertebrate, e.g., a mammal known to have a significantly higher than average chance of developing such diseases as are described above including osteoporosis (e.g., post-menopausal women, men over the age of 60).

Other bone mass augmenting or enhancing uses include increasing the bone fracture healing rate, enhancing the rate of successful bone grafts, bone healing following facial reconstruction or maxillary reconstruction or mandibular reconstruction, prosthetic ingrowth, vertebral synostosis or long bone extension.

Those skilled in the art will recognize that the term bone mass actually refers to bone mass per unit area which is sometimes (although not strictly correctly) referred to as bone mineral density.

The term "treating", "treat" or "treatment" as used herein includes preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula I compounds include but are not limited to substituents wherein the Z moiety is independently carboxyl and the free hydrogen is replaced by $(C_1–C_4)$alkyl, $(C_2–C_7)$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1–C_2)$alkylamino$(C_2–C_3)$alkyl (such as b-dimethylaminoethyl), carbamoyl-$(C_1–C_2)$alkyl, N,N-di $(C_1–C_2)$alkylcarbamoyl-$(C_1–C_2)$alkyl and piperidino-, pyrrolidino- or morpholino$(C_2–C_3)$alkyl.

Exemplary five to six membered aromatic rings optionally having one or two heteroatoms selected independently from oxygen, nitrogen and sulfur (i.e., X rings) are phenyl, furyl, thienyl, pyrrolyl, oxazolyl, thiazolyl, imidazolyl, pyrazolyl, isoxazolyl, isothiazolyl, pyridyl, pyridiazinyl, pyrimidinyl and pyrazinyl.

Exemplary partially saturated, fully saturated or fully unsaturated five to eight membered rings optionally having one to four heteroatoms selected independently from oxygen, sulfur and nitrogen (i.e., Ar, $Ar^1$ and $Ar^2$) are cyclopentyl, cyclohexyl, cycloheptyl, cyclooctyl and phenyl. Further exemplary five membered rings are furyl, thienyl, 2H-pyrrolyl, 3H-pyrrolyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings are 2H-pyranyl, 4H-pyranyl, pyridyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl.

Further exemplary seven membered rings are azepinyl, oxepinyl, thiepinyl and 1,2,4-diazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, taken independently, optionally having one to four heteroatoms selected independently from nitrogen, sulfur and oxygen are indolizinyl, indolyl, isoindolyl, 3H-indolyl, 1H-isoindolyl, indolinyl, cyclopenta(b) pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, 4H-quinoiizinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

Exemplary tricyclic rings consisting of three fused partially saturated, fully saturated or fully unsaturated five and/or six membered rings, taken independently, optionally having one to four heteroatoms selected independently from nitrogen, sulfur and oxygen are indacenyl, biphenylenyl, acenaphthylenyl, fluorenyl, phenalenyl, phenanthrenyl, anthracenyl, naphthothienyl, thianthrenyl, xanthenyl, phenoxathiinyl, carbazolyl, carbolinyl, phenanthridinyl, acridinyl, perimidinyl, phenanthrolinyi, phenazinyl, phenothiazinyl and phenoxazinyl. It will be understood that the fully saturated and all parially unsaturated forms of these rings are within the scope of this invention. Further, it will be understood that the heteroatom or heteroatoms in the heterocyclic rings can be substituted at any non-bridgehead position within said ring.

By alkylene is meant saturated hydrocarbon (straight chain or branched) wherein a hydrogen atom is removed from each of the terminal carbons. Exemplary of such groups (assuming the designated length encompases the particular example) are methylene, ethylene, propylene, butylene, pentylene, hexylene and heptylene.

By alkenylene is meant a hydrocarbon containing monounsaturation in the form of one double bond wherein said hydrocarbon is straight chain or branched and wherein a hydrogen atom is removed from each of the terminal carbons. Exemplary of such groups (assuming the designated length encompasses the particular example) are ethenylene (or vinylene), propenylene, butenylene, pentenylene, hexenylene and heptenylene.

By alkynylene is meant a hydrocarbon containing di-unsaturation in the form of one triple bond wherein said hydrocarbon is straight chain or branched and wherein a hydrogen atom is removed from each of the terminal carbons. Exemplary of such groups (assuming the designated length encompasses the particular example) are ethynylene, propynylene, butynylene, pentynylene, hexynylene and heptynylene.

By halo is meant chloro, bromo, iodo, or fluoro.

By alkyl is meant straight chain saturated hydrocarbon or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

As used herein the term mono-N- or di-N,N—($C_1$–$C_x$) alkyl . . . refers to the ($C_1$–$C_x$)alkyl moiety taken independently when it is di-N,N—($C_1$–$C_x$)alkyl . . . (x refers to integers and is taken independently when two ($C_1$–$C_x$)alkyl groups are present, e.g., methylethylamino is within the scope of di-N,N—($C_1$–$C_x$)alkyl).

Unless otherwise stated the "M" moieties defined above are optionally substituted (e.g., the mere listing of a substituent such as $R^1$ in a subgenus or dependent claim does not mean that M is always substituted with the $R^1$ moiety unless it is stated that the M moiety is substituted with $R^1$). However, in the compounds of Formula I, when L is a bond and M is phenyl, said phenyl group is substituted with one to three substituents. Additionally, in the compounds of Formula I, when Ar or $Ar^1$ is a fully saturated five to eight membered ring, said ring is unsubstituted.

It is to be understood that if a carbocyclic or heterocyclic moiety may be bonded or otherwise attached to a designated substrate, through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

The expression "pharmaceutically acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino2-hydroxymethyl-1,3-propanediol).

As used herein, the expressions "reaction inert solvent" and "inert solvent" refers to a solvent which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention.

The oxocyclopentane derivatives of Formulas I and $I^A$, substituted at the α- and β-positions (see structures below) of the ring relative to the carbonyl group by B—Q—Z and K—L—M, respectively, can exist as either the cis or the trans isomer. "Cis" forms of the oxocyclopentane compounds of Formulas I and $I^A$ are those compounds wherein the substituents at the α- and β-positions of said ring are both directed either above the ring or below the ring. The term "trans" indicates a stereochemistry wherein one of the substituents is directed above the ring and the other substituent is directed below the ring. Both the cis and the trans forms of the compounds of Formulas I and $I^A$ are within the scope of this invention. The trans forms are generally more preferred due to the propensity to epimerize demonstrated by the cis forms. The most preferred compounds of the invention are those compounds wherein the α substituent is directed below the ring and the β substituent is directed above the ring. Furthermore, wherein the compounds of the invention are γ-hydroxy substituted, α-substituted with B—Q—Z and β-substituted with K—L—M, the skilled person will recognize that there are three stereocenters. In that case, the compounds wherein the hydroxy group is directed down, the α-substituent is directed down and the β-substituent is directed up are the most preferred isomers.

Hydrates of the compounds of this invention are also included.

DTT means dithiothreitol. DMSO means dimethyl sulfoxide. EDTA means ethylenediamine tetraacetic acid.

The methods and compounds of this invention result in bone formation resulting in decreased fracture rates. This invention makes a significant contribution to the art by providing compounds and methods that increase bone formation resulting in prevention, retardation, and/or regression of osteoporosis and related bone disorders.

Other features and advantages will be apparent from the specification and claims which describe the invention.

DETAILED DESCRIPTION OF THE INVENTION

In general the compounds of this invention can be made by processes which include processes known in the chemical arts, particularly in light of the description contained herein. Certain processes for the manufacture of the compounds of this invention are provided as further features of the invention and are illustrated by the following reaction schemes. Other processes may be described in the examples.

Some substituents (e.g., carboxyl) may best be prepared through conversion of another functional group (for carboxyl, examples are hydroxyl or carboxaldehyde) at a point later in the synthetic sequence.

In the schemes set forth hereinbelow, the compounds of this invention are depicted in the most preferred form, having the general stereochemical substitution pattern:

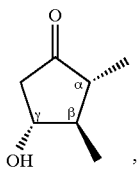

when A is OH and

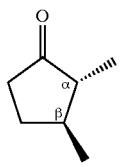

when A is H.

It will be understood by those skilled in the art that other isomeric forms, including, when A is OH, the other trans-trans form, and either of the cis-trans forms, and, when A is H, the other trans form and the cis form, can be prepared by the methods set forth in those schemes or by methods generally known to those skilled in the art. All of the possible stereoisomeric forms are included within the scope of this invention. Further, in the schemes set forth hereinbelow, the "R" substituent, where it appears, is $(C_1-C_6)$alkyl; the "n" substituent, where it appears, is 1–3; and PGX is a reagent used to attach a protecting group "PG." The "X" portion is usually a halo or other leaving group which, when attached to PG, forms the reagent used to attach the protecting group. For example, if the protecting group is acetyl, a suitable PGX group would be acetyl chloride.

In general, compounds of general Formula I can be prepared according to the methods described in Schemes 1 and 2. In general, the sequences involve 1,4-addition of the appropriate organometallic reagent onto the desired 2-substituted 2-cyclopenten-1-one (1-1). The substituent at the two position of the 2-cyclopenten-1-one template contains a carboxylic acid or acid isostere suitably masked with the appropriate protecting group (see *Protecting Groups in Organic Synthesis*, Second Edition, T. W. Greene and P. G. M. Wuts, John Wiley and Sons, Inc., 1991). Alternatively, the carboxylic acid moiety may be linked to solid support resin, such as Wang (polystyrene) resin. Other acid isosteres can be employed by appropriately modifying these schemes using methods known to those skilled in the art (see Scheme 10 for example). If desired, the C-4 position of the 2-cyclopenten-1-one may contain a hydroxy group, also suitably protected. Preferred protecting groups for the hydroxy group include tert-butyldimethylsilyl or tetrahydropyranyl.

In Scheme 1, introduction of (E)-1,2-bis(tributylstannyl) ethylene (1-2) (see A. F. Renaldo, J. W. Labadie, and J. K. Stille in Org. Synth. (1989), 67, 86–97 for preparation) to the 2-substituted 2-cyclopenten-1-one is accomplished using the protocol described by J. R. Behling and coworkers (J. Am. Chem. Soc., 1988, 110, 2641–2643) to generate compound 1-3. Alternatively, 1-2 can be transformed to the lithium reagent by treatment with an alkyl lithium reagent such as MeLi, n-BuLi, or tert-BuLi in a reaction inert solvent, for example, an aprotic solvent such as tetrahydrofuran or diethyl ether at low temperature (−78° C. to −40° C.). Conversion of the lithium reagent to the cuprate is accomplished by treatment of the organolithium compound with a copper(I) reagent such as copper cyanide or copper iodide at low temperature (−78° C. to 0° C.). Addition of the cuprate derived from compound 1-2 to compounds of general formula 1-1 generates intermediate 1-3.

When A is H, to ensure the relative trans stereochemistry at the α and β positions on the ring system, equilibration of the resulting product to the trans product 1-3 is accomplished with a base, preferably sodium methoxide in methanol or potassium tert-butoxide in a reaction inert solvent such as tetrahydrofuran. Stille coupling of intermediate 1-3 to a variety of aryl halides or aryl triflates provides compounds of general formula 1-4. Stille coupling chemistry is reviewed in J. K Stille, Angew. Chem. Int. Ed. Engl. 1986, 25, 508–524 and T. N. Mitchell, Synthesis 1991, 803–815. The coupling is performed in the presence of a palladium catalyst, such as tetrakis(triphenylphosphine)palladium(0), palladium(0) bis(dibenzylideneacetone), tris(dibenzylideneacetone)dipalladium(0), palladium(II) bis(benzonitrile) dichloride, or palladium(II) bis(acetonitrile) dichloride. The reaction is preferably carried out in a solvent such as tetrahydrofuran, N,N-dimethylformamide, or toluene with or without the addition of a base such as diisopropyethylamine at temperatures ranging from 25° C. to 130° C. It is generally preferred that the temperature be maintained from 50° C. to 100° C. A ligand such as tri-2-furylphosphine or triphenylarsene may also be added to the reaction. In cases where A is H, removal of either the ester protecting group or the solid phase resin using methods known to those skilled in the art, such as trifluoroacetic acid, provides styrene compounds of general formula 1-5. If A is a protected hydroxy group, deprotection is accomplished using methods known to those skilled in the art. For example, if A is protected with a tert-butyldimethylsilyl group, this protecting group can be removed by treatment with tetrabutylammonium fluoride or by stirring in a mixture of acetic acid:water:tetrahydrofuran (3:1:1). If desired, hydrogenation of the styrene intermediate 1-4 followed by deprotection of the acidic moiety provides compounds of general formula 1-6. The hydrogenation is generally performed in the presence of a palladium or platinum catalyst and in reaction inert solvents such as methanol, ethanol, and/or ethyl acetate. These skilled in the art will recognize that certain substituents on the aromatic ring may not survive hydrogenation conditions. In those cases, a person skilled in the art would modify the synthesis accordingly, e.g., a hydrogenation method could be selected which is more selective for a double bond, or the substituents could be attached to the nucleus at a latter point in the synthesis using methods well known to those skilled in the art.

In an analogous fashion to Scheme 1, compounds of general formulas 2-9 and 2-11 can be prepared as set forth in Scheme 2. The vinyl stannane intermediate 1-3 is coupled with an appropriate acid chloride in the presence of a palladium catalyst, such as tetrakis(triphenylphosphine)

palladium(0), palladium(0) bis(dibenzylideneacetone), tris(dibenzylideneacetone)dipalladium(0), palladium(II) bis(benzonitrile) dichloride, or palladium(II) bis(acetonitrile) dichloride. The reaction is typically performed in a reaction inert solvent such as toluene, tetrahydrofuran, or chloroform with or without the presence of a base. Ordinarily amines such as diisopropylethylamine or triethylamine are used, with diisopropylethylamine being preferred. The reaction is generally performed under an atmosphere of carbon monoxide. A ligand such as tri-2-furylphosphine or triphenylarsene may also be added to the reaction. Alternatively, compounds of formula 1-3 can be treated with an aromatic halide or aromatic triflate under an atmosphere of carbon monoxide to provide intermediates of formula 2-8.

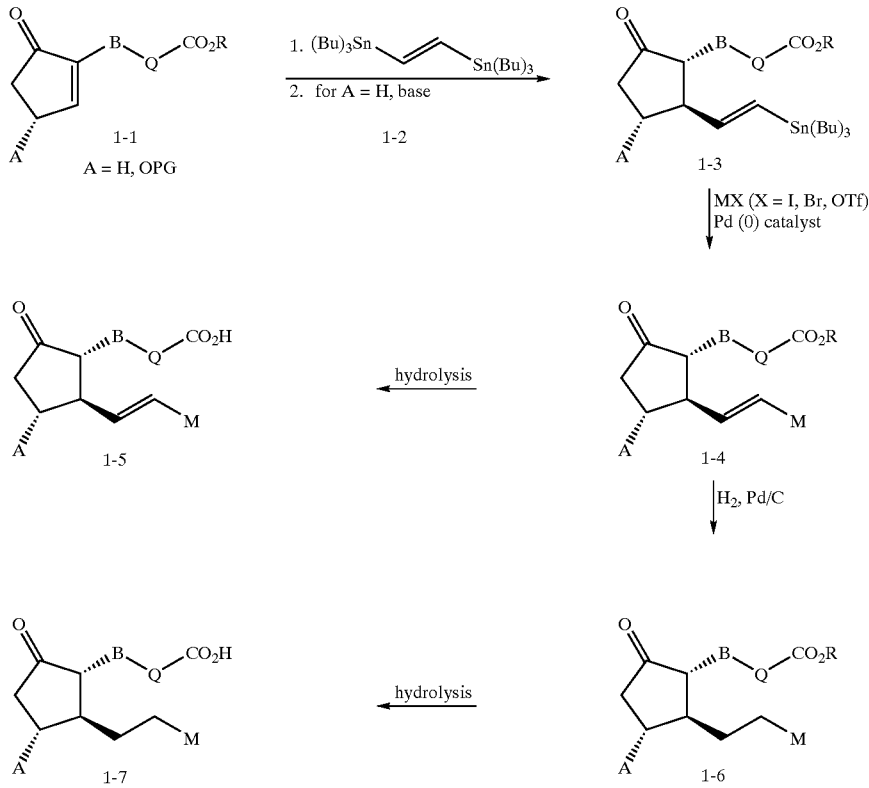

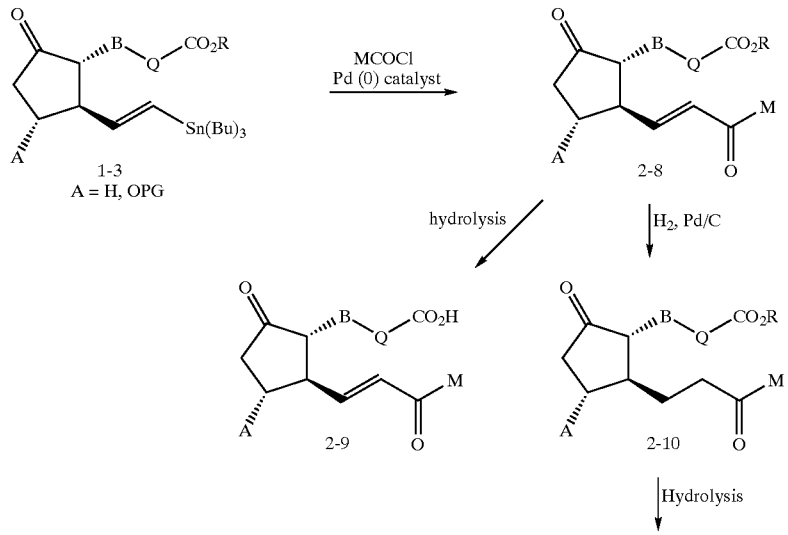

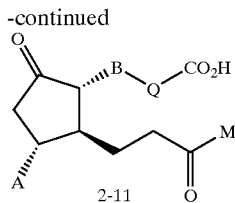

2-11

Alternative methods for the preparation of compounds of general formulas 1-5 and 2-9 are shown in Schemes 3 and 4. Intermediate 3-12 is prepared by 1,4-addition of a vinyl organometallic reagent such as vinylmagnesium bromide in the presence of a copper(I) catalyst, such as copper cyanide, copper iodide, or copper bromide. The reaction is generally performed in a reaction inert, aprotic solvent such as tetrahydrofuran or diethyl ether at low temperature (e.g., −78° C. to 0° C.). Subsequent Heck coupling of 3-12 with an aryl halide (preferably an aryl bromide or aryl iodide), aryl triflate, or a ring system which contains a vinyl iodide, vinyl bromide or vinyl triflate is performed using a palladium catalyst, such as palladium acetate or tetrakis (triphenylphosphine)palladium(0) in the presence of a trialkylamine such as triethylamine. When performing a Heck coupling with an aryl bromide, a triarylphosphine may be added to the reaction. The reaction is typically performed in dimethylformamide or acetonitrile at temperatures ranging from 0° C. to 150° C. and preferably from 50° C. to about 100° C. Using the sequences described above in Scheme 1, compounds of general formula 1-5 and 1-7 can be obtained. In a similar fashion, compounds of general formula 2-9 and 2-11 can be prepared by Heck coupling of intermediate 3-12 with a variety of acid chlorides (see Scheme 4). In cases where M represents a partially saturated ring system, hydrogenation will generate a saturated ring system.

Scheme 3

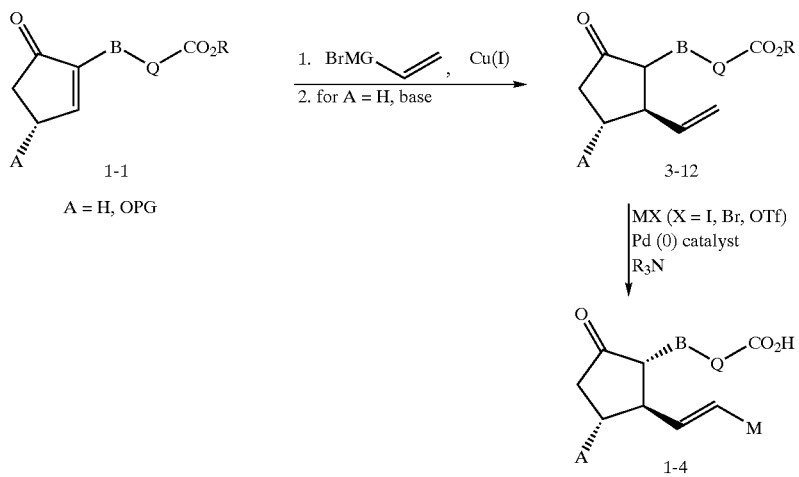

Scheme 4

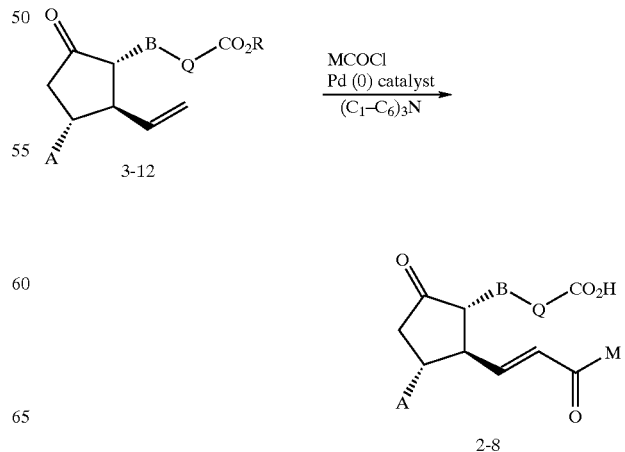

The aromatic halides and aromatic acid chlorides used in the above Schemes are commonly available from commercial sources. If desired, an aromatic acid may be converted to the acid chloride by treatment with a chlorinating reagent such as thionyl chloride, phosphorous trichloride, or phosphorous pentachloride in an inert solvent. Aromatic triflates can be prepared from commercially available aromatic alcohols by treatment with triflic anhydride or N-phenyltrifluoromethanesulfonimide in the presence of a base such as pyridine.

As described in Scheme 5, compounds of general formula 1-1 can be prepared from compounds of formula 5-1 using the methods described by Ono and coworkers (Synthesis, 1981, 12, 1003–4). The method involves condensation of 4-(1-cyclopenten-1-yl)morpholine with the appropriate aldehyde containing a protected acidic functional group. This condensation is carried out by heating the two reagents in a solvent such as benzene or toluene with continual removal of the resulting water. The enamine which forms is cleaved by stirring with an aqueous acid. The double bond is isomerized by heating the compound of formula 5-2 in an alcoholic solvent, such as methanol, in the presence of a strong acid, such as hydrogen chloride to generate a compound of formula 1-1. Compounds of formula 1-1 where Z is a cyano group can be prepared in an analogous manner. The Z group can be converted to a tetrazole at this step or a later step and then protected as described in Scheme 10.

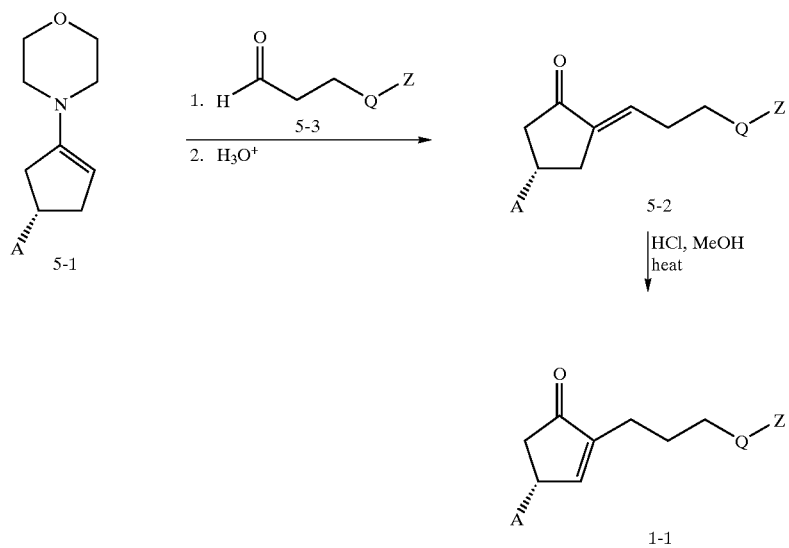

Scheme 5

Scheme 6 sets forth an alternative method for the preparation of 2-substituted 2-cyclopenten-1-ones of general formula 1-1 and follows procedures analogous to those described by C. R. Johnson and coworkers (J. Am. Chem. Soc. 1993, 115, 11014–5). The protocol involves Suzuki coupling of a 2-iodo-2-cyclopenten-1-one (6-1) (see C. R. Johnson and coworkers in Tetrahedron Lett., 33, 917, 1992) with an alkylborane which contains the desired acidic functional group suitably protected. The coupling is performed in the presence of a palladium catalyst, preferably bis(diphenylphosphino)ferrocene palladium(II) chloride, which is complexed to a ligand, such as triphenylarsene. The reaction requires addition of a base, such as cesium carbonate, and is performed in a reaction inert solvent such as a mixture of water and an organic solvent. Said organic sovent is, for example, N,N-dimethylformamide, tetrahydrofuran, or 1,2-dimethoxyethane. The alkylborane is prepared from the appropriate alkenyl compound (6-2) by addition of a boron reagent, preferably 9-borabicyclo[3.3.1]nonane (9-BBN) in an inert solvent such as tetrahydrofuran. Compounds of formula 6-2 where Z is a cyano group can be prepared in an analogous manner. The Z group can be converted at this step or a later step to a tetrazole and then protected as described in Scheme 10.

Scheme 6

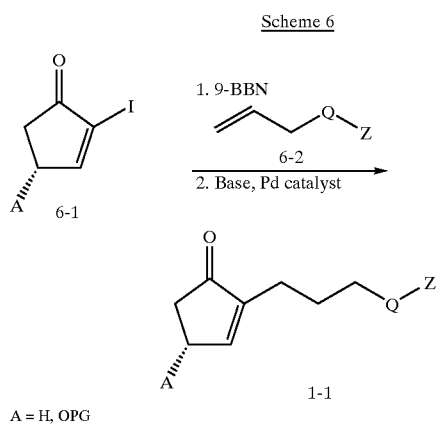

A = H, OPG

Numerous methods known to those skilled in the art exist for preparing the aldehydes of formula (5-3) which can be used for the preparation of the intermediates of general formula 1-1. Scheme 7 sets forth a preferred preparation of ester aldehydes of general formula 7-2. The protocol follows the methods of S. L. Schreiber and coworker-s (Org. Synth. 1986, 64, 150–6) and involves ozonolytic cleavage of a commercially available cycloalkene (7-1). The reaction is performed in a mixture of a reaction inert solvent, preferably a combination of dichloromethane and methanol at low temperature, preferably −78° C., by addition of ozone gas. Treatment with acetic anhydride and a suitable base such as triethylamine provides the desired methyl ester aldehydes 7-2. An alternative preparation of compounds of formula 5-3 is set forth in Scheme 8. Aryl halides or triflates of formula 8-1 are treated with allyl alcohol; a suitable Pd catalyst, preferably palladium acetate; a suitable base, preferably sodium bicarbonate; and tetrabutylammonium chloride in a suitable reaction inert, aprotic solvent such as N,N-dimethylformamide. The mixture is allowed to react at temperatures in the range of 0–125° C., preferably 40–80° C. Workup of the reaction mixture affords aldehydes of general structure 5-3. Compounds of formula 5-3 where Z is a cyano group can be prepared in an analogous manner. The Z group can be converted at this step or a later step to a tetrazole and then protected as described in Scheme 10.

Scheme 7

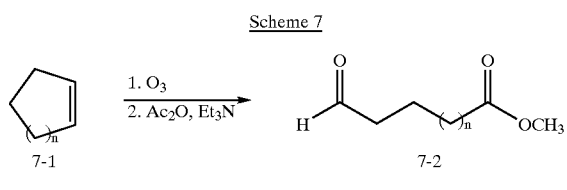

Scheme 8

X—Q—Z $\xrightarrow{\text{Pd catalyst}}$ ⟶OH

Q = thiazolyl, pyridyl, phenyl or thienyl
X = Br, I or O-Tf
8-1

-continued

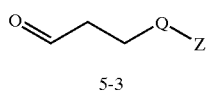

5-3

Starting alkenes of general formula 6-2 can be prepared using the methods set forth in Schemes 9 through 11. For example, in Scheme 9, olefins of general formula 6-2 can be prepared by Wittig olefination of aldehydes of general formula 9-1. Condensation of methylidene(triphenyl)phosphorane, derived from methyltriphenylphosphonium bromide and a base such as n-butyl lithium, with 9-1 provides the desired alkenes 6-2 (see I. Gosney and A. G. Rowley in Organophosphomus Reagents in Organic Synthesis, ed. J. I. G. Cadogan, Academic Press, London, 1979 or B. E. Marynoff and A. B. Reitz, Chem. Rev. 1989, 89, 863). Compounds of formula 6-2 where Z is a cyano group can also be prepared in an analogous manner. The Z group can be converted at this step or a later step to a tetrazole and then protected as described in Scheme 10.

Scheme 9

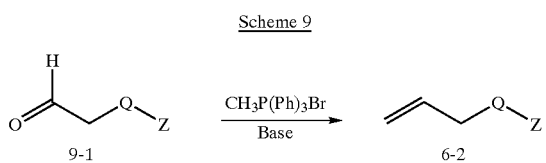

Scheme 10

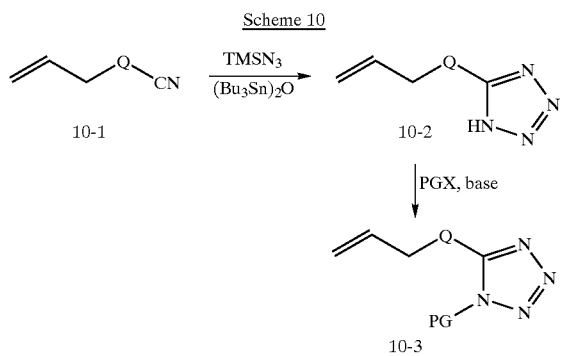

Scheme 10 sets forth a method which can be used to prepare alkenes of general formula 6-2 where Z represents a suitably protected tetrazole moiety. For example, treatment of commercially available alkenyl nitrites (10-1) with dibutyltin oxide, trimethylsilylazide, in toluene at reflux (S. J. Wittenberger and B. G. Donner, J. Org. Chem. 1993, 58, 4139–4141) provides alkenyl tetrazoles of general formula 10-2. An alternative preparation of the compounds of 10-2 involves treatment of a compound of 10-1 with sodium azide and ammonium chloride. The reaction is normally carried out in the presence of catalytic lithium chloride at temperatures ranging from 50°–150° C. For a review on preparations of tetrazoles see R. N. Butler, Tetrazoles, In Comprehensive Heterocyclic Chemistry; Potts, K. T. Ed.; Pergamon Press: Oxford, 1984, Vol. 5, pp 791–838. The alkenyl tetrazole is protected with protecting groups such as triphenylmethyl or benzyl using methods known to those skilled in the art to provide compounds of general formula 10-3. Using the method described in Scheme 5, 10-3 may be coupled to 5-1 to provide 2-substituted 2-cyclopenten-1-ones (1-1).

Scheme 11

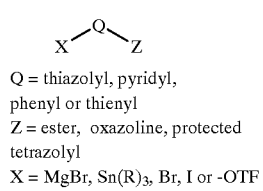

Q = thiazolyl, pyridyl, phenyl or thienyl
Z = ester, oxazoline, protected tetrazolyl
X = MgBr, Sn(R)₃, Br, I or -OTF 8-1

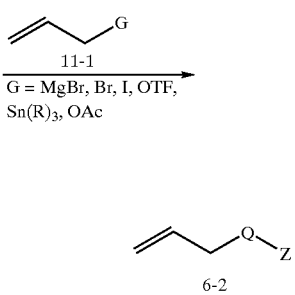

G = MgBr, Br, I, OTF, Sn(R)₃, OAc 6-2

Compounds of formula 6-2 can be prepared as set forth in Scheme 11 by reacting compounds of formula 8-1 with compounds of formula 11-1 using a variety of methods. Examples of such methods are described in the references below and include but are not limited to palladium catalyzed processes and Grignard type reactions: Meyers, A. I. Et al. J. Org. Chem.; 39; 1974; 2787–2793. Sibille, Soline; Ratovelomanana, Victorin; Perichon, Jacques; J.Chem.Soc-.Chem.Commun.; 3; 1992; 283–284. Wenkert, Ernest; Fernandes, Joao Battista; Michelotti, Enrique L.; Swindell, Charles S.; 9; 1983; 701–703. Efange, S. M. N.; Michelson, R. H.; Dutta, A. K.; Parsons, S. M.; J.Med.Chem.; 34; 8; 1991; 2638–2643. Heck, R. F.; J.Amer.Chem.Soc.; 90; 20; 1968; 5531–5534. Johnson, David K.; Ciavarri, Jeffrey P.; Ishmael, Faoud T.; Schillinger, Kurt J.; Geel, Thomas A. P. van; Stratton, Stephen M; Tetrahedron Lett.; 36; 47; 1995; 8565–8568. Bumagin, N. A.; Kasatkin, A. N.; Beletskaya, I. P.; Bull.Acad.Sci.USSR Div.Chem.Sci.(Engl.Transl.); 33; 1984; 588–594; Izv.Akad.Nauk SSSR Ser.Khim.; 3; 1984; 636–642.

It will be recognized that the compounds of Formulas I and $I^A$ of this invention can exist in radiolabelled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^3H$, $^{14}C$, $^{32}P$, $^{18}F$ and $^{36}Cl$, respectively. Compounds of Formulas I and $I^A$ of this invention which contain those radioisotopes and/or other radioisotopes of other atoms are within the scope of this invention. Tritiated, i.e., $^3H$, and carbon-14, i.e., $^{14}C$, radioisotopes are particularly preferred for their ease of preparation and detectability. Radiolabelled compounds of Formulas I and $I^A$ of this invention can generally be prepared according to methods well known to those skilled in the art. Conveniently, such radiolabelled compounds can be prepared by carrying out the procedures disclosed in the above Schemes and/or in the Examples and Preparations below by substituting a readily available radiolabelled reagent for a non-radiolabelled reagent.

Those skilled in the art will recognize that anti-resorptive agents (for example progestins, polyphosphonates, bisphosphonate(s), estrogen agonists/antagonists, estrogen, estrogen/progestin combinations, Premarin, estrone, estriol or 17α- or 17β-ethynyl estradiol) may be used in conjunction with the compounds of this invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol.

Preferred progestins are medroxyprogestrone, norethindrone and norethynodrel.

Exemplary bone resorption inhibiting polyphosphonates include polyphosphonates of the type disclosed in U.S. Pat. No. 3,683,080, the disclosure of which is incorporated herein by reference. Preferred polyphosphonates are geminal diphosphonates (also referred to as bis-phosphonates). Tiludronate disodium is an especially preferred polyphosphonate. Ibandronic acid is an especially preferred polyphosphonate. Alendronate is an especially preferred polyphosphonate. Other preferred polyphosphonates are 6-amino-1-hydroxy-hexylidene-bisphosphonic acid and 1-hydroxy-3(methylpentylamino)-propylidene bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3-3-dimethyl-3-amino-1-hydroxy-1,1-diphosphonic acid, phenyl amino methane diphosphonic acid,N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used as the second compound of this invention. The term estrogen agonist/antagonist refers to compounds which bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art according to standard assays including estrogen receptor binding assays, standard bone histomorphometric and densitometer methods, and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below.

A preferred estrogen agonist/antagonist is droloxifene: (phenol, 3-[1-[4-[2-(dimethylamino)ethoxy]phenyl]-2-phenyl-1-butenyl]-, (E)-) and related compounds which are disclosed in U.S. Pat. No. 5,047,431, the disclosure of which is incorporated herein by reference.

Another preferred estrogen agonist/antagonist is tamoxifen: (ethanamine,2-[-4-(1,2-diphenyl-1-butenyl)phenoxy]-N,N-dimethyl, (Z)-2-, 2-hydroxy-1,2,3-propanetricarboxylate(1:1)) and associated compounds which are disclosed in U.S. Pat. No. 4,536,516, the disclosure of which is incorporated herein by reference.

Another related compound is 4-hydroxy tamoxifen which is disclosed in U.S. Pat. No. 4,623,660, the disclosure of which is incorporated herein by reference.

A preferred estrogen agonist/antagonist is raloxifene: (methanone, [6-hydroxy-2-(4-hydroxyphenyl)benzo[b]thien-3-yl][4-[2-(1-piperidinyl)ethoxy]phenyl],-hydrochloride) which is disclosed in U.S. Pat. No. 4,418,068, the disclosure of which is incorporated herein by reference.

Another preferred estrogen agonist/antagonist is toremifene: (ethanamine, 2-[4-(4-chloro-1,2-diphenyl-1-butenyl)phenoxy]-N,N-dimethyl-, (Z)-, 2-hydroxy-1,2,3-propanetricarboxylate (1:1) which is disclosed in U.S. Pat. No. 4,996,225, the disclosure of which is incorporated herein by reference.

Another preferred estrogen agonist/antagonist is centchroman: 1-[2-[4-(-methoxy-2,2-dimethyl-3-phenyl-chroman-4-yl)-phenoxy]-ethyl]-pyrrolidine, which is disclosed in U.S. Pat. No. 3,822,287, the disclosure of which is incorporated. herein by reference. Also preferred is levormeloxifene.

Another preferred estrogen agonist/antagonist is idoxifene: pyrrolidine, 1-[-4-[[1-(4-iodophenyl)-2-phenyl-1-butenyl]phenoxy]ethy] which is disclosed in U.S. Pat. No. 4,839,155, the disclosure of which is incorporated herein by reference.

Another preferred estrogen agonist/antagonist is 6-(4-hydroxy-phenyl)-5-[4-(2-piperidin-1-yl-ethoxy)-benzyl]-naphthalen -2-ol which is disclosed in U.S. Pat. No. 5,484, 795, the disclosure of which is incorporated herein by reference.

Another preferred estrogen agonist/antagonist is {4-[2-(2-aza-bicyclo[2.2.1]hept-2-yl)-ethoxy]-pheny}-[6-hydroxy-2-(4-hydroxy-phenyl)-benzo[b]thiophen-3-yl]-methanone which is disclosed, along with methods of preparation, in PCT publication no. WO 95/10513 assigned to Pfizer Inc.

Other preferred estrogen agonist/antagonists include compounds as described in commonly assigned U.S. Pat. No. 5,552,412, the disclosure of which is incorporated herein by reference. Especially preferred compounds described therein are:

cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolodinoethoxy-3'-pyrdyl]-2-phenyl-6-hydroxy-1,2,3,4-tetrahydronaphthalene;

1-(4'-pyrrolidinoethoxyphenyl)-2-(4"-fluoro-phenyl)6-hydroxy-1,2,3,4-tetrahydroisoquinoline;

cis-6-(4-hydroxyphenyl)-5-[4-(2-piperdin-1-yl-ethoxy)-phenyl]-5,6,7,8-tetrahydro-naphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814 (the disclosure of which is incorporated herein by reference). U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents (bone mass augmenting agents) may be used in conjunction with the compounds of this invention. A bone mass augmenting agent is a compound that augments bone mass to a level which is above the bone fracture threshold (as detailed in the World Health Organization Study World Health Organization, "Assessment of Fracture Risk and its Application to Screening for Postmenopausal Osteoporosis (1994). Report of a WHO Study Group. World Health Organization Technical Series 843").

Any prostaglandin, or prostaglandin agonist/antagonist may be used as the second compound of this invention (this includes utilizing two different compounds of Formula $I^A$ of this invention). Those skilled in the art will recognize that IGF-1, sodium fluoride, parathyroid hormone (PTH), active fragments of parathyroid hormone, growth hormone or growth hormone secretagogues may also be used. The following paragraphs describe exemplary second compounds of this invention in greater detail.

Any prostaglandin may be used as the second compound of this invention. The term prostaglandin refers to compounds which are analogs of the natural prostaglandins $PGD_1$, $PGD_2$, $PGE_2$, $PGE_1$ and $PGF_2$ which are useful in the treatment of osteoporosis. These compounds bind to the prostaglandin receptors. Such binding is readily determined by those skilled in the art according to standard assays (e.g., An S. et al., Cloning and Expression of the $EP_2$ Subtype of Human Receptors for Prostaglandin $E_2$, Biochemical and Biophysical Research Communications, 1993, 197(1): 263–270).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$–$C_{14}$ and a cis double bond at the $C_5$–$C_6$ position.

A variety of prostaglandins are described and referenced below, however, other prostaglandins will be known to those skilled in the art. Exemplary prostaglandins are disclosed in U.S. Pat. Nos. 4,171,331 and 3,927,197, the disclosures of each of which are incorporated herein by reference.

Norrdin et al., *The Role of Prostaglandins in Bone In Vivo*, Prostaglandins Leukotriene Essential Fatty Acids 41, 139–150, 1990 is a review of bone ariabolic prostaglandins.

Any prostaglandin agonist/antagonist may be used as the second compound of this invention. The term prostaglandin agonist/antagonist refers to compounds which bind to prostaglandin receptors (e.g., An S. et al., Cloning and Expression of the $EP_2$ Subtype of Human Receptors for Prostaglandin $E_2$, Biochemical and Biophysical Research Communications, 1993, 197(1):263–270) and mimic the action of prostaglandin in vivo (e.g., stimulate bone formation and increase bone mass). Such actions are readily determined by those skilled in the art according to standard assays. Eriksen E. F. et al., *Bone Histomorphometry*, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296. A variety of these compounds are described and referenced below; however, other prostaglandin agonists/antagonists will be known to those skilled in the art. Exemplary prostaglandin agonists/antagonists are disclosed as follows.

Commonly assigned U.S. Pat. No. 3,932,389, the disclosure of which is incorporated herein by reference, discloses 2-descarboxy-2-(tetrazol-5-yl)-11-desoxy-15-substituted-omega-pentanorprostaglandins useful for bone formation activity.

Commonly assigned U.S. Pat. No. 4,018,892, the disclosure of which is incorporated herein by reference, discloses 16-aryl-13,14-dihydro-PGE$_2$ p-biphenyl esters useful for bone formation activity.

Commonly assigned U.S. Pat. No. 4,219,483, the disclosure of which is incorporated herein by reference, discloses 2,3,6-substituted-4-pyrones useful for bone formation activity.

Commonly assigned U.S. Pat. No. 4,132,847, the disclosure of which is incorporated herein by reference, discloses 2,3,6-substituted-4-pyrones useful for bone formation activity.

U.S. Pat. No. 4,000,309, the disclosure of which is incorporated herein by reference, discloses 16-aryl-13,14-dihydro-PGE$_2$ p-biphenyl esters useful for bone formation activity.

U.S. Pat. No. 3,982,016, the disclosure of which is incorporated herein by reference, discloses 16-aryl-13,14-dihydro-PGE$_2$ p-biphenyl esters useful for bone formation activity.

U.S. Pat. No. 4,621,100, the disclosure of which is incorporated herein by reference, discloses substituted cyclopentanes useful for bone formation activity.

U.S. Pat. No. 5,216,183, the disclosure of which is incorporated herein by reference, discloses cyclopentanones useful for bone formation activity.

Sodium fluoride may be used as the second compound of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478, the disclosure of which is incorporated herein by reference. The activity of sodium fluoride is readily determined by those skilled in the art according to biological protocols (e.g., see Eriksen E. F. et al., *Bone Histomorphometry*, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296).

Any parathyroid hormone (PTH) may be used as the second compound of this invention. The term parathyroid hormone refers to parathyroid hormone, fragments or metabolites thereof and structural analogs thereof which can stimulate bone formation and increase bone mass. Also included are parathyroid hormone related peptides and active fragments and analogues of parathyroid related peptides see PCT publication no. WO 94101460. Such bone anabolic functional activity is readily determined by those skilled in the art according to standard assays (e.g., see Eriksen E. F. et al., Bone Histomorphometry, Raven Press, New York, 1994, pages 1–74; Grier S. J. et al., The Use of Dual-Energy X-Ray Absorptiometry In Animals, Inv. Radiol., 1996, 31(1):50–62; Wahner H. W,. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below, however, other parathyroid hormones will be known to those skilled in the art.

Exemplary parathyroid hormones are disclosed in the following references.

"Human Parathyroid Peptide Treatment of Vertebral Osteoporosis", Osteoporosis Int., 3, (Supp 1):199–203.

"PTH 1-34 Treatment of Osteoporosis with Added Hormone Replacement Therapy: Biochemical, Kinetic and Histological Responses" Osteoporosis Int. 1:162–170.

Any growth hormone or growth hormone secretagogue may be used as the second compound of this invention. The term growth hormone secretagogue refers to a compound which stimulates the release of growth hormone or mimics the action of growth hormone (e.g., increases bone formation leading to increased bone mass). Such actions are readily determined by those skilled in the art according to standard assays well known to those of skill in the art A variety of these compounds are disclosed in the following published PCT patent applications: WO 95/14666; WO 95/13069; WO 94/19367; WO 94/13696; and WO 95/34311. However, other growth hormone or growth hormone secretagogues will be known to those skilled in the art.

In particular a preferred growth hormone secretagogue is N-[1-(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-677.

Other preferred growth hormone secretagogues include 2-amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide or its L-tartaric acid salt;

2-amino-N-{1-(R)-benzyloxymethyl-2-[3a-(R)-(4-fluoro-benzyl)-2-methyl-3-oxo-2,3,3a,4,6,7-hexahydro-pyrazolo[4,3-c]pyridin-5-yl]-2-oxo-ethyl}isobutyramide;

2-amino-N-[2-(3a-(R)-benzyl-3-oxo-2,3,3a,4,6,7-hexahydro-pyrazolo[4,3-c]pyridin-5-yl)-1-(R) benzyloxymethyl-2-oxo-ethyl]isobutyramide; and 2-amino-N-1-(2,4-difluoro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4,3-c]pyridin-5-yl-ethyl}2-methyl-propionamide.

Some of the preparation methods useful for the preparation of the compounds described herein may require protection of remote functionality (e.g., primary amine, secondary amine, carboxyl in Formula I or Formula I$^A$ precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

The starting materials and reagents for the above described compounds are also readily available or can be easily synthesized by those skilled in the art using conventional methods of organic synthesis. For example, many of the compounds used herein are related to, or are derived from, compounds found in nature, in which there is a large scientific interest and commercial need, and accordingly many such compounds are commercially available or are reported in the literature or are easily prepared from other commonly available substances by methods which are reported in the literature. Such compounds include, for example, prostaglandins.

All of the compounds of this invention have at least one asymmetric carbon atom and therefore are enantiomers or diastereomers. Diasteromeric mixtures can be separated into their individual diastereomers on the basis of their physical chemical differences by methods known per se, for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing, including both chemical hydrolysis methods and microbial lipase hydrolysis methods, e.g., enzyme catalyzed hydrolysis) the individual diastereomers to the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

Many of the compounds of this invention, including the compounds of Formulas I and $I^A$, the anti-resorptive agents, bone anabolic agents, prostagiandin agonists/antagonists, parathyroid hormones, growth hormones and growth hormone secretagogues, are acidic and they form a salt with a pharmaceutically acceptable cation. Some of the compounds of this invention, including the compounds of Formulas I and $I^A$, the anti-resorptive agents, bone anabolic agents, prostaglandin agonists/antagonists, parathyroid hormones, growth hormones and growth hormone secretagogues, are basic and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention, including the compounds of Formulas I and $I^A$, the anti-resorptive agents, bone anabolic agents, prostaglandin agonists/antagonists, parathyroid hormones, growth hormones and growth hormone secretagogues, form hydrates or solvates they are also within the scope of the invention.

In addition, all prodrugs of the compounds of this invention, including the compounds of Formulas I and $I^A$, the anti-resorptive agents, bone anabolic agents, prostaglandin agonists/antagonists, parathyroid hormones, growth hormones and growth hormone secretagogues, are within the scope of this invention.

The compounds of this invention are all adapted to therapeutic use as agents that stimulate bone formation and increase bone mass in vertebrates, e.g., mammals, and particularly humans. Since bone formation is closely related to the development of osteoporosis and bone related disorders, these compounds, by virtue of their action on bone, prevent, arrest and/or regress osteoporosis.

The utility of the compounds of the present invention as medical agents in the treatment of conditions which present with low bone mass (e.g., osteoporosis) in vertebrates, e.g., mammals (e.g. humans, particularly the female) is demonstrated by the activity of the compounds of this invention in conventional assays, including the in vivo assay, a receptor binding assay, the cyclic AMP assay and the fracture healing assay (all of which are described below). The in vivo assay (with appropriate modifications within the skill in the art) may be used to determine the activity of other anabolic agents as well as the prostaglandin agonists of this invention. The estrogen agonist/antagonist protocol may be used to determine the activity of estrogen agonists/antagonists in particular and also other anti-resorptive agents (with appropriate modifications within the skill in the art). The combination and sequential treatment protocol described below is useful for demonstrating the utility of the combinations of the anabolic agents (e.g., the compounds of this invention) and anti-resorptive agents (e.g., estrogen agonists/antagonists) described herein. Such assays also provide a means whereby the activities of the compounds of this invention (or the other anabolic agents and anti-resorptive agents described herein) can be compared to each other and with the activities of other known compounds. The results of these comparisons are useful for determining dosage levels in vertebrates, e.g., mammals, including humans, for the treatment of such diseases.

Anabolic Agent in Vivo Assay

The activity of anabolic bone agents in stimulating bone formation and increasing bone mass can be tested in intact male or female rats, sex hormone deficient male (orchidectomy) or female (ovariectomy) rats.

Male or female rats at different ages (such as 3 months of age) can be used in the study. The rats are either intact or castrated (ovariectomized or orchidectomized), and subcutaneously injected or gavaged with $EP_2$ agonists at different doses (such as 1, 3, or 10 mg/kg/day) for 30 days. In the castrated rats, treatment is started at the next day after surgery (for the purpose of preventing bone loss) or at the time bone loss has already occured (for the purpose of restoring bone mass). During the study, all rats are allowed free access to water and a pelleted commercial diet (Teklad Rodent Diet #8064, Harlan Teklad, Madison, Wis.) containing 1.46% calcium, 0.99% phosphorus and 4.96 IU/g of Vitamin $D_3$. All rats are given subcutaneous injections of 10 mg/kg calcein on days 12 and 2 before sacrifice. The rats are sacrificed. The following endpoints are determined:

Femoral Bone Mineral Measurements

The right femur from each rat is removed at autopsy and scanned using dual energy X-ray absorptiometry (DXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

Tibial Bone Histomorphometric Analyses

The right tibia is removed at autopsy, dissected free of muscle, and cut into three parts. The proximal tibia and the tibial shaft are fixed in 70% ethanol, dehydrated in graded concentrations of ethanol, defatted in acetone, then embedded in methyl methacrylate (Eastman Organic Chemicals, Rochester, N.Y.).

Frontal sections of proximal tibial metaphyses at 4 and 10 μm thickness are cut using a Reichert-Jung Polycut S microtome. The 4 μm sections are stained with modified Masson's Trichrome stain while the 10 μm sections remained unstained. One 4 μm and one 10 μm sections from each rat are used for cancellous bone histomorphometry.

Cross sections of tibial shaft at 10 μm thickness are cut using a Reichert-Jung Polycut S microtome. These sections are used for cortical bone histomorphometric analysis.

Cancellous bone histomorphometry: A Bioquant OS/2 histomorphometry system (R&M Biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region needs to be omitted in order to restrict measurements to the secondary spongiosa. The 4 μm sections are used to determine indices related to bone volume, bone structure, and bone resorption, while the 10 μm sections are used to determine indices related to bone formation and bone turnover.

I) Measurements and calculations related to trabecular bone volume and structure: (1) Total metaphyseal area (TV, mm$^2$): metaphyseal area between 1.2 and 3.6 mm distal to the growth plate-epiphyseal junction. (2) Trabecular bone area (BV, mm$^2$): total area of trabeculae within TV. (3) Trabecular bone perimeter (BS, mm): the length of total perimeter of trabeculae. (4) Trabecular bone volume (BV/TV, %): BV/TV×100. (5) Trabecular bone number (TBN, #/mm): 1.199/2×BS/TV. (6) Trabecular bone thickness (TBT, μm): (2000/1.199)×(BV/BS). (7) Trabecular bone separation (TBS, μm): (2000×1.199)×(TV−BV).

II) Measurements and calculations related to bone resorption: (1) Osteocdast number (OCN, #): total number of osteoclast within total metaphyseal area. (2) Osteoclast perimeter (OCP, mm): length of trabecular perimeter covered by osteoclast. (3) Osteoclast number/mm (OCN/mm, #/mm): OCN/BS. (4) Percent osteoclast perimeter (%OCP, %): OCP/BS×100.

III) Measurements and calculations related to bone formation and turnover: (1) Single-calcein labeled perimeter (SLS, mm): total length of trabecular perimeter labeled with one calcein label. (2) Double-calcein labeled perimeter (DLS, mm): total length of trabecular perimeter labeled with two calcein labels. (3) Inter-labeled width (ILW, μm): average distance between two calcein labels. (4) Percent mineralizing perimeter (PMS, %): (SLS/2+DLS)/BS×100. (5) Mineral apposition rate (MAR, μm/day): ILW/label interval. (6) Bone formation rate/surface ref. (BFR/BS, μm$^2$/d/ μm): (SLS/2+DLS)×MAR/BS. (7) Bone turnover rate (BTR, %/y): (SLS/2+DLS)×MAR/BV×100.

Cortical bone histomorphometry: A Bioquant OS/2 histomorphometry system (R&M Biometrics, Inc., Nashville, Tenn.) is used for the static and dynamic histomorphometric measurements of tibial shaft cortical bone. Total tissue area, marrow cavity area, periosteal perimeter, endocortical perimeter, single labeled perimeter, double labeled perimeter, and interlabeled width on both periosteal and endocortical surface are measured, and cortical bone area (total tissue area marrow cavity area), percent cortical bone area (cortical area/total tissue area×100), percent marrow area (marrow cavity area/total tissue area×100), periosteal and endocortical percent labeled perimeter [(single labeled perimeter/2+double labeled perimeter)/total perimeter× 100], mineral apposition rate (interlabeled width/intervals), and bone formation rate [mineral apposition rate×[(single labeled perimeter/2+double labeled perimeter)/total perimeter] are calculated.

Statistics

Statistics can be calculated using StatView 4.0 packages (Abacus Concepts, Inc., Berkeley, Calif.). The analysis of variance (ANOVA) test followed by Fisher's PLSD (Stat View, Abacus Concepts Inc., 1918 Bonita Ave, Berkeley, Calif. 94704–1014) are used to compare the differences between groups.

Determination of cAMP Elevation in 293-S Cell Lines Stably Overexpressing Recombinant Human EP$_2$ and EP$_4$ Receptors cDNAs representing the complete open reading frames of the human EP$_2$ and EP$_2$ receptors are generated by reverse transcriptase polymerase chain reaction using oligonucleotide primers based on published sequences (1,2) and RNA from primary human kidney cells (EP$_2$) or primary human lung cells (EP$_4$) as templates. cDNAs are cloned into the multiple cloning site of pcDNA3 (Invitrogen Corporation, 3985B Sorrento Valley Blvd., San Diego, Calif. 92121) and used to transfect 293-S human embryonic kidney cells via calcium phosphate co-precipitation. G418-resistant colonies are expanded and tested for specific [$^3$H]PGE$_2$ binding. Transfectants demonstrating high levels of specific [$^3$H] PGE$_2$ binding are further characterized by Scatchard analysis to determine Bmax and Kds for PGE$_2$. The lines selected for compound screening have approximately 338,400 receptors per cell and a Kd=12 nM for PGE$_2$ (EP$_2$), and approximately 256,400 receptors per cell and a Kd=2.9 nM for PGE$_2$ (EP$_4$). Constituitive expression of both receptors in parental 293-S cells is negligible. Cells are maintained in RPMI supplemented with fetal bovine serum (10% final) and G418 (700 ug/ml final).

cAMP responses in the 293-S/EP$_2$ and 293-S/EP$_4$ lines are determined by detaching cells from culture flasks in 1 ml of Ca++ and Mg++ deficient PBS via vigorous pounding, adding serum-free RPMI to a final concentration of 1×10$^6$ cells/ml, and adding 3-isobutyl-1-methylxanthine (IBMX) to a final concentration of 1 mM. One milliliter of cell suspension is immediately aliquoted into individual 2 ml screwcap microcentrifuge and incubated for 10 minutes, uncovered, at 37° C., 5% CO$_2$, 95% relative humidity. The compound to be tested is then added to cells at 1:100 dilutions such that final DMSO or ethanol concentrations is 1%. Immediately after adding compound, the tubes are covered, mixed by inverting two times, and incubated at 37° C. for 12 minutes. Samples are then lysed by incubation at 100° C. for 10 minutes and immediately cooled on ice for 5 minutes. Cellular debris is pelleted by centrifugation at 1000×g for 5 minutes, and cleared lysates are transferred to fresh tubes. cAMP concentrations are determined using a commercially available cAMP radioimmunoassay kit RIA (NEK-033, DuPont/NEN Research Products, 549 Albany St., Boston, Mass. 02118) after diluting cleared lysates 1:10 in cAMP RIA assay buffer (included in kit). Typically, one treats cells with 6–8 concentrations of the compound to be tested in 1 log increments. EC50 calculations are performed on a calculator using linear regression analysis on the linear portion of the dose response curves.

References

1. Regan, J. W. Bailey, T. J. Pepperl, D. J. Pierce, K. L. Bogardus, A. M. Donello, J. E. Fairbaim, C. E. Kedzie, K. M. Woodward, D. F. and Gil, D. W. 1994 Cloning of a Novel Human Prostaglandin Receptor with Characteristics of the Pharmaclogically Defined EP$_2$ Subtype. Mol. Pharmacology 46:213–220.

2. Bastien, L., Sawyer, N., Grygorczyk, R., Metters, K., and Adam, M. 1994 Cloning, Functional Expression, and Characterization of the Human Prostaglandin E2 Receptor EP2 Subtype. J. Biol. Chem. Vol 269, 16:11873–11877.

Assay for Binding to Prostaglandin E2 Receptors

Membrane Preparation: All operations are performed at 4° C. Transfected cells expressing prostaglandin E$_2$ type 1 receptors (EP$_1$), type 2 (EP$_2$), type 3 (EP$_3$) or type 4 (EP$_4$) receptors are harvested and suspended to 2 million cells per ml in Buffer A [50 mM Tris-HCl (pH 7.4), 10 mM MgCl$_2$, 1 mM EDTA, 1 mM Pefabloc peptide, (Sigma, St. Louis, Mo.), 10 uM Phosporamidon peptide, (Sigma, St. Louis, Mo.), 1 uM pepstatin A peptide, (Sigma, St. Louis, Mo.), 10 μM elastatinal peptide, (Sigma, St. Louis, Mo.), 100 uM antipain peptide, (Sigma, St. Louis, Mo.)]. These are lysed by sonification with a Branson Sonifier (Model #250, Branson Ultrasonics Corporation, Danbury, Conn.) in 2 fifteen second bursts. Unlysed cells and debris are removed by centrifugation at 100×g for 10 min. Membranes are then harvested by centrifugation at 45,000×g for 30 minutes. Pelleted membranes are resuspended to 3–10 mg protein per ml, protein concentration being determined according to the method of Bradford [Bradford, M., Anal. Biochem., 72, 248 (1976)]. Resuspended membranes are then stored frozen at −80° C. until use.

Binding Assay: Frozen membranes prepared as above are thawed and diluted to 1 mg protein per ml in Buffer A above. One volume of membrane preparation is combined with 0.05 volume test compound or buffer and one volume of 3 nM 3H-prostaglandin $E_2$ (#TRK 431, Amersham, Arlington Heights, Ill.) in Buffer A. The mixture (205 μL total volume) is incubated for 1 hour at 25° C. The membranes are then recovered by filtration through type GF/C glass fiber filters (#1205–401, Wallac, Gaithersburg, Md.) using a Tomtec harvester (Model Mach II/96, Tomtec, Orange, Conn.). The membranes with bound $^3$H-prostaglandin $E_2$ are trapped by the filter, while the buffer and unbound $^3$H-prostaglandin $E_2$ pass through the filter into waste. Each sample is then washed 3 times with 3 ml of [50 mM Tris-HCl (pH 7.4), 10 mM $MgCl_2$, 1 mM EDTA]. The filters are then dried by heating in a microwave oven. To determine the amount of $^3$H-prostaglandin bound to the membranes, the dried filters are placed into plastic bags with scintillation fluid and counted in a LKB 1205 Betaplate reader (Wallac, Gaithersburg, Md.). IC50s are determined from the concentration of test compound required to displace 50% of the specifically bound $^3$H-prostaglandin $E_2$.

Fracture Healing Assays Assays for Effects on Fracture Healing after Systemic Administration Fracture Technique: Sprage-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and vertebrates with fractures outside the specified diaphyseal area or with displaced nails are excluded. The remaining animals are divided randomly into the following groups with 10–12 animals per each subgroup per time point for testing the fracture healing. The first group receives daily gavage of vehicle (water: 100% Ethnanol=95:5) at 1 ml/rat, while the others receive daily gavage from 0.01 to 100 mg/kg/day of the compound to be tested (1 ml/rat) for 10, 20, 40 and 80 days.

At 10, 20, 40 and 80 days, 10–12 rats from each group are anesthetized with Ketamine and autopsied by exsanguination. Both tibiofibular bones are removed by dissection and all soft tissue is stripped. Bones from 5–6 rats for each group are stored in 70% ethanol for histological analysis, and bones from another 5–6 rats for each group are stored in a buffered Ringers solution (+4° C., pH 7.4) for radiographs and biomechanical testing which is performed.

Histological Analysis: The methods for histologic analysis of fractured bone have been previously published by Mosekilde and Bak (The Effects of Growth Hormone on Fracture Healing in Rats: A Histological Description. Bone, 14:19–27, 1993). Briefly, the fracture side is sawed 8 mm to each side of the fracture line, embedded undecalcified in methymethacrylate, and cut frontals sections on a Reichert-Jung Polycut microtome in 8 μm thick. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297, 1989). Briefly, radiographs of all fractures are taken prior to the biomechanical test The mechanical properties of the healing fractures are analyzed by a destructive three- or four-point bending procedure. Maximum load, stiffness, energy at maximum load, deflection at maximum load, and maximum stress are determined.

Assay for Effects on Fracture Healing After Local Administration

Fracture Technique: Female or male beagle dogs at approximately 2 years of age are used in the study. Transyerse radial fractures are produced by slow continuous loading in three-point bending as described by Lenehan et al. (Lenehan, T. M.; Balligand, M.; Nunamaker, D. M.; Wood, F. E.: Effects of EHDP on Fracture Healing in Dogs. J Orthop Res 3:499–507; 1985). The wire is pulled through the fracture site to ensure complete anatomical disruption of the bone. Thereafter, local delivery of $EP_2$ agonists to the fracture site is achieved by slow release of compound delivered by slow release pellets or by administration of the compounds in a suitable formulation such as a paste gel solution or suspension for 10, 15, or 20 weeks.

Histological Analysis: The methods for histologic analysis of fractured bone have been previously published by Peter et al. (Peter, C. P.; Cook, W. O.; Nunamaker, D. M.; Provost, M. T.; Seedor, J. G.; Rodan, G. A. Effects of alendronate on fracture healing and bone remodeling in dogs. J. Orthop. Res. 14:74–70, 1996) and Mosekilde and Bak (The Effects of Growth Hormone on Fracture Healing in Rats: A Histological Description. Bone, 14:19–27, 1993). Briefly, the fracture side is sawed 3 cm to each side of the fracture line, embedded undecalcified in methymethacrylate, and cut on a Reichert-Jung Polycut microtome in 8 μm thick of frontal sections. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap-measured as the shortest distance between the cortical bone ends in the fracture, (2) callus length and callus diameter, (3) total bone volume area of callus, (4) bony tissue per,tissue area inside the callus area, (5) fibrous tissue in the callus, (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297, 1989) and Peter et al. (Peter, C. P.; Cook, W. O.; Nunamaker, D. M.; Provost, M. T.; Seedor, J. G.; Rodan, G. A. Effects of Alendronate On Fracture Healing And Bone Remodeling In Dogs. J. Orthop. Res. 14:74–70, 1996). Briefly, radiographs of all fractures are taken prior to the biomechanical test. The mechanical properties of the healing fractures are analyzed by a destructive three- or four-point bending procedures. Maximum load, stiffness, energy at maximum load, deflection at maximum load, and maximum stress are determined.

Estrogen Agonist/Antagonist Protocol

Estrogen agonist/antagonists are a class of compounds which inhibit bone turnover and prevent estrogen-deficiency induced bone loss. The ovariectomized rat bone loss model has been widely used as a model of post-menopausal bone loss. Using this model, one can test the efficacy of the estrogen agonist/antagonist compounds in preventing bone loss and inhibiting bone resorption.

Sprague-Dawley female rats (Charles River, Wilmington, Mass.) at different ages (such as 5 months of age) are used in these studies. The rats are singly housed in 20 cm×32 cm×20 cm cages during the experimental period. All rats are allowed free access to water and a pelleted commercial diet (Agway ProLab 3000, Agway County Food, Inc., Syracuse, N.Y.) containing 0.97% calcium, 0.85% phosphorus, and 1.05 IU/g of Vitamin $D_3$.

A group of rats (8 to 10) are sham-operated and treated p.o. with vehicle (10% ethanol and 90% saline, 1 ml/day), while the remaining rats are bilaterally ovariectomized (OVX) and treated with either vehicle (p.o.), 17β-estradiol (Sigma, E-8876, $E_2$, 30 μg/kg, daily subcutaneous injection), or estrogen agonist/antagonists (such as droloxifene at 5, 10, or 20 mg/kg, daily p.o.) for a certain period (such as 4 weeks). All rats are given subcutaneous injections of 10 mg/kg calcein (fluorochrome bone marker) 12 and 2 days before being sacrificed in order to examine the dynamic changes in bone tissue. After 4 weeks of treatment, the rats are sacrificed and autopsied. The following endpoints are, determined:

Body Weight Gain: Body weight at autopsy minus body weight at surgery.

Uterine Weight and Histology: The uterus is removed from each rat during autopsy, and weighed immediately. Thereafter, the uterus is processed for histologic measurements such as uterine cross-sectional tissue area, stromal thickness, and luminal epithelial thickness.

Total Serum Cholesterol: Blood is obtained by cardiac puncture and allowed to clot at 4° C., and then centrifuged at 2,000 g for 10 min. Serum samples are analyzed for total serum cholesterol using a high performance cholesterol calorimetric assay (Boehringer Mannheim Biochemicals, Indianapolis, Ind.).

Femoral Bone Mineral Measurements: The right femur from each rat is removed at autopsy and scanned using dual energy X-ray absorptiometry (DEXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) is determined.

Proximal Tibial Metaphyseal Cancellous Bone Histomorphometric Analyses: The right tibia is removed at autopsy, dissected free of muscle, and cut into three parts. The proximal tibia is fixed in 70% ethanol, dehydrated in graded concentrations of ethanol, defatted in acetone, then embedded in methyl methacrylate (Eastman Organic Chemicals, Rochester, N.Y.). Frontal sections of proximal tibial metaphyses at 4 and 10 μm thickness are cut using a Reichert-Jung Polycut S microtome. One 4 μm and one 10 μm sections from each rat are used for cancellous bone histomorphometry. The 4 μm sections are stained with modified Masson's Trichrome stain while the 10 μm sections remained unstained.

A Bioquant OS/2 histomorphometry system (R&M Biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region is omitted in order to restrict measurements to the secondary spongiosa. The 4 μm sections are used to determine indices related to bone volume, bone structure, and bone resorption, while the 10 μm sections are used to determine indices related to bone formation and bone turnover.

I. Measurements and Calculations Related to Trabecular Bone Volume and Structure 1. Total metaphyseal area (TV, $mm^2$): metaphyseal area between 1.2 and 3.6 mm distal to the growth plate-epiphyseal junction.
2. Trabecular bone area (BV, $mm^2$): total area of trabeculae within TV.
3. Trabecular bone perimeter (BS, mm): the length of total perimeter of trabeculae.
4. Trabecular bone volume (BV/TV, %): BV/TV×100.
5. Trabecular bone number (TBN, #/mm): 1.199/2×BS/TV.
6. Trabecular bone thickness (TBT, μm): (2000/1.199)×(BV/BS).
7. Trabecular bone separation (TBS, μm): (2000×1.199)×(TV−BV).

II. Measurements and Calculations Related to Bone Resorption

1. Osteoclast number (OCN, #): total number of osteoclast within total metaphyseal area.
2. Osteoclast perimeter (OCP, mm): length of trabecular perimeter covered by osteoclast.
3. Osteoclast number/mm (OCN/mm, #/mm): OCN/BS.
4. Percent osteoclast perimeter (%OCP, %): OCP/BS×100.

III. Measurements and Calculations Related to Bone Formation and Turnover

1. Single-calcein labeled perimeter (SLS, mm): total length of trabecular perimeter labeled with one calcein label.
2. Double-calcein labeled perimeter (DLS, mm): total length of trabecular perimeter labeled with two calcein labels.
3. Inter-labeled width (ILW, μm): average distance between two calcein labels.

4. Percent mineralizing perimeter (PMS, %): (SLS/2+DLS)/BS×100.

5. Mineral apposition rate (MAR, μm/day): ILW/label interval.

6. Bone formation rate/surface ref. (BFR/BS, μm²/d/μm): (SLS/2+DLS)×MAR/BS.

7. Bone turnover rate (BTR, %/y): (SLS/2+DLS)×MAR/BV×100.

Statistics

Statistics are calculated using StatView 4.0 packages (Abacus Concepts, Inc., Berkeley, Calif.). The analysis of variance (ANOVA) test followed by Fisher's PLSD (Stat View, Abacus Concepts Inc. 1918 Bonita Ave, Berkeley, Calif. 94704-1014) is used to compare the differences between groups.

Combination and Sequential Treatment Protocol

The following protocols can of course be varied by those skilled in the art. For example, intact male or female rats, sex hormone deficient male (orchidectomy) or female (ovariectomy) rats may be used. In addition, male or female rats at different ages (such as 12 months of age) can be used in the studies. The rats can be either intact or castrated (ovariectomized or orchidectomized), and administrated with anabolic agents such as the compounds of this invention at different doses (such as 1, 3 or 6 mg/kg/day) for a certain period (such as two weeks to two months), and followed by administration of an anti-resorptive agent such as droloxifene at different doses (such as 1,5,10 mg/kg/day) for a certain period (such as two weeks to two months), or a combination treatment with both anabolic agent and anti-resorptive agent at different doses for a certain period (such as two weeks to two months). In the castrated rats, treatment can be started at the next day after surgery (for the purpose of preventing bone loss) or at the time bone loss has already occurred (for the purpose of restoring bone mass).

The rats are sacrificed under ketamine anesthesia. The following endpoints are determined:

Femoral bone mineral measurements are performed as described above in the estrogen agonist/antagonist protocol.

Lumbar Vertebral Bone Mineral Measurements: Dual energy X-ray absorptiometry (QDR 1000/W, Hologic, Inc., Waltham, Mass.) equipped with a "Regional High Resolution Scan" software (Hologic, Inc., Waltham, Mass.) is used to determined the bone area, bone mineral content (BMC), and bone mineral density (BMD) of whole lumbar spine and each of the six lumbar vertebrae (LV1–6) in the anesthetized rats. The rats are anesthetized by injection (i.p.) of 1 ml/kg of a mixture of ketamine/rompun (ratio of 4 to 3), and then placed on a rat platform. The scan field sized is 6×1.9 cm, resolution is 0.0254×0.0127 cm, and scan speed is 7.25 mm/sec. The whole lumbar spine scan image is obtained and analyzed. Bone area (BA), and bone mineral content (BMC) is determined, and bone mineral density is calculated (MBC divided by BA) for the whole lumbar spine and each of the six lumbar vertebrae (LV1–6).

Proximal tibial metaphyseal cancellous bone histomorphometric analyses are performed as described above for in the estrogen agonist/antagonist protocol.

Measurements and calculations related to trabecular bone volume and structure are performed as described above in the estrogen agonist/antagonist protocol. Further, measurements and calculations related to bone resorption are also performed as described above in the estrogen agonist/antagonist protocol. Still further, measurements and calculations related to bone formation and turnover are performed as described above in the estrogen agonist/antagonist protocol. Further still, the data obtained is analyzed using the statistical manipulations described above in the estrogen agonist/antagonist protocol.

Kidney Regeneration Assay

The role of an prostaglandin selective agonist in kidney regeneration is investigated by the ability of Prostaglandin $E_2$ ($PGE_2$) or a selective prostaglandin agonist to induce the expression of Bone Morphogenetic Protein 7 (BMP-7) in wild type 293S cells and in 293S cells transfected with $EP_2$.

Methods: 293S and $EP_2$ 293S cells are grown in Dulbecco's Modified Egale medium (DMEM, Gibco, BRL; Gaithersburg, Md.). One day prior to treatment with $PGE_2$ or an prostaglandin agonist, cells are plated at a density of $1.5 \times 10^6$ cells/10 cm dish. Generally about 16 to 24 hours later the cell monolayer is washed once with OptiMEM (Gico, BRL) followed by the addition of 10 ml OptiMEM/dish in the presence and absense of vehicle (DMSO), $PGE_2$ ($10^{-6}$M) or an prostaglandin selective agonist ($10^{-6}$M). Cells are harvested and RNA is extracted at 8, 16 and 24 hours. Northern blot analysis of total (20 mg/lane) is carried out by probing the blots with $^{32}$P-labeled BMP-7 probe. The blots are normalized for RNA loading by hybridization with $^{32}$P-labeled 18s ribosomal RNA probe. $PGE_2$ and prostaglandin selective agonists induce the expression of BMP-7 in the $EP_2$ 293S cells in a time dependent manner. Such induction of expression is generally not observed in the parental cell line. Given the known role of BMP-7 in kidney regeneration and the ability of an prostaglandin agonist to induce BMP-7 expression in 293S kidney cells in a time and receptor specific manner indicates a role for prostaglandin agonist in kidney regeneration.

Administration of the compounds of this invention can be via any method which delivers a compound of this invention systemically and/or locally (e.g., at the site of the bone fracture, osteotomy, or orthopedic surgery). These methods include oral routes, parenteral, intraduodenal routes, etc. Generally, the compounds of this invention are administered orally, but parenteral administration (e.g., intravenous, intramuscular, transdermal, subcutaneous, rectal or intramedullary) may be utilized, for example, where oral administration is inappropriate for the target or where the patient is unable to ingest the drug.

The compounds are used for the treatment and promotion of healing of bone fractures and osteotomies by the local application (e.g., to the sites of bone fractures of osteotomies) of the compounds of this invention or compositions thereof. The compounds of this invention are applied to the sites of bone fractures or osteotomies, for example, either by injection of the compound in a suitable solvent (e.g., an oily solvent such as arachis oil) to the cartilage growth plate or, in cases of open surgery, by local application thereto of such compounds in a suitable carrier such as bone-wax, demineralized bone powder, polymeric bone cements, bone sealants, etc. Alternatively, local application can be achieved by applying a solution or dispersion of the compound in a suitable carrier onto the surface of, or incorporating it into solid or semi-solid implants conventionally used in orthopedic surgery, such as dacron-mesh, gel-foam and kiel bone, or prostheses.

The compounds of this invention may also be applied locally to the site of the fracture or osteotomy in a suitable carrier in combination with one or more of the anabolic agents or bone anti-resorptive agents described above.

Such combinations within the scope of this invention can be co-administered simultaneously or sequentially in any order, or a single pharmaceutical composition comprising a Formula I compound, a prodrug thereof or a pharmaceutical salt of said compound or said prodrug as described above and a second compound as described above in a pharmaceutically acceptable carrier can be administered.

For example, a bone anabolic agent can be used in this invention alone or in combination with an anti-resorptive agent for three months to three years, followed by an anti-resorptive agent alone for three months to three years, with optional repeat of the full treatment cycle. Alternatively, for example, the bone anabolic agent can be used alone or in combination with an anti-resorptive agent for three months to three years, followed by an anti-resorptive agent alone for the remainder of the patient's life. For example, in one preferred mode of administration, a Formula I or Formula $I^A$ compound, or a prodrug thereof or a pharmaceutically acceptable salt of said compound or said prodrug as described above may be administered once daily and a second compound as described above (e.g., estrogen agonist/antagonist) may be administered daily in single or multiple doses. Alternatively, for example, in another preferred mode of administration the two compounds may be administered sequentially wherein the Formula I or Formula $I^A$ compound, prodrug thereof or pharmaceutically acceptable salt of said compound or said prodrug as described above may be administered once daily for a period of time sufficient to augment bone mass to a level which is above the bone fracture threshold (World Health Organization Study "Assessment of Fracture Risk and its Application to Screening for Postmenopausal Osteoporosis (1994). Report of a World Health Organization Study Group. World Health Organization Technical Series 843") followed by administration of a second compound, as described above (e.g., estrogen agonist/antagonist), daily in single or multiple doses. It is preferred that the first compound as described above is administered once daily in a rapid delivery form such as oral delivery.

In any event, the amount and timing of compounds administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the treatment (e.g., bone mass augmentation) that the physician considers appropriate for the patient. In considering the degree of treatment desired, the physician must balance a variety of factors such as bone mass starting level, age of the patient, presence of preexisting disease, as well as presence of other diseases (e.g., cardiovascular disease).

In general an amount of a compound of this invention is used that is sufficient to augment bone mass to a level which is above the bone fracture threshold (as detailed in the World Health Organization Study previously cited herein).

In general an effective dosage for the anabolic agents used in this invention described above is in the range of 0.001 to 100 mg/kg/day, preferably 0.01 to 50 mg/kg/day.

The following paragraphs provide preferred dosage ranges for various anti-resorptive agents.

The amount of the anti-resorptive agent to be used is determined by its activity as a bone loss inhibiting agent. This activity is determined by means of the pharmacokinetics of an individual compound and its minimal versus maximal effective dose in inhibition of bone loss using a protocol such as described above (e.g., Estrogen Agonist/Antagonist Protocol).

In general, an effective dosage for an anti-resorptive agent is about 0.001 mg/kg/day to about 20 mg/kg/day.

In general, an effective dosage for progestins is about 0.1 to 10 mg per day: the preferred dose is about 0.25 to 5 mg per day.

In general, an effective dosage for polyphosphonates is determined by its potency as a bone resorption inhibiting agent according to standard assays.

Ranges for the daily administration of some polyphosphonates are about 0.001 mg/kg/day to about 20 mg/kg/day.

In general an effective dosage for the treatment of this invention, for example the bone resorption treatment of this invention, for the estrogen agonists/antagonists of this invention is in the range of 0.01 to 200 mg/kg/day, preferably 0.5 to 100 mg/kg/day.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day.

In particular, an effective dosage for tamoxifen is in the range of 0.1 to 100 mg/kg/day, preferably 0.1 to 5 mg/kg/day.

In particular, an effective dosage for
cis-6-(4-fluoro-phenyl)-5-[4-(2-piperidin-1-yl-ethoxy)-phenyl]-5,6,7,8-tetrahydro-naphthalene-2-ol;
(−)-cis-6-phenyl-5-(4-(2-pyrrolidin-1-yl-ethoxy)-phenyl]-5,6,7,8-tetrahydro-naphthalene-2-ol;
cis-6-phenyl-5-[4-(2-pyrrolidin-1-yl-ethoxy)-phenyl]-5,6,7,8-tetrahydro-naphthalene-2-ol;
cis-1-[6'-pyrrolodinoethoxy-3'-pyridyl]-2-phenyl-6-hydroxy-1,2,3,4-tetrahydronaphthalene;
1-(4'-pyrrolidinoethoxyphenyl)-2-(4"-fluoro-phenyl)-6-hydroxy-1,2,3,4-tetrahydroisoquinoline;
cis-6-(4-hydroxyphenyl)-5-[4-(2-piperidin-1-yl-ethoxy)-phenyl]-5,6,7,8-tetrahydro-naphthalene-2-ol; or
1-(4'-pyrrolidinolethoxyphenyl)-2-phenyl-6-hydroxy-1,2,3,4-tetrahydroisoquinoline
is in the range of 0.0001 to 100 mg/kg/day, preferably 0.001 to 10 mg/kg/day.

In particular, an effective dosage for 4-hydroxy tamoxifen is in the range of 0.0001 to 100 mg/kg/day, preferably 0.001 to 10 mg/kg/day.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) of this invention in an amount effective to treat the disease/condition of the subject being treated, e.g., a bone disorder.

Since the present invention has an aspect that relates to the augmentation and maintenance of bone mass by treatment with a combination of active ingredients which may be administered separately, the invention also relates to combining separate pharmaceutical compositions in kit form. The kit comprises two separate pharmaceutical compositions: a compound of Formula I or Formula $I^A$, a prodrug thereof or a pharmaceutically acceptable salt of said compound or said prodrug and a second compound as described above. The kit comprises container means for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also a daily dose of a Formula I or Formula $I^A$ compound, a prodrug thereof or a pharmaceutically acceptable salt of said compound or said prodrug can consist of one tablet or capsule while a daily dose of the second compound can consist of several tablets or capsules and vice versa. The memory aid should reflect this.

In another specific embodiment of the invention a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of this invention either alone or in combination with each other or other compounds generally will be administered in a convenient formulation. The following formulation examples only are illustrative and are not intended to limit the scope of the present invention.

In the formulations which follow, "active ingredient" means a compound or compounds of this invention.

Formulation 1: Gelatin Capsules

Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant, cooled to 30° C., and transferred to a filling device. The required amount is then fed to a stainless steel container and diluted with the remaining propellant The valve units are then fitted to the container. Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 20 mg |
| Isotonic saline | 1,000 mL |

The solution of the above ingredients is intravenously administered to a patient at a rate of about 1 mL per minute.

The active ingredient above may also be a combination of agents.

The abbreviations "Me", "Et", "iPr", "Tf", "Bu", "Ph", "EDC" and "Ac", where used herein, define the terms "methyl", ethyl isopropyl", "triflyl", "butyl", "phenyl", "1-(3-dimethylaminopropyl)-3-carbodiimide hydrochloride" and "acetyl", respectively.

General Experimental Procedures

Proton NMR spectra were recorded on a Varian XL-300, Varian UNITY Plus-400, a Varian XL-250 (manufactured by Varian Co., Palo Alto, Calif.) or a Bruker AM-300 spectrometer (Bruker Co., Billerica, Mass.) at about 23° C. Chemical shifts are expressed in parts per million downfield from trimethylsilane. The peak shapes are denoted as follows: s, singlet; d, doublet; t, triplet, q, quartet; m, multiplet; bs=broad singlet. Resonances designated as exchangeable did not appear in a separate NMR experiment where the sample was shaken with several drops of $D_2O$ in the same solvent. Atmospheric pressure chemical ionization (APCI) mass spectra were obtained on a Fisons Platform II Spectrometer. Chemical ionization mass spectra were obtained on a Hewlett-Packard 5989 instrument (Hewlett-Packard Co., Palo Alto, Calif.) (ammonia ionization, particle beam mass spectrometer). Where the intensity of chlorine or bromine-containing ions are described, the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

Column chromatography was performed with either Baker Silica Gel (40 $\mu$m) (J. T. Baker, Phillipsburg, N.J.) or Silica Gel 60 (EM Sciences, Gibbstown, N.J.) in glass columns under low nitrogen pressure. Radial Chromatography was performed using a Chromatatron (model 7924T, Harrison Research, 840 Moana Court, Palo Alto, Calif., 93406). Unless otherwise specified, reagents were used as obtained from commercial sources. Dimethylformamide, 2-propanol, tetrahydrofuran, and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and "coevaporated" refer to removal of solvent at water aspirator pressure on a rotary evaporator with a bath temperature of less than 45° C. Reactions conducted at "0–20° C. " or "0–25° C."were conducted with initial cooling of the vessel in an insulated ice bath which was allowed to warm to room temperature over several hours. The abbreviation "min" and "h" stand for "minutes" and "hours", respectively.

EXAMPLE 1

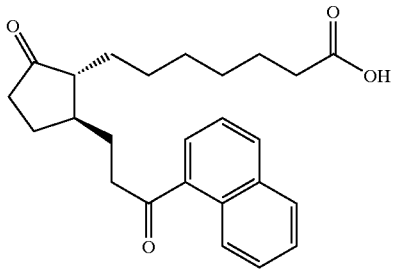

trans-7-[2-(3-Naphthalen-1-yl-3-oxo-propyl)-5-oxo-cyclopentyl]-heptanoic acid

Step A trans-7-[2-(3-Naphthalen-1-yl-3-oxo-propenyl)-5-oxo-cyclopentyl]-heptanoic acid methyl ester. A solution of tetrakis(triphenylphosphine)palladium(0) (97 mg, 0.084 mmol) in dry toluene (10 mL) was evacuated under vacuum and was purged with carbon monoxide (3×). Naphthalene-1-carbonyl chloride (320 mg, 1.68 mmol) was added followed by addition of trans-7-[2-oxo-5-(2-tributylstannanyl-vinyl)-cyclopentyl)-heptanoic acid methyl ester (the compound of Preparation 1, Step D, 1.0 g, 1.85 mmol) and 2,6-di-tert-butyl-4-methylphenol (few crystals). The mixture was heated at 100° C. under an atmosphere of carbon monoxide for 24 h. The mixture was cooled to room temperature, diluted with ethyl acetate, and the insolubles were removed by filtration through a pad of Celite®. The filtrate was washed with 10% aqueous ammonium hydroxide, dried (magnesium sulfate), filtered, and concentrated. Purification by flash chromatography (hexanes to 20% ethyl acetate in hexanes) provided the title compound of Step A (162 mg). $^1$H NMR (CDCl$_3$, 250 MHz) d 8.31 (m, 1H), 8.00 (d, 1H), 7.91 (m, 1H), 7.70 (dd, 1H), 7.55 (m, 3H), 6.91–6.71 (m, 2H), 3.68 (s, 3H), 2.75 (m, 1H), 2.42–2.11 (m, 5H), 2.00 (m, 1H), 1.81–1.20 (m, 9H), 1.94 (t, 2H); MS 407 (M+1), 424 (M+18).

Step B trans-7-[2-(3-Naphthalen-1-yl-3-oxo-propyl)-5-oxo-cyclopentyl]-heptanoic acid methyl ester. A mixture of trans-7-[2-(3-naphthalen-1-yl-3-oxo-propenyl)-5-oxo-cyclopentyl]-heptanoic acid methyl ester of Step A (143 mg, 0.352 mmol), 10% palladium on carbon (100 mg), and ethyl acetate (10 mL) were hydrogenated on a Parr shaker at 50 psi for 1.5 h. The catalyst was removed via filtration through Celite®. The filtrate was concentrated and the residue was purified by radial chromatography (hexanes to 25% ethyl acetate in hexanes) to provide the title compound of Step B (100 mg) as a clear and colorless oil. MS 426 (M+18).

Step C trans-7-[2-(3-Naphthalen-1-yl-3-oxo-propyl)-5-oxo-cyclopentyl]-heptanoic acid. Porcine pancreas lipase (92 mg) was added to a mixture of trans-7-[2-(3-naphthalen-1-yl-3-oxo-propyl)-5-oxo-cyclopentyl]-heptanoic acid methyl ester of Step B (92 mg), pH 7 phosphate buffer solution (Aldrich, 20 mL), and acetone (2 mL). The mixture was stirred at room temperature overnight and the insolubles were removed by filtration through Celite® with the aid of ethyl acetate. The organic solution was dried (magnesium sulfate), filtered, and concentrated. Radial chromatography (CH$_2$–Cl$_2$ to 5% MeOH in CH$_2$–Cl$_2$) provided the title compound of Example 1 (65 mg). $^1$H NMR (CDCl$_3$, 250 MHz) d 8.56 (m, 1H), 8.00 (d, 1H), 7.93 (m, 2H), 7.65 (m, 3H), 3.16 (m, 2H), 2.41–1.25 (m, 20H); MS 412 (M+18).

EXAMPLE 2

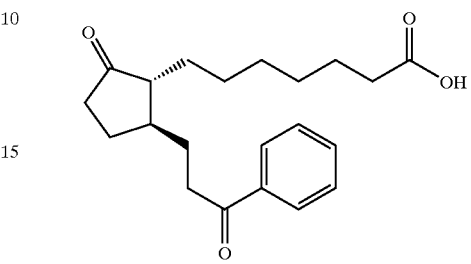

trans-7-[2-Oxo-5-(3-oxo-3-phenyl-propyl)-cyclopentyl]-heptanoic acid

Step A trans-7-[2-Oxo-5-(3-oxo-3-phenyl-propenyl)-cyclopentyl]-heptanoic acid methyl ester. To a solution of benzoyl chloride (0.224 mL, 1.94 mmol) in tetrahydrofuran (20 mL) was added tris(dibenzylideneacetone)dipalladium (0) (Pd$_2$(DBA)$_3$) (8.8 mg, 0.01 mmol) and tri-2-furylphosphine (9.2 mg, 0.04 mmol). The mixture was stirred for 10 minutes and trans-7-[2-oxo-5-(2-tributylstannanyl-vinyl)-cyclopentyl]-heptanoic acid methyl ester (the compound of Preparation 1, Step D, 1.0 g, 1.85 mmol) was added. The reaction was stirred for 24 h and was concentrated in vacuo. Radial chromatography (hexanes to 20% hexanes in ethyl acetate) provided the title compound of Step A as a clear and colorless oil (569 mg). $^1$H NMR (CDCl$_3$, 250 MHz) d 7.94 (m, 2H), 7.62–7.42 (m, 3H), 7.00 (m, 2H), 3.64 (s, 3H), 2.75 (m, 1H), 2.44 (m, 1H), 2.23 (m, 5H), 2.03 (m, 1H), 1.86–1.16 (m, 8H), 0.90 (t, 2H).

Step B trans-7-[2-Oxo-5-(3-oxo-3-phenyl-propyl)-cyclopentyl]-heptanoic acid methyl ester. Following a procedure analogous to that described in Step B of Example 1, trans-7-[2-oxo-5-(3-oxo-3-phenyl-propenyl)-cyclopentyl]-heptanoic acid methyl ester of Step A (569 mg) was hydrogenated to provide the title compound of Step B (286 mg) as a clear and colorless oil. MS 376 (M+18).

Step C trans-7-[2-Oxo-5-(3-oxo-3-phenyl-propyl)-cyclopentyl]-heptanoic acid. Following a procedure analogous to that described in Step C of Example 1, trans-7-[2-oxo-5-(3-oxo-3-phenyl-propyl)-cyclopentyl]-heptanoic acid methyl ester of Step B (182 mg, 0.508 mmol) was hydrolyzed to give the title compound of Example 2 (140 mg). MS 362 (M+18).

EXAMPLE 3

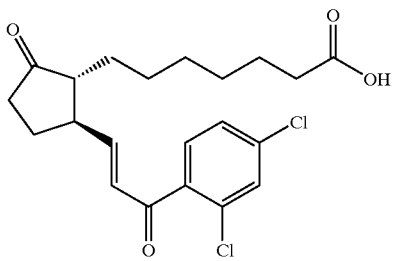

trans-7-{2-[3-(2,4-Dichloro-phenyl)-3-oxo-propenyl]-5-oxo-cyclopentyl}-heptanoic acid

Step A

Wang resin bound trans-7-{2-[3-(2,4-Dichloro-phenyl)-3-oxo-propenyl]-5-oxo-cyclopentyl}-heptanoic acid. Wang resin bound trans-7-[2-oxo-5-(2-tributylstannanyl-vinyl)-cyclopentyl]-heptanoic acid (the compound of Preparation 1, Step F, 70 mg, 0.525 mmol, 1 eq), tris(dibenzylideneacetone)dipalladium(0) (19.2 mg, 0.21 mmol, 0.4 eq) and potassium carbonate (80 mg, 0.577 mmol, 1.1 eq) were distributed in a 96-well plate. To this was added tetrahydrofuran (0.6 mL), diisopropylethylamine (0.09 mL) and 2,4-dichlorobenzoyl chloride (117.6 mg, ~8 eq). The resulting suspension was shaken overnight. The resin was filtered, washed, (N,N-dimethylformamide, methanol, dichloromethane, methanol, and diethyl ether) and oven dried.

Step B trans-7-{2-[3-(2,4-Dichloro-phenyl)-3-oxo-propenyl]-5-oxo-cyclopentyl}-heptanoic acid. Wang resin bound trans-7-{2-[3-(2,4-dichloro-phenyl)-3-oxo-propenyl]-5-oxo-cyclopentyl}-heptanoic acid of Step A (100 mg) was swollen with dichloromethane (about 0.5 mL), and trifluoroacetic acid (about 5 mL) was added. The suspension was stirred for 2 hours, filtered, and washed with dichloromethane and methanol. The solvent was removed under vacuum to afford the title compound of Step B.

Examples 4–65, set forth in Table 1, were prepared using the appropriate starting materials in a manner analogous to procedures set forth in Example 3. Examples 4–65 have the following backbone structure:

TABLE 1

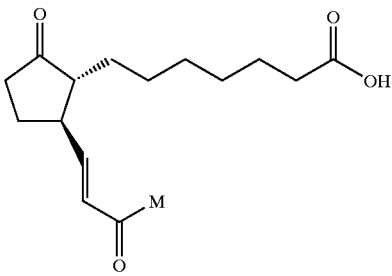

| Example Number | Name | M |
|---|---|---|
| 4 | trans-7-{2-[3-(4-Methoxy-phenyl)-3-oxo-propenyl]-5-oxo-cyclopentyl}-heptanoic acid. | —C6H4—OMe (para) |
| 5 | trans-7-{2-[3-(3,4-Dichloro-phenyl)-3-oxo-propenyl]-5-oxo-cyclopentyl}-heptanoic acid. | 3,4-dichlorophenyl |
| 6 | trans-7-{2-[3-(3,5-Dichloro-phenyl)-3-oxo-propenyl]-5-oxo-cyclopentyl}-heptanoic acid. | 3,5-dichlorophenyl |
| 7 | trans-7-{2-Oxo-5-[3-oxo-3-(2,3,4-trifluoro-phenyl)-propenyl]-cyclopentyl}-heptanoic acid. | 2,3,4-trifluorophenyl |

TABLE 1-continued

[Structure: cyclopentanone with heptanoic acid chain and propenyl-C(=O)-M substituent]

| Example Number | Name | M |
|---|---|---|
| 8 | trans-7-{2-[3-(3,4-Dimethoxy-phenyl)-3-oxo-propenyl]-5-oxo-cyclopentyl}-heptanoic acid. | 3,4-dimethoxyphenyl |
| 9 | trans-7-{2-[3-(2-Chloro-phenyl)-3-oxo-propenyl]-5-oxo-cyclopentyl}-heptanoic acid | 2-chlorophenyl |
| 10 | trans-7-{2-[3-(3-Fluoro-phenyl)-3-oxo-propenyl]-5-oxo-cyclopentyl}-heptanoic acid. | 3-fluorophenyl |
| 11 | trans-7-{2-[3-(5-Chloro-2-nitro-phenyl)-3-oxo-propenyl]-5-oxo-cyclopentyl}-heptanoic acid. | 5-chloro-2-nitrophenyl |
| 12 | trans-7{2-[3-(2-Fluoro-phenyl)-3-oxo-propenyl]-5-oxo-cyclopentyl}-heptanoic acid. | 2-fluorophenyl |
| 13 | trans-7-{2-[3-(2,5-Bis-trifluoromethyl-phenyl)-3-oxo-propenyl]-5-oxo-cyclopentyl}-heptanoic acid | 2,5-bis(trifluoromethyl)phenyl |
| 14 | trans-7-{2-[3-(2,6-Dichloro-phenyl)-3-oxo-propenyl]-5-oxo-cyclopentyl}-heptanoic acid | 2,6-dichlorophenyl |
| 15 | trans-7-{2-[3-(3,5-Bis-trifluoromethyl-phenyl)-3-oxo-propenyl]-5-oxo-cyclopentyl}-heptanoic acid | 3,5-bis(trifluoromethyl)phenyl |

TABLE 1-continued

| Example Number | Name | M |
|---|---|---|
| 16 | trans-7-{2-[3-(2,4-Bis-trifluoromethyl-phenyl)-3-oxo-propenyl]-5-oxo-cyclopentyl}-heptanoic acid | 2,4-bis(trifluoromethyl)phenyl |
| 17 | trans-7-{2-[3-(4-Methyl-3-nitro-phenyl)-3-oxo-propenyl]-5-oxo-cyclopentyl}-heptanoic acid. | 4-methyl-3-nitrophenyl |
| 18 | trans-7-{2-Oxo-5-[3-oxo-3-(4-trifluoromethyl-phenyl)-propenyl]-cyclopentyl}-heptanoic acid | 4-(trifluoromethyl)phenyl |
| 19 | trans-7-{2-[3-(4-Heptyloxy-phenyl)-3-oxo-propenyl]-5-oxo-cyclopentyl}-heptanoic acid | 4-heptyloxyphenyl |
| 20 | trans-7-[2-(3-Benzo[1,3]dioxol-5-yl-3-oxo-propenyl)-5-oxo-cyclopentyl]-heptanoic acid | benzo[1,3]dioxol-5-yl |
| 21 | trans-7-{2-[3-(3-Methoxy-phenyl)-3-oxo-propenyl]-5-oxo-cyclopentyl}-heptanoic acid | 3-methoxyphenyl |
| 22 | trans-7-(2-{3-[2-(4-Methoxy-phenoxy)-5-nitro-phenyl]-3-oxo-propenyl}-5-oxo-cyclopentyl)heptanoic acid | 2-(4-methoxyphenoxy)-5-nitro-3-methylphenyl |

TABLE 1-continued

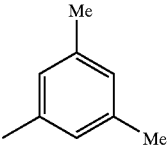

| Example Number | Name | M |
|---|---|---|
| 23 | trans-7-{2-[3-(3,5-Dimethyl-phenyl)-3-oxo-propenyl]-5-oxo-cyclopentyl}-heptanoic acid | 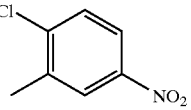 |
| 24 | trans-7-{2-[3-(2-Chloro-5-nitro-phenyl)-3-oxo-propenyl]-5-oxo-cyclopentyl}-heptanoic acid | 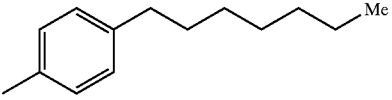 |
| 25 | trans-7-{2-[3-(4-Heptyl-phenyl)-3-oxo-propenyl]-5-oxo-cyclopentyl}-heptanoic acid | 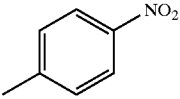 |
| 26 | trans-7-{2-[3-(4-Nitro-phenyl)-3-oxo-propenyl]-5-oxo-cyclopentyl}-heptanoic acid | 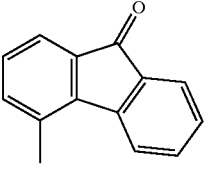 |
| 27 | trans-7-{2-Oxo-5-[3-oxo-3-(9-oxo-9H-fluoren-4-yl)-propenyl]-cyclopentyl}-heptanoic acid | 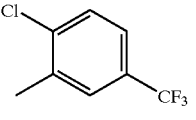 |
| 28 | trans-7-{2-[3-(2-Chloro-5-trifluoromethyl-phenyl)-3-oxo-propenyl]-5-oxo-cyclopentyl}-heptanoic acid | 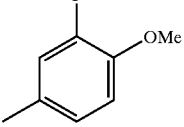 |
| 29 | trans-7-{2-[3-(3-Fluoro-4-methoxy-phenyl)-3-oxo-propenyl]-5-oxo-cyclopentyl)-heptanoic acid | 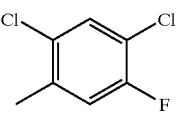 |
| 30 | trans-7-{2-[3-(2,4-Dichloro-5-fluoro-phenyl)-3-oxo-propenyl]-5-oxo-cyclopentyl}-heptanoic acid | |

TABLE 1-continued

| Example Number | Name | M |
|---|---|---|
| 31 | trans-7-{2-Oxo-5-[3-oxo-3-(4-pentyl-phenyl)-propenyl]-cyclopentyl}-heptanoic acid | 4-pentyl-phenyl |
| 32 | trans-7-{2-[3-(3,5-Dinitro-phenyl)-3-oxo-propenyl]-5-oxo-cyclopentyl}-heptanoic acid | 3,5-dinitro-phenyl |
| 33 | trans-7-{2-[3-(3,4-Difluoro-phenyl)-3-oxo-propenyl]-5-oxo-cyclopentyl}-heptanoic acid | 3,4-difluoro-phenyl |
| 34 | trans-7-[2-(3-Biphenyl-4-yl-3-oxo-propenyl)-5-oxo-cyclopentyl]-heptanoic acid | biphenyl-4-yl |
| 35 | trans-7-[2-Oxo-5-(3-oxo-3-o-tolyl-propenyl)-cyclopentyl]-heptanoic acid | o-tolyl |
| 36 | trans-7-{2-Oxo-5-[3-oxo-3-(3,4,5-trimethoxy-phenyl)-propenyl]-cyclopentyl}-heptanoic acid | 3,4,5-trimethoxy-phenyl |
| 37 | trans-7-{2-[3-(2,5-Difluoro-phenyl)-3-oxo-propenyl]-5-oxo-cyclopentyl}-heptanoic acid | 2,5-difluoro-phenyl |
| 38 | trans-7-{2-[3-(2-Chloro-4-fluoro-phenyl)-3-oxo-propenyl]-5-oxo-cyclopentyl}-heptanoic acid | 2-chloro-4-fluoro-phenyl |
| 39 | trans-7-{2-[3-(2,5-Dimethyl-phenyl)-3-oxo-propenyl]-5-oxo-cyclopentyl}-heptanoic acid | 2,5-dimethyl-phenyl |

TABLE 1-continued

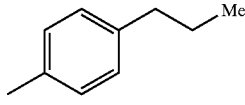

| Example Number | Name | M |
|---|---|---|
| 40 | trans-7-{2-Oxo-5-[3-oxo-3-(4-propyl-phenyl)-propenyl]-cyclopentyl}-heptanoic acid | 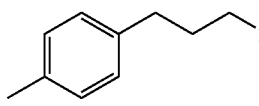 |
| 41 | trans-7-{2-[3-(4-Butyl-phenyl)-3-oxo-propenyl]-5-oxo-cyclopentyl}-heptanoic acid | 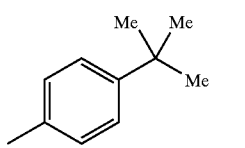 |
| 42 | trans-7-{2-[3-(4-tert-Butyl-phenyl)-3-oxo-propenyl]-5-oxo-cyclopentyl}-heptanoic acid | 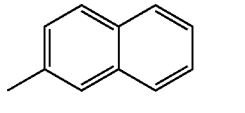 |
| 43 | trans-7-[2-(3-Naphthalen-2-yl-3-oxo-propenyl)-5-oxo-cyclopentyl]-heptanoic acid | 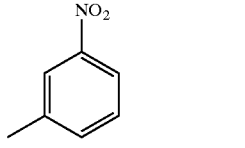 |
| 44 | trans-7-{2-[3-(3-Nitro-phenyl)-3-oxo-propenyl]-5-oxo-cyclopentyl}-heptanoic acid | 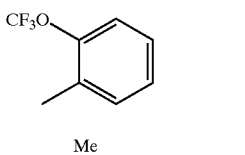 |
| 45 | trans-7-{2-Oxo-5-[3-oxo-3-(2-trifluoromethoxy-phenyl)-propenyl]-cyclopentyl}-heptanoic acid | 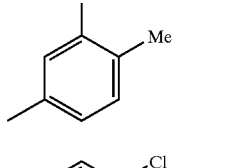 |
| 46 | trans-7-{2-[3-(3,4-Dimethyl-phenyl)-3-oxo-propenyl]-5-oxo-cyclopentyl}-heptanoic acid | 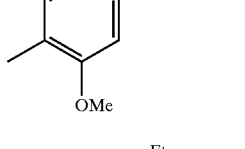 |
| 47 | trans-7-{2-[3-(4-Chloro-2-methoxy-phenyl)-3-oxo-propenyl]-5-oxo-cyclopentyl}-heptanoic acid | 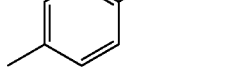 |
| 48 | trans-7-{2-[3-(4-Ethyl-phenyl)-3-oxo-propenyl]-5-oxo-cyclopentyl}-heptanoic acid | |

TABLE 1-continued

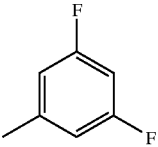

| Example Number | Name | M |
|---|---|---|
| 49 | trans-7-{2-[3-(3,5-Difluoro-phenyl)-3-oxo-propenyl]-5-oxo-cyclopentyl}-heptanoic acid | 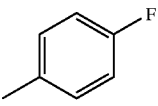 |
| 50 | trans-7-{2-[3-(4-Fluoro-phenyl)-3-oxo-propenyl]-5-oxo-cyclopentyl}-heptanoic acid | 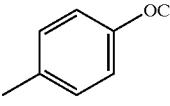 |
| 51 | trans-7-{2-Oxo-5-[3-oxo-3-(4-trifluoromethoxy-phenyl)-propenyl]-cyclopentyl}-heptanoic acid | 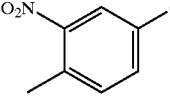 |
| 52 | trans-7-{2-[3-(2-Nitro-4-trifluoromethyl-phenyl)-3-oxo-propenyl]-5-oxo-cyclopentyl}-heptanoic acid | 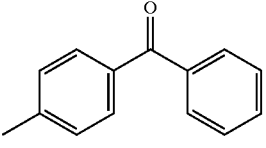 |
| 53 | trans-7-{2-[3-(4-Benzoyl-phenyl)-3-oxo-propenyl]-5-oxo-cyclopentyl}-heptanoic acid | 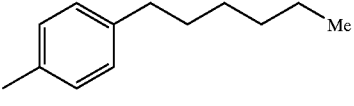 |
| 54 | trans-7-{2-[3-(4-Hexyl-phenyl)-3-oxo-propenyl]-5-oxo-cyclopentyl}-heptanoic acid | 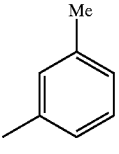 |
| 55 | trans-7-[2-Oxo-5-(3-oxo-3-m-tolyl-propenyl)-cyclopentyl]-heptanoic acid | 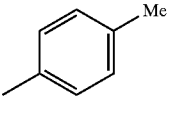 |
| 56 | trans-7-[2-Oxo-5-(3-oxo-3-p-tolyl-propenyl)-cyclopentyl]-heptanoic acid | 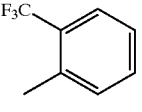 |
| 57 | trans-7-{2-Oxo-5-[3-oxo-3-(2-trifluoromethyl-phenyl)-propenyl]-cyclopentyl}-heptanoic acid | |

TABLE 1-continued

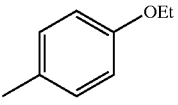

| Example Number | Name | M |
|---|---|---|
| 58 | trans-7-{2-[3-(4-Ethoxy-phenyl)-3-oxo-propenyl]-5-oxo-cyclopentyl}-heptanoic acid | 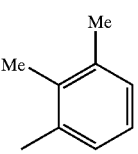 |
| 59 | trans-7-{2-[3-(2,3-Dimethyl-phenyl)-3-oxo-propenyl]-5-oxo-cyclopentyl}-heptanoic acid | 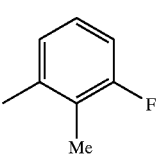 |
| 60 | trans-7-{2-[3-(3-Fluoro-2-methyl-phenyl)-3-oxo-propenyl]-5-oxo-cyclopentyl}-heptanoic acid | 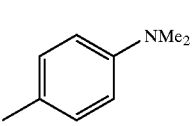 |
| 61 | trans-7-{2-[3-(4-Dimethylamino-phenyl)-3-oxo-propenyl]-5-oxo-cyclopentyl}-heptanoic acid | 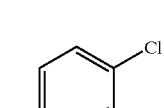 |
| 62 | trans-7-{2-[3-(4-Chloro-phenyl)-3-oxo-propenyl]-5-oxo-cyclopentyl}-heptanoic acid | 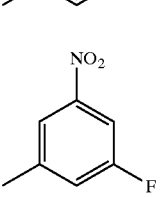 |
| 63 | trans-7-{2-[3-(3-Fluoro-5-nitro-phenyl)-3-oxo-propenyl]-5-oxo-cyclopentyl}-heptanoic acid | 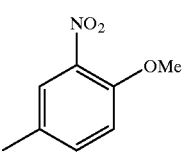 |
| 64 | trans-7-{2-[3-(4-Methoxy-3-nitro-phenyl)-3-oxo-propenyl]-5-oxo-cyclopentyl}-heptanoic acid | 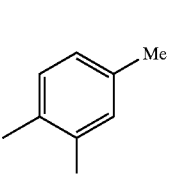 |
| 65 | trans-7-{2-[3-(2,4-Dimethyl-phenyl)-3-oxo-propenyl]-5-oxo-cyclopentyl}-heptanoic acid | |

EXAMPLE 66

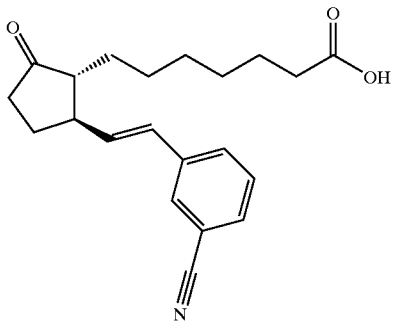

trans-7-{2-[2-(3-Cyano-phenyl)-vinyl]-5-oxo-cyclopentyl}-heptanoic acid

Wang resin bound trans-7-[2-oxo-5-(2-tributylstannanyl-vinyl)-cyclopentyl]-heptanoic acid (the compound of Preparation 1, Step F, 70 mg, 0.05 mmol, 1 eq), tris(dibenzylideneacetone)dipalladium(0) (18.2 mg, 0.02 mmol, 0.4 eq), diisopylethylamine (12.8 mg, 0.099 mmol, 2 eq), potassium carbonate (10 mg) and 3-bromo-benzonitrile (36.2 mg, 0.199 mmol, 4 eq) were placed in a well of a deep-well plate, and tetrahydrofuran was added until resin was just wet. The slurry was shaken at room temperature overnight. The resin was filtered and washed with N,N-dimethylformamide and methanol. It was repeatedly swollen with dichloromethane and shrunk with methanol. The resin was finally washed with diethyl ether to remove methanol. Cleavage of the product with trifluoroacetic acid as described in Step B of Example 3 with 90% trifluoroacetic acid in water gave the title compound of Example 66.

Examples 67–155, set forth in Table 2, were prepared using the appropriate starting materials in a manner analogous to procedures set forth in Example 66. Examples 67–155 have the following backbone structure:

TABLE 2

| Example Number | Name | M |
|---|---|---|
| 67 | trans-7-[2-(2-Benzo[1,3]dioxol-5-yl-vinyl)-5-oxo-cyclopentyl]-heptanoic acid | |
| 68 | trans-7-{2-[2-(3,4-Difluoro-phenyl)-vinyl]-5-oxo-cyclopentyl}-heptanoic acid | |
| 69 | trans-7-{2-[2-(3-Chloro-phenyl)-vinyl]-5-oxo-cyclopentyl}-heptanoic acid | |
| 70 | trans-7-(2-Oxo-5-styryl-cyclopentyl)-heptanoic acid | |
| 71 | trans-7-{2-[2-(4-Formyl-phenyl)-vinyl]-5-oxo-cyclopentyl}-heptanoic acid | |

TABLE 2-continued

| Example Number | Name | M |
|---|---|---|
| 72 | trans-5-{2-[2-(6-Carboxy-hexyl)-3-oxo-cyclopentyl]-vinyl}-2-hydroxy-benzoic acid | 5-methyl-2-hydroxy-benzoic acid substituent |
| 73 | trans-7-{2-[2-(2-Methyl-4-nitro-phenyl)-vinyl]-5-oxo-cyclopentyl}-heptanoic acid | 2-methyl-4-nitro-phenyl |
| 74 | trans-7-{2-[2-(4-Hydroxymethanesulfonyl-phenyl)-vinyl]-5-oxo-cyclopentyl}-heptanoic acid | 4-(hydroxymethanesulfonyl)-phenyl |
| 75 | trans-7-{2-[2-(2-Fluoro-phenyl)-vinyl]-5-oxo-cyclopentyl}-heptanoic acid | 2-fluoro-phenyl |
| 76 | trans-7-{2-[2-(3,5-Dimethyl-phenyl)-vinyl]-5-oxo-cyclopentyl}-heptanoic acid | 3,5-dimethyl-phenyl |
| 77 | trans-7-{2-[2-(2-Fluoro-6-trifluoromethyl-phenyl)-vinyl]-5-oxo-cyclopentyl}-heptanoic acid | 2-fluoro-6-trifluoromethyl-phenyl |
| 78 | trans-7-{2-[2-(1H-Indol-5-yl)-vinyl]-5-oxo-cyclopentyl}-heptanoic acid | 1H-indol-5-yl |

TABLE 2-continued

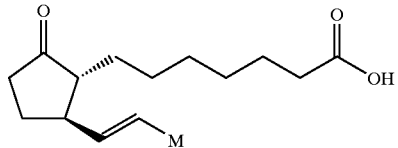

| Example Number | Name | M |
|---|---|---|
| 79 | trans-7-{2-[2-(3-Formyl-phenyl)-vinyl]-5-oxo-cyclopentyl}-heptanoic acid | 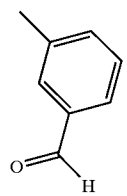 |
| 80 | trans-7-{2-[2-(2,3-Dichloro-phenyl)-vinyl]-5-oxo-cyclopentyl}-heptanoic acid | 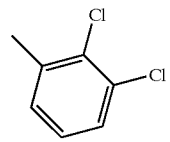 |
| 81 | trans-7-{2-[2-(3,5-Difluoro-phenyl)-vinyl]-5-oxo-cyclopentyl}-heptanoic acid |  |
| 82 | trans-7-{2-[2-(4-Acetyl-phenyl)-vinyl]-5-oxo-cyclopentyl}-heptanoic acid | 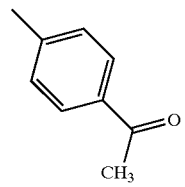 |
| 83 | trans-7-{2-[2-(4-Hydroxymethyl-phenyl)-vinyl]-5-oxo-cyclopentyl}-heptanoic acid | 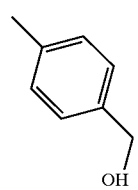 |
| 84 | trans-7-{2-[2-(3-Chloro-4-cyano-phenyl)-vinyl]-5-oxo-cyclopentyl}-heptanoic acid | 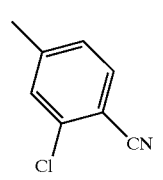 |
| 85 | trans-7-{2-[2-(4-Acetylamino-phenyl)-vinyl]-5-oxo-cyclopentyl}-heptanoic acid | 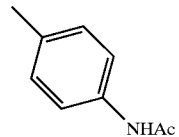 |

TABLE 2-continued

| Example Number | Name | M |
|---|---|---|
| 86 | trans-4-{2-[2-(6-Carboxy-hexyl)-3-oxo-cyclopentyl]-vinyl}-benzoic acid | |
| 87 | trans-7-{2-[2-(4-Chloro-2-methyl-phenyl)-vinyl]-5-oxo-cyclopentyl}-heptanoic acid | |
| 88 | trans-7-{2-[2-(4-Ethyl-phenyl)-vinyl]-5-oxo-cyclopentyl}-heptanoic acid | |
| 89 | trans-7-{2-[2-(3,5-Bis-trifluoromethyl-phenyl)-vinyl]-5-oxo-cyclopentyl}-heptanoic acid | |
| 90 | trans-7-[2-Oxo-5-(2-thiazol-2-yl-vinyl)-cyclopentyl]-heptanoic acid | |
| 91 | trans-7-{2-[2-(4-Carbamoyl-phenyl)-vinyl]-5-oxo-cyclopentyl}-heptanoic acid | |
| 92 | trans-7-[2-(2-Acenaphthen-5-yl-vinyl)-5-oxo-cyclopentyl]-heptanoic acid | |
| 93 | trans-7-{2-[2-(2,6-Dichloro-phenyl)-vinyl]-5-oxo-cyclopentyl}-heptanoic aicd | |

TABLE 2-continued

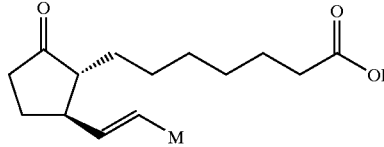

| Example Number | Name | M |
|---|---|---|
| 94 | trans-7-[2-Oxo-5-(2-p-tolyl-vinyl)-cyclopentyl]-heptanoic acid | 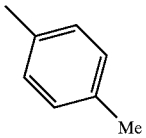 |
| 95 | trans-7-{2-[2-(3,4-Dimethyl-phenyl)-vinyl]-5-oxo-cyclopentyl}-heptanoic acid | 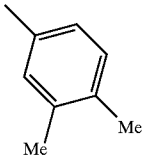 |
| 96 | trans-4-{2-[2-(6-Carboxy-hexyl)-3-oxo-cyclopentyl]-vinyl}-benzoic acid methyl ester | 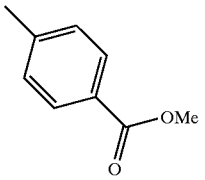 |
| 97 | trans-7-{2-[2-(3-Fluoro-biphenyl-4-yl)-vinyl]-5-oxo-cyclopentyl}-heptanoic acid | 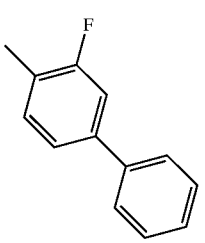 |
| 98 | trans-7-{2-[2-(4-Fluoro-2-methyl-phenyl)-vinyl]-5-oxo-cyclopentyl}-heptanoic acid | 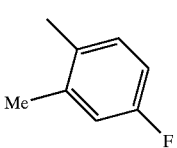 |
| 99 | trans-7-{2-Oxo-5-[2-(3-vinyl-phenyl)-vinyl]-cyclopentyl}-heptanoic acid | 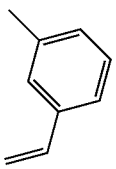 |
| 100 | trans-7-{2-[2-(4-Fluoro-2-trifluoromethyl-phenyl)-vinyl]-5-oxo-cyclopentyl}-heptanoic acid | 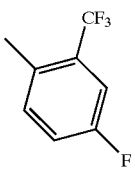 |
| 101 | trans-7-{2-[2-(2-Fluoro-5-trifluoromethyl-phenyl)-vinyl]-5-oxo-cyclopentyl}-heptanoic acid | 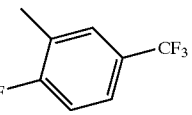 |

TABLE 2-continued

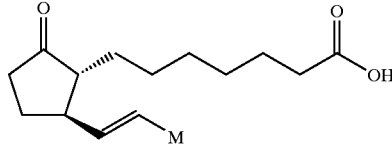

| Example Number | Name | M |
|---|---|---|
| 102 | trans-7-{2-[2-(2-Cyano-phenyl)-vinyl]-5-oxo-cyclopentyl}-heptanoic acid | 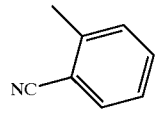 |
| 103 | trans-7-{2-Oxo-5-[2-(4-pentyl-phenyl)-vinyl]-cyclopentyl}-heptanoic acid | 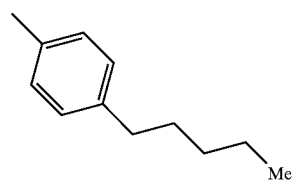 |
| 104 | trans-7-{2-[2-(6-Hydroxy-naphthalen-2-yl)-vinyl]-5-oxo-cyclopentyl}-heptanoic acid | 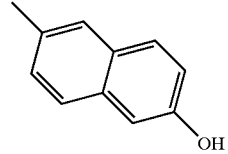 |
| 105 | trans-7-{2-Oxo-5-[2-(4-propyl-phenyl)-vinyl]-cyclopentyl}-heptanoic acid | 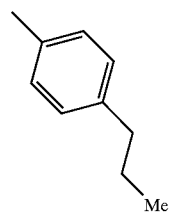 |
| 106 | trans-7-{2-[2-(4-Chloro-2,3,5,6-tetrafluoro-phenyl)-vinyl]-5-oxo-cyclopentyl}-heptanoic acid | 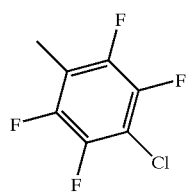 |
| 107 | trans-7-{2-Oxo-5-[2-(2-trifluoromethyl-phenyl)-vinyl]-cyclopentyl}-heptanoic acid | 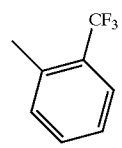 |
| 108 | trans-7-{2-[2-(2-Methoxy-phenyl)-vinyl]-5-oxo-cyclopentyl}-heptanoic acid | 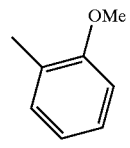 |
| 109 | trans-7-{2-[2-(4-Chloro-phenyl)-vinyl]-5-oxo-cyclopentyl}-heptanoic acid | 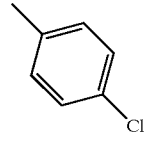 |

TABLE 2-continued

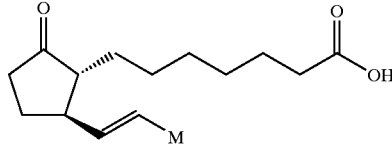

| Example Number | Name | M |
|---|---|---|
| 110 | trans-7-{2-[2-(3-Fluoro-phenyl)-vinyl]-5-oxo-cyclopentyl}-heptanoic acid | 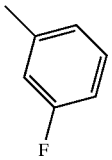 |
| 111 | trans-7-{2-[2-(3,5-Bis-trifluoromethyl-phenyl)-vinyl]-5-oxo-cyclopentyl}-heptanoic acid | 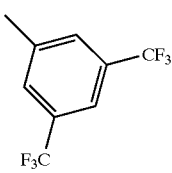 |
| 112 | trans-7-{2-[2-(4-Methanesulfonyl-phenyl)-vinyl]-5-oxo-cyclopentyl}-heptanoic acid | 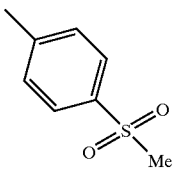 |
| 113 | trans-7-{2-[2-(4-Hydroxy-2,6-dimethyl-phenyl)-vinyl]-5-oxo-cyclopentyl}-heptanoic acid | 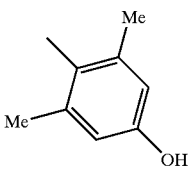 |
| 114 | trans-7-{2-[2-(4-Acetylamino-2-chloro-phenyl)-vinyl]-5-oxo-cyclopentyl}-heptanoic acid | 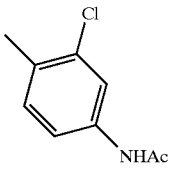 |
| 115 | trans-7-{2-[2-(2,3-Difluoro-phenyl)-vinyl]-5-oxo-cyclopentyl}-heptanoic acid |  |
| 116 | trans-7-{2-[2-(2,6-Difluoro-phenyl)-vinyl]-5-oxo-cyclopentyl}-heptanoic acid | 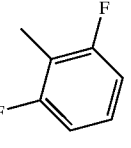 |
| 117 | trans-7-{2-[2-(2,4-Dimethyl-phenyl)-vinyl]-5-oxo-cyclopentyl}-heptanoic acid | 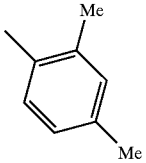 |

TABLE 2-continued

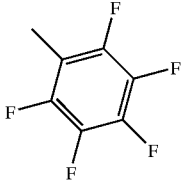

| Example Number | Name | M |
|---|---|---|
| 118 | trans-7-{2-Oxo-5-[2-(2,3,4,5,6-pentafluoro-phenyl)-vinyl]-cyclopentyl}-heptanoic acid | 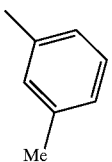 |
| 119 | trans-7-[2-Oxo-5-(2-m-tolyl-vinyl)-cyclopentyl]-heptanoic acid | 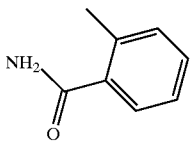 |
| 120 | trans-7-{2-[2-(2-Carbamoyl-phenyl)-vinyl]-5-oxo-cyclopentyl}-heptanoic acid | 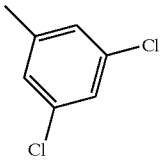 |
| 121 | trans-7-{2-[2-(3,5-Dichloro-phenyl)-vinyl]-5-oxo-cyclopentyl}-heptanoic acid | 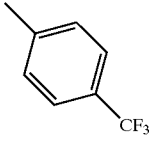 |
| 122 | trans-7-{2-Oxo-5-[2-(4-trifluoromethyl-phenyl)-vinyl]-cyclopentyl}-heptanoic acid |  |
| 123 | trans-7-{2-Oxo-5-[2-(3,4,5-trifluoro-phenyl)-vinyl]-cyclopentyl}-heptanoic acid | 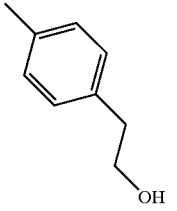 |
| 124 | trans-7-(2-{2-[4-(2-Hydroxy-ethyl)-phenyl]-vinyl}-5-oxo-cyclopentyl)-heptanoic acid | 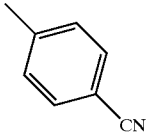 |
| 125 | trans-7-{2-[2-(4-Cyano-phenyl)-vinyl]-5-oxo-cyclopentyl}-heptanoic acid |  |

TABLE 2-continued

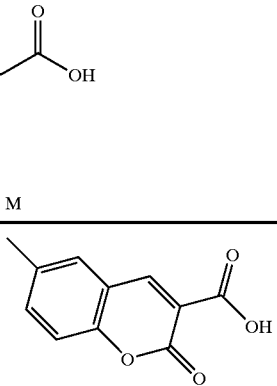

| Example Number | Name | M |
|---|---|---|
| 126 | trans-6-{2-[2-(6-Carboxy-hexyl)-3-oxo-cyclopentyl]-vinyl}-2-oxo-2H-chromene-3-carboxylic acid | 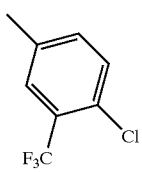 |
| 127 | trans-7-{2-[2-(4-Chloro-3-trifluoromethyl-phenyl)-vinyl]-5-oxo-cyclopentyl}-heptanoic acid | 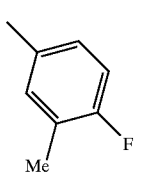 |
| 128 | trans-7-{2-[2-(4-Fluoro-3-methyl-phenyl)-vinyl]-5-oxo-cyclopentyl}-heptanoic acid | 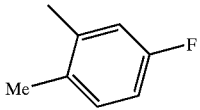 |
| 129 | trans-7-{2-[2-(5-Fluoro-2-methyl-phenyl)-vinyl]-5-oxo-cyclopentyl}-heptanoic acid | 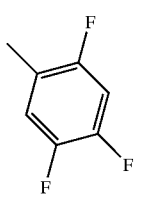 |
| 130 | trans-7-{2-Oxo-5-[2-(2,4,5-trifluoro-phenyl)-vinyl]-cyclopentyl}-heptanoic acid | 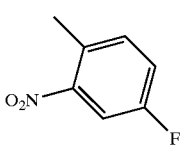 |
| 131 | trans-7-{2-[2-(4-Fluoro-2-nitro-phenyl)-vinyl]-5-oxo-cyclopentyl}-heptanoic acid | 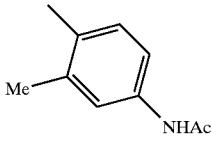 |
| 132 | trans-7-{2-[2-(4-Acetylamnio-2-methyl-phenyl)-vinyl]-5-oxo-cyclopentyl}-heptanoic acid | 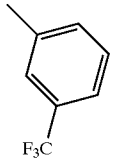 |
| 133 | trans-7-{2-Oxo-5-[2-(3-trifluoromethyl-phenyl)-vinyl]-cyclopentyl}-heptanoic acid |  |

TABLE 2-continued

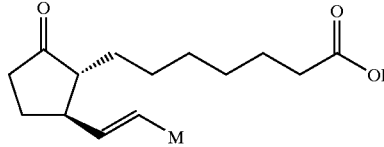

| Example Number | Name | M |
|---|---|---|
| 134 | trans-7-{2-[2-(4-Fluoro-phenyl)-vinyl]-5-oxo-cyclopentyl}-heptanoic acid | 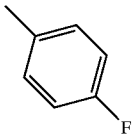 |
| 135 | trans-7-{2-[2-(4-tert-Butyl-phenyl)-vinyl]-5-oxo-cyclopentyl}-heptanoic acid | 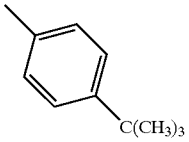 |
| 136 | trans-7-{2-[2-(3,4-Dichloro-phenyl)-vinyl]-5-oxo-cyclopentyl}-heptanoic acid | 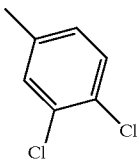 |
| 137 | trans-7-{2-[2-(4-Benzoyl-phenyl)-vinyl]-5-oxo-cyclopentyl}-heptanoic acid | 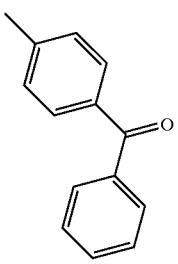 |
| 138 | trans-7-{2-[2-(4-Nitro-phenyl)-vinyl]-5-oxo-cyclopentyl}-heptanoic acid | 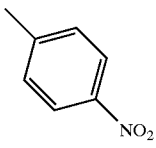 |
| 139 | trans-7-{2-[2-(2,4-Difluoro-phenyl)-vinyl]-5-oxo-cyclopentyl}-heptanoic acid | 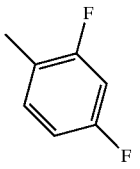 |
| 140 | trans-7-{2-[2-(2-Ethyl-phenyl)-vinyl]-5-oxo-cyclopentyl}-heptanoic acid | 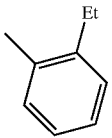 |
| 141 | trans-7-{2-[2-(2,3-Dimethyl-phenyl)-vinyl]-5-oxo-cyclopentyl}-heptanoic acid | 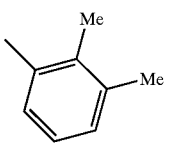 |

TABLE 2-continued

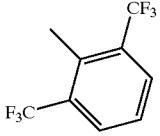

| Example Number | Name | M |
|---|---|---|
| 142 | trans-7-{2-[2-(2,6-Bis-trifluoromethyl-phenyl)-vinyl]-5-oxo-cyclopentyl}-heptanoic acid | 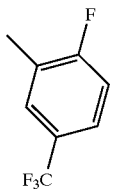 |
| 143 | trans-7-{2-[2-(2-Fluoro-5-trifluoromethyl-phenyl)-vinyl]-5-oxo-cyclopentyl}-heptanoic acid | 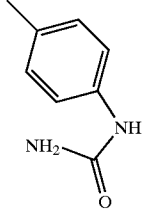 |
| 144 | trans-7-{2-Oxo-5-[2-(4-ureido-phenyl)-vinyl]-cyclopentyl}-heptanoic acid | 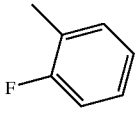 |
| 145 | trans-7-{2-[2-(2-Fluoro-phenyl)-vinyl]-5-oxo-cyclopentyl}-heptanoic acid | 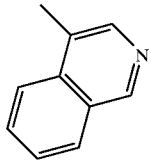 |
| 146 | trans-7-[2-(2-Isoquinolin-4-yl-vinyl)-5-oxo-cyclopentyl}-heptanoic acid | 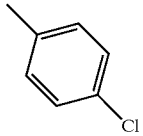 |
| 147 | trans-7-{2-[2-(4-Chloro-phenyl)-vinyl]-5-oxo-cyclopentyl}-heptanoic acid | 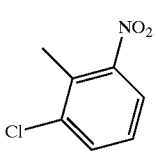 |
| 148 | trans-7-{2-[2-(2-Chloro-6-nitro-phenyl)-vinyl]-5-oxo-cyclopentyl}-heptanoic acid |  |

TABLE 2-continued

| Example Number | Name | M |
|---|---|---|
| 149 | trans-7-[2-(2-Biphenyl-4-yl-vinyl)-5-oxo-cyclopentyl]-heptanoic acid | biphenyl-4-yl |
| 150 | trans-7-{2-[2-(2,4-Dicloro-thiophen-3-yl)-vinyl]-5-oxo-cyclopentyl}-heptanoic acid | 2,4-dichloro-thiophen-3-yl |
| 151 | trans-7-{2-[2-(2,5-Dimethyl-phenyl)-vinyl]-5-oxo-cyclopentyl}-heptanoic acid | 2,5-dimethyl-phenyl |
| 152 | trans-7-[2-Oxo-5-(2-o-tolyl-vinyl)-cyclopentyl]-heptanoic acid | o-tolyl |
| 153 | trans-7-{2-[2-(2-Fluoro-3-trifluoromethyl-phenyl)-vinyl]-5-oxo-cyclopentyl}-heptanoic acid | 2-fluoro-3-trifluoromethyl-phenyl |
| 154 | trans-7-{2-Oxo-5-[2-(2,3,5-trifluoro-phenyl)-vinyl]-cyclopentyl}-heptanoic acid | 2,3,5-trifluoro-phenyl |
| 155 | trans-7-{2-[2-(4-Fluoro-3-trifluoromethyl-phenyl)-vinyl]-5-oxo-cyclopentyl}-heptanoic acid | 4-fluoro-3-trifluoromethyl-phenyl |

Examples 156–209, set forth in Table 3, are prepared from the appropriate starting materials in a manner analogous to procedures set forth in Example 66. Examples 156–209 have the following backbone structure:

TABLE 3

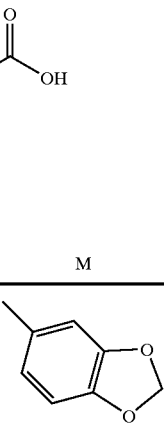

| Example Number | Name | M |
|---|---|---|
| 156 | trans-trans-7-[2-(2-Benzo[1,3]dioxol-5-yl-vinyl)-3-hydroxy-5-oxo-cyclopentyl]-heptanoic acid | 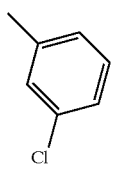 |
| 157 | trans-trans-7-{2[2-(3-Chloro-phenyl)-vinyl]-3-hydroxy-5-oxo-cyclopentyl}-heptanoic acid. | 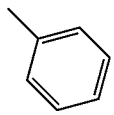 |
| 158 | trans-trans-7-(3-Hydroxy-2-oxo-5-styryl-cyclopentyl)-heptanoic acid. | 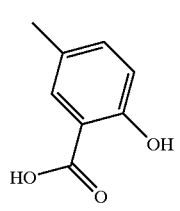 |
| 159 | trans-trans-5-{2-[2-(6-Carboxy-hexyl)-5-hydroxy-3-oxo-cyclopentyl]-vinyl}-2-hydroxy-benzoic acid. | 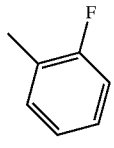 |
| 160 | trans-trans-7-{2-[2-(2-Fluoro-phenyl)-vinyl]-3-hydroxy-3-hydroxy-5-oxo-cyclopentyl}-heptanoic acid | 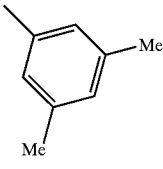 |
| 161 | trans-trans-7-{2-[2-(3,5-Dimethyl-phenyl)-vinyl]-3-hydroxy-5-oxo-cyclopenlyl}-heptanoic acid |  |
| 162 | trans-trans-7-{2-[2-(2-Fluoro-6-trifluoromethyl-phenyl)-vinyl]-3-hydroxy-5-oxo-cyclopentyl}-heptanoic acid. | 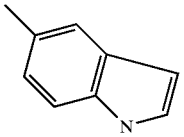 |
| 163 | trans-trans-7-{2-[2-(1H-indol-5-yl)-vinyl]-3-hydroxy-5-oxo-cyclopentyl}-heptanoic acid. | |

TABLE 3-continued

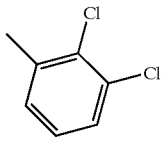

| Example Number | Name | M |
|---|---|---|
| 164 | trans-trans-7-{2-[2-(2,3-Dichloro-penyl)-vinyl]-3-hydroxy-5-oxo-cyclopentyl}-heptanoic acid | 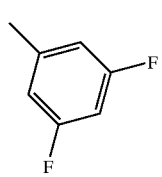 |
| 165 | trans-trans-7-{2-[2-(3,5-Difluoro-phenyl)-vinyl]-3-hydroxy-5-oxo-cyclopentyl}heptanoic acid. | 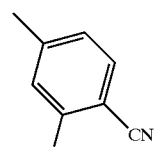 |
| 166 | trans-trans-7-{2-[2-(3-Chloro-4-cyano-phenyl)-vinyl{-3-hydroxy-5-oxo-cyclopentyl}-heptanoic acid. | 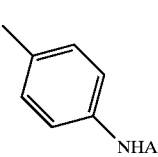 |
| 167 | trans-trans-7-{2-[2-(4-Acetylamino-phenyl)-vinyl}-3-hydroxy-5-oxo-cyclopenlyl}-heptanoic acid. | 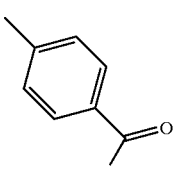 |
| 168 | trans-trans-4-{2-[2-(6-Carboxy-hexyl)-5-hydroxy-3-oxo-cyclopentyl}-vinyl}-benzoic acid. | 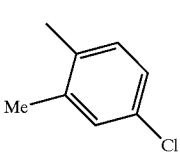 |
| 169 | trans-trans-7-{2-[2-(4-Chloro-2-methyl-phenyl)-vinyl]-3-hydroxy-5-oxo-cyclopentyl)-heptanoic acid. |  |
| 170 | trans-trans-7-{2-[2-(4-Ethyl-phenyl)-vinyl]-3-hydroxy-5-oxo-cyclopentyl}-heptanoic acid. | 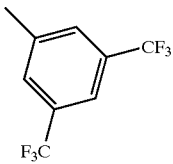 |
| 171 | trans-trans-7-{2-[2-(3,5-Bis-trifluoromethyl-phenyl)-vinyl}-3-hydroxy-5-oxo-cyclopentyl)-heptanoic acid |  |

TABLE 3-continued

| Example Number | Name | M |
|---|---|---|
| 172 | trans-trans-7-[3-Hydroxy-2-oxo-5-(2-thiazol-2-yl-vinyl)-cyclopentyl]-heptanoic acid. | 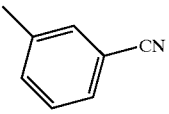 |
| 173 | trans-trans-7-{2-[2-(3-Cyano-phenyl)-vinyl]-3-hydroxy-5-oxo-cyclopentyl]-heptanoic acid. | 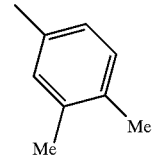 |
| 174 | trans-trans-7-{2-[2-(3,4-Dimethyl-phenyl)-vinyl}-3-hydroxy-5-oxo-cyclopentyl}-heptanoic acid. | 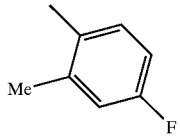 |
| 175 | trans-trans-7-{2-[2-(4-Fluoro-2-methyl-phenyl)-vinyl}-3-hydroxy-5-oxo-cyclopentyl}-heptanoic acid. | 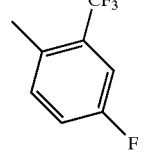 |
| 176 | trans-trans-7-{2-[2-(4-Fluoro-2-trifluoromethyl-phenyl)-vinyl}-3-hydroxy-5-oxo-cyclopentyl}-heptanoic acid. | 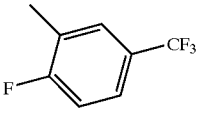 |
| 177 | trans-trans-7-{2-[2-(2-Fluoro-5-triflurormethyl-phenyl)-vinyl]-3-hydroxy-5-oxo-cyclopentyl}-heptanoic acid | 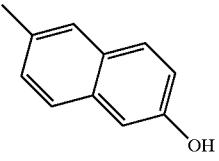 |
| 178 | trans-trans-7-{2-[2-(6-Hydroxy-naphthalen-2-yl)-vinyl]-3-hydroxy-5-oxo-cyclopentyl}-heptanoic acid | 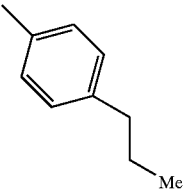 |
| 179 | trans-trans-7-{3-Hydroxy-2-oxo-5-[2-(4-propyl-phenyl)-vinyl]-cyclopentyl}-heptanoic acid. |  |

TABLE 3-continued

| Example Number | Name | M |
|---|---|---|
| 180 | trans-trans-7-{3-Hydroxy-2-oxo-5-[2-(2-trifluoromethyl-phenyl)-vinyl]-cyclopentyl}-heptanoic acid | 2-(trifluoromethyl)phenyl |
| 181 | trans-trans-7-{2-[2-(4-Chloro-phenyl)-vinyl]-3-hydroxy-5-oxo-cyclopentyl}-heptanoic acid. | 4-chlorophenyl |
| 182 | trans-trans-7-{2-[2-(4-Hydroxy-2,6-dimethyl-phenyl)-vinyl}-3-hydroxy-5-oxo-cyclopentyl}-heptanoic acid. | 4-hydroxy-2,6-dimethylphenyl |
| 183 | trans-trans-7-{2-[2-(2,3-Difluoro-phenyl)-vinyl}-3-hydroxy-5-oxo-cyclopentyl}-heptanoic acid. | 2,3-difluorophenyl |
| 184 | trans-trans-7-{2-[2-(2,6-Difluoro-phenyl)-vinyl]-3-hydroxy-5-oxo-cyclopentyl}-heptanoic acid | 2,6-difluorophenyl |
| 185 | trans-trans-7-{3-Hydroxy-2-oxo-5-[2-(2,3,4,5,6-pentafluoro-phenyl)-vinyl]-cyclopentyl}-heptanoic acid | pentafluorophenyl |
| 186 | trans-trans-7-[3-Hydroxy-2-oxo-5-(2-m-tolyl-vinyl)-cyclopentyl]-heptanoic acid | 3-methylphenyl |
| 187 | trans-trans-7-{2-[2-(2-Carbamoyl-phenyl)-vinyl]-3-hydroxy-5-oxo-cyclopentyl}-heptanoic acid. | 2-carbamoylphenyl |

TABLE 3-continued

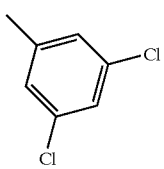

| Example Number | Name | M |
|---|---|---|
| 188 | trans-trans-7-{2-[2-(3,5-Dichloro-phenyl)-vinyl]-3-hydroxy-5-oxo-cyclopentyl}-heptanoic acid. | 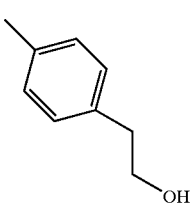 |
| 189 | trans-trans-7-(2-{2-[4-(2-Hydroxy-ethyl)-phenyl]-vinyl}-3-hydroxy-5-oxo-cyclopentyl)-heptanoic acid | 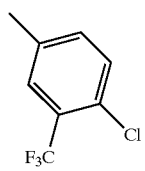 |
| 190 | trans-trans-7-{2-[2-(4-Chloro-3-trifluoromethyl-phenyl)-vinyl]-3-hydroxy-5-oxo-cyclopentyl}-heptanoic acid. | 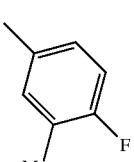 |
| 191 | trans-trans-7-{2-[2-(4-Fluoro-3-methyl-phenyl)-vinyl]-3-hydroxy-5-oxo-cyclopentyl}-heptanoic acid. | 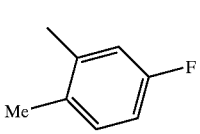 |
| 192 | trans-trans-7-{2-[2-(5-Fluoro-2-methyl-phenyl)-vinyl]-3-hydroxy-5-oxo-cyclopentyl}-heptanoic acid | |
| 193 | trans-trans-7-{3-Hydroxy-2-oxo-5-[2-(2,4,5-trifluoro-phenyl)-vinyl] cyclopentyl}-heptanoic acid. | 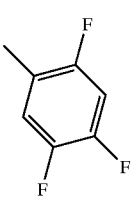 |
| 194 | trans-trans-7-{2-[2-(4-Fluoro-2-nitro-phenyl)-vinyl]-3-hydroxy-5-oxo-cyclopentyl}-heptanoic acid | 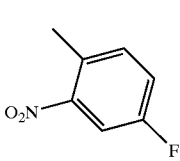 |

TABLE 3-continued

| Example Number | Name | M |
|---|---|---|
| 195 | trans-trans-7-{3-Hydroxy-2-oxo-5-[2-(3-trifluoromethyl-phenyl)-vinyl]-cyclopentyl}-heptanoic acid | 3-(F₃C)-C₆H₄– |
| 196 | trans-trans-7-{2-[2-(4-Fluoro-phenyl)-vinyl]-3-hydroxy-5-oxo-cyclopentyl}-heptanoic acid. | 4-F-C₆H₄– |
| 197 | trans-trans-7-{2-[2-(3,4-Dichloro-phenyl)-vinyl]-3-hydroxy-5-oxo-cyclopentyl}-heptancic acid. | 3,4-Cl₂-C₆H₃– |
| 198 | trans-trans-7-{2-[2-(4-nitro-phenyl)-vinyl]-3-hydroxy-5-oxo-cyclopentyl}-heptanoic acid | 4-O₂N-C₆H₄– |
| 199 | trans-trans-7-{2-[(2-(2,4-Difluoro-phenyl)-vinyl]-3-hydroxy-5-oxo-cyclopentyl}-heptanoic acid. | 2,4-F₂-C₆H₃– |
| 200 | trans-trans-7-{2-[2-(2-Ethyl-phenyl)-vinyl]-3-hydroxy-5-oxo-cyclopentyl}-heptanoic acid. | 2-Et-C₆H₄– |
| 201 | trans-trans-7-{2-[2-(2,3-Dimethyl-phenyl)-vinyl]-3-hydroxy-5-oxo-cyclopentyl}-heptanoic acid | 2,3-Me₂-C₆H₃– |
| 202 | trans-trans-7-{2-[2-(2,6-Bis-trifluoromethyl-phenyl)-vinyl]-3-hydroxy-5-oxo-cyclopentyl}-heptanoic acid | 2,6-(F₃C)₂-C₆H₃– |

TABLE 3-continued

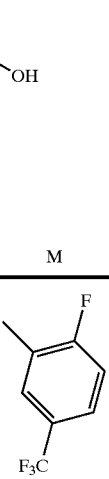

| Example Number | Name | M |
|---|---|---|
| 203 | trans-trans-7-{2-[2-(2-Fluoro-5-trifluoromethyl-phenyl)-vinyl]-3-hydroxy-5-oxo-cyclopentyl}-heptanoic acid | 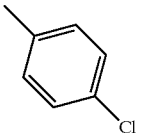 |
| 204 | trans-trans-7-{2-[2-(4-Chloro-pheynl)-vinyl]-3-hydroxy-5-oxo-cyclopentyl}-heptanoic acid. | 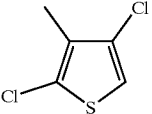 |
| 205 | trans-trans-7-{2-[2-(2,4-Dichloro-thiophen-3-yl)-vinyl]-3-hydroxy-5-oxo-cyclopentyl}-heptanoic acid. | 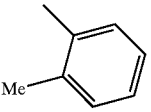 |
| 206 | trans-trans-7-{3-Hydroxy-2-oxo-5-(2-o-tolyl-vinyl)-cyclopentyl}-heptanoic acid. |  |
| 207 | trans-trans-7-{2-[2-(2-Fluoro-3-trifluoromethyl-phenyl)-vinyl]-3-hydroxy-5-oxo-cyclopentyl}-heptanoic acid | 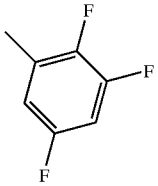 |
| 208 | trans-trans-7-(3-Hydroxy-2-oxo-5-[2-(2,3,5-trifluoro-phenyl)-vinyl]-cyclopentyl}-heptanoic acid | 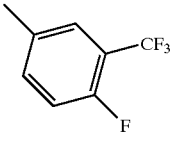 |
| 209 | trans-trans-7-{2-[2-(4-Fluoro-3-trifluoromethyl-phenyl)-vinyl]-3-hydroxy-5-oxo-cyclopentyl}-heptanoic acid. | |

Examples 210–214, set forth in Table 4, were prepared using the appropriate starting materials in a manner analogous to procedures set forth in Example 3. Examples 210–214 have the following backbone structure:

TABLE 4

| Example Number | Name | M |
|---|---|---|
| 210 | trans-trans-7-{2-[3-(3,5-Dichloro-phenyl)-3-oxo-propenyl]-3-hydroxy-5-oxo-cyclopentyl}-heptanoic acid | 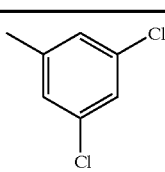 |
| 211 | trans-trans-7-{2-[3-(3-Chloro-phenyl)-3-oxo-propenyl]-3-hydroxy-5-oxo-cyclopentyl}-heptanoic acid | 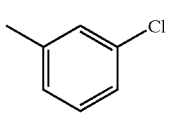 |
| 212 | trans-trans-7-{2-[3-(3,5-Difluoro-phenyl)-3-oxo-propenyl]-3-hydroxy-5-oxo-cyclopentyl}-heptanoic acid | 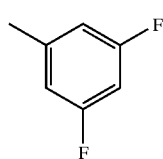 |
| 213 | trans-trans-7-(3-hydroxy-5-oxo-2-styryl-cyclopentyl)-heptanoic acid. | 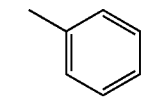 |
| 214 | trans-trans-7-{2-[3-(3-trifluoromethyl-phenyl)-3-oxo-propenyl]-3-hydroxy-5-oxo-cyclopentyl}-heptanoic acid | 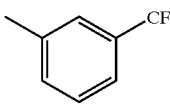 |

Preparation 1

Wang resin bound Trans-7-[2-oxo-5-(2-tributylstannanyl-vinyl)-cyclopentyl]-heptanoic acid methyl ester Step A 7-Oxo-heptanoic acid methyl ester. A solution of cycloheptene (10.0 g, 104.0 mmol) in dry dichloromethane (400 mL) and dry methanol (100 mL) containing sodium bicarbonate (4 g) was cooled to −78° C. and ozone was bubbled through. The colorless solution turned pale blue over a period of 4 h. The solution was purged with nitrogen to remove excess ozone and was diluted with benzene (100 mL) before evaporating to a volume of 150 mL behind a screen at about 20° C. Additional benzene (100 mL) was added and the volume was reduced on a rotary evaporator to about 150 mL (temperature was kept at 28° C.). The colorless solution was cooled to 0° C. and triethylamine (32 mL) and acetic anhydride (42 mL) was added in one portion with stirring. A mild exothermic reaction proceeded and the reaction was stirred for 1 h to give a dark red mixture. The mixture was washed with dilute aqueous hydrochloric acid (2M) until the organic phase became acidic, and was washed with dilute potassium hydroxide until the organic layer became basic. The solution was dried and the solvent was removed to give the title compound of Step A as a golden oil. No further purification was necessary.

Step B 7-(2-Oxo-cyclopentylidene)-heptanoic acid methyl ester. 4-Cyclopent-1-enyl-morpholine (145 g, 946 mmol) and 7-oxo-heptanoic acid methyl ester obtained from multiple runs of Step A (115 g, 727 mmol) were dissolved in dry toluene (1000 mL) and the solution was heated at reflux under Dean-Stark conditions for 18 h. The reaction was cooled to about 45° C. and a 1:1 mixture of water:hydrochloric add (175 mL) was added. The solution was stirred for 2 h. The organic phase was dried (magnesium sulfate), filtered, and concentrated to provide the title compound of Step B.

Step C 6-(5-Oxo-cyclopent-1-enyl)-heptanoic acid methyl ester. To a solution of 6-(2-oxo-cyclopentylidene)-heptanoic acid methyl ester obtained in Step B in methanol (1000 mL) was added concentrated hydrochloric acid (100 mL) and the reaction was heated at reflux for 20 h. The reaction mixture was cooled and was diluted with ethyl acetate. The organic solution was neutralized with aqueous sodium bicarbonate, dried (magnesium sulfate), filtered, and concentrated. Purification by distillation (145–155° C. at about 0.2 mmHg) provided 40 g of the title compound of Step C. $^1$H NMR (CDCl$_3$, 250 MHz) d 7.28 (m, 1H), 3.65 (s, 3H), 2.54 (t, 2H), 2.38 (m, 2H), 2.28 (t, 2H), 2.14 (m, 2H), 1.61 (m, 2H), 1.45 (m, 2H), 1.31 (m, 4H).

Step D

Preparation of trans-7-[2-oxo-5-(2-tributylstannanyl-vinyl)-cyclopentyl]-heptanoic acid methyl ester. Copper cyanide (7.5 g, 83 mmol) in tetrahydrofuran (100 mL) was treated with methyl lithium (124 mL, 1.4 M in diethyl ether, 174 mmol) at 0° C. The cooling bath was removed and (E)-1,2-bis(tributylstannyl)ethylene (50 g, 83 mmol) in tetrahydrofuran (100 mL) was added. After 1.5–2 hrs at room temperature the mixture was cooled to −78° C. and 6-(5-oxo-cyclopent-1-enyl)-heptanoic acid methyl ester of Step C (12.9 g, 57 mmol) in tetrahydrofuran (100 mL) was added rapidly via cannula. After 1.5 h, the mixture was quenched with 10% ammonium hydroxide in saturated ammonium chloride solution. The aqueous solution was extracted with ethyl acetate and the combined organic layers were washed with 10% ammonium hydroxide in saturated ammonium chloride solution. The organic solution was dried (magnesium sulfate), filtered, and concentrated. Purification by flash chromatography (hexanes to 10% ethyl acetate in hexanes) provided the desired product (8.5 g) as a clear and colorless oil. The mixture was added to a solution of potassium tert-butoxide (3.1 mL, 1M in tetrahydrofuran, 3.1 mmol) and tetrahydrofuran (200 mL) and was stirred at room temperature for 48 h. Water was added and the product was extracted into ethyl acetate. The organic solution was washed with brine, dried (magnesium sulfate), and concentrated in vacuo. Purification by flash chromatography (hexanes to 5% ethyl acetate in hexanes) provided the title compound of Step D as a clear and colorless liquid. $^1$H NMR (CDCl$_3$, 250 MHz) d 6.08–5.8 (m, 2H), 3.68 (s, 3H), 2.57–1.74 (m, 6H), 1.68–1.20 (m, 24H), 0.90 (m, 13H).

Step E

Preparation of trans-7-[2-oxo-5-(2-tributylstannanyl-vinyl)-cyclopentyl]-heptanoic acid. Potassium dihydrogen phosphate (4.6 g, 33.44 mmol) was dissolved in deionized water (0.5 L), and was brought to pH 7 using sodium hydroxide solution (2M). To this was added Candida Cycl-ridraceae (400 mg). The solution was warmed to 37–40° C., and trans-7-[2-oxo-5-(2-tributylstannanyl-vinyl)-cyclopentyl]-heptanoic acid methyl ester of Step D (3.00 g, 13.38 mmol) was added with vigorous stirring. After 4 h, concentrated hydrochloric acid was added to bring the pH to 1 and the solution was extracted with ethyl acetate. The organic phase was dried, and the solvent was removed in vacua to yield the title compound as a yellow syrup.

Step F

Wang resin bound trans-7-[2-Oxo-5-(2-tributylstannanyl-vinyl)-cyclopentyl]-heptanoic acid. A dichloromethane (5 mL) solution of trans-7-[2-oxo-5-(2-tributylstannanyl-vinyl)-cyclopentyl]-heptanoic acid of Step E (6.35 g, 12.05 mmol, 3 eq) was added to the Wang resin (5.66 g, 4.02 mmol, 1 eq) along with diisopropylethylamine (6.23 g, 48.20 mmol, 12 eq). The mixture was allowed to swell for 1 hour, and EDC (2.31 g, 12.05 mmol, 3 eq) was added followed by 4-dimethylaminopyridine (catalytic amount about 20 mg). The mixture was stirred at room temperature overnight. The resin was filtered, washed with dichloromethane (20 mL×2), repeatedly swollen with dichloromethane (20 mL) and shrunk with methanol (20 mL). The resin was washed with diethyl ether (20 mL×3) and dried on a filter funnel attached to a water aspirator for 30 minutes. Further drying under high vacuum for 5 hours provided the title compound as a free-flowing yellow resin.

What is claimed is:

1. A method for treating a mammal having a condition which presents with low bone mass comprising administering to said mammal a therapeutically effective amount of a compound of the formula I$^A$

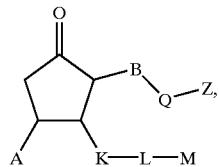

a prodrug thereof or a pharmaceutically acceptable salt of said compound or said prodrug wherein A is hydrogen or hydroxy;

B is propylene, propenylene or propynylene;

Q is propylene, —CH$_2$OCH$_2$—, thiazolyl, pyridyl, phenyl or thienyl;

Z is carboxyl, (C$_1$–C$_6$)alkoxycarbonyl, tetrazolyl, 1,2,4-oxadiazolyl or 5-oxo-1,2,4-oxadiazolyl;

K is ethylene or ethynylene;

L is a bond or —CO—;

M is —Ar, —Ar$^1$—V—Ar$^2$, —Ar$^1$—S—Ar$^2$ or —Ar$^1$—O—Ar$^2$ wherein

Ar, Ar$^1$ and Ar$^2$ are each independently a fully saturated, partially unsaturated or fully unsaturated five to eight membered ring optionally having one to four heteroatoms selected independently from oxygen, sulfur and nitrogen, or, a bicyclic ring consisting of two fused partially saturated, fully saturated or fully unsaturated five and/or six membered rings, taken independently, optionally having one to four heteroatoms selected independently from nitrogen, sulfur and oxygen, or, a tricyclic ring consisting of three fused partially saturated, fully saturated or fully unsaturated five and/or six membered rings, taken independently, optionally having one to four heteroatoms selected independently from nitrogen, sulfur and oxygen, any of said partially saturated or fully saturated rings optionally having one or more oxo groups substituted on carbon, said Ar, Ar$^1$ and Ar$^2$ moieties are each independently optionally substituted, on one ring if the moiety is monocyclic, on one or both rings if the moiety is bicyclic, or on one, two or three rings is the moiety is tricyclic, on carbon with up to three substituents independently selected from R$^1$, R$^2$ and R$^3$ wherein R$^1$, R$^2$ and R$^3$ are hydroxy, nitro, halo, (C$_1$–C$_7$)alkoxy, (C$_1$–C$_4$)alkoxy(C$_1$–C$_4$)alkyl, (C$_1$–C$_4$)alkoxycarbonyl, (C$_1$–C$_7$)alkyl, (C$_2$–C$_7$)alkenyl, (C$_2$–C$_7$)alkynyl, (C$_3$–C$_7$)cycloalkyl, (C$_3$–C$_7$), cycloalkyl(C$_1$–C$_4$)alkyl, (C$_3$–C$_7$)cycloalkyl(C$_1$–C$_4$)alkanoyl, formyl, (C$_1$–C$_8$)alkanoyl, (C$_1$–C$_6$)alkanoyl (C$_1$–C$_6$)alkyl, aminocarbonylamino or mono-N-, di-N,N-, di-N,N'- or tri-N,N,N'—(C$_1$–C$_4$)alkyl substituted aminocarbonylamino, (C$_1$–C$_4$)alkanoylamino, (C$_1$–C$_4$)alkoxycarbonylamino, sulfonamido, hydroxysulfonyl, (C$_1$–C$_4$)alkylsulfonamido, amino, mono-N- or di-N,N—(C$_1$–C$_4$)alkylamino, carbamoyl, mono-N- or di-N,N—(C$_1$–C$_4$)alkylcarbamoyl, cyano, thiol, (C$_1$–C$_6$)alkylthio, (C$_1$–C$_6$)alkylsulfinyl, (C$_1$–C$_4$)alkylsulfonyl or mono-N- or di-N,N—(C$_1$–C$_4$)alkylaminosulfinyl;

R$^1$, R$^2$ and R$^3$, when containing an alkyl, alkenyl, alkylene or alkenylene moiety, are optionally straight or branched and are optionally mono-, di- or tri-substituted on carbon independently with halo or hydroxy; and V is a bond, —CO— or ($C_1$-$C_3$)alkylene optionally mono- or di-substituted independently with hydroxy or fluoro, provided that (1) when L is —CO—, A is hydroxy; and (2) when L is a bond and M is phenyl, said phenyl is substituted with one to three substituents selected from $R^1$, $R^2$ and $R^3$.

2. The method as recited in claim 1 wherein osteoporosis, osteotomy, childhood idiopathic bone loss or bone loss associated with periodontitis is treated.

3. The method as recited in claim 2 wherein osteoporosis is treated in a human.

4. The method as recited in claim 3 wherein glucocorticoid-induced osteoporosis, hyperthyroidism-induced osteoporosis, immobilization-induced osteoporosis, heparin-induced osteoporosis or immunosuppressive-induced osteoporosis is treated.

5. A method for augmenting and maintaining bone mass in a mammal comprising administering to a mammal a therapeutically effective amount of a compound of the formula $I^A$

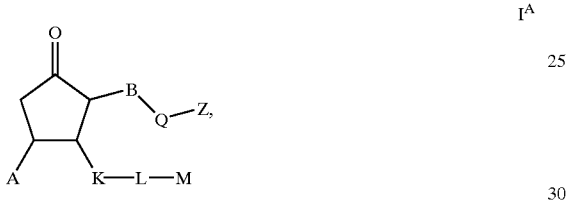

a prodrug thereof or a pharmaceutically acceptable salt of said compound or said prodrug wherein A is hydrogen or hydroxy;

B is propylene, propenylene or propynylene;

Q is propylene, —$CH_2OCH_2$—, thiazolyl, pyridyl, phenyl or thienyl;

Z is carboxyl, ($C_1$-$C_6$)alkoxycarbonyl, tetrazolyl, 1,2,4-oxadiazolyl or 5-oxo-1,2,4-oxadiazolyl;

K is ethylene or ethenylene;

L is a bond or —CO—;

M is —Ar, —$Ar^1$—V—$Ar^2$, —$Ar^1$—S—$Ar^2$ or —$Ar^1$—O—$Ar^2$ wherein

Ar, $Ar^1$ and $Ar^2$ are each independently a fully saturated, partially unsaturated or fully unsaturated five to eight membered ring optionally having one to four heteroatoms selected independently from oxygen, sulfur and nitrogen, or, a bicyclic ring consisting of two fused partially saturated, fully saturated or fully unsaturated five and/or six membered rings, taken independently, optionally having one to four heteroatoms selected independently from nitrogen, sulfur and oxygen, or, a tricyclic ring consisting of three fused partially saturated, fully saturated or fully unsaturated five and/or six membered rings, taken independently, optionally having one to four heteroatoms selected independently from nitrogen, sulfur and oxygen, any of said partially saturated or fully saturated rings optionally having one or more oxo groups substituted on carbon, said Ar, $Ar^1$ and $Ar^2$ moieties are each independently optionally substituted, on one ring if the moiety is monocyclic, on one or both rings if the moiety is bicyclic, or on one, two or three rings is the moiety is tricyclic, on carbon with up to three substituents independently selected from $R^1$, $R^2$ and $R^3$ wherein $R^1$, $R^2$ and $R^3$ are hydroxy, nitro, halo, ($C_1$-$C_7$)alkoxy, ($C_1$-$C_4$)alkoxy($C_1$-$C_4$)alkyl, ($C_1$-$C_4$)alkoxycarbonyl, ($C_1$-$C_7$)alkyl, ($C_2$-$C_7$)alkenyl, ($C_2$-$C_7$)alkyl, ($C_3$-$C_7$)cycloalkyl, ($C_3$-$C_7$)cycloalkyl($C_1$-$C_4$)alkyl, ($C_3$-$C_7$)cycloalkyl($C_1$-$C_4$)alkanoyl, formyl, ($C_1$-$C_8$)alkanoyl, ($C_1$-$C_6$)alkanoyl($C_1$-$C_6$)alkyl, aminocarbonylamino or mono-N-, di-N,N-, di-N,N,N'- or tri-N,N,N'—($C_1$-$C_4$)alkyl substituted aminocarbonylamino, ($C_1$-$C_4$)alkanoylamino, ($C_1$-$C_4$)alkoxycarbonylamino, sulfonamido, hydroxysulfonyl, ($C_1$-$C_4$)alkylsulfonamido, amino, mono-N- or di-N,N—($C_1$-$C_4$)alkylamino, carbamoyl, mono-N- or di-N,N—($C_1$-$C_4$)alkylcarbamoyl, cyano, thiol, ($C_1$-$C_6$)alkylthio, ($C_1$-$C_6$)alkylsulfinyl, ($C_1$-$C_4$)alkylsulfonyl or mono-N- or di-N,N—($C_1$-$C_4$)alkylaminosulfinyl;

$R^1$, $R^2$ and $R^3$, when containing an alkyl, alkenyl, alkylene or alkenylene moiety, are optionally straight or branched and are optionally mono-, di- or tri-substituted on carbon independently with halo or hydroxy; and V is a bond, —CO— or ($C_1$-$C_3$)alkylene optionally mono- or di-substituted independently with hydroxy or fluoro;

provided that (1) when L is —CO—, A is hydroxy; and (2) when L is a bond and M is phenyl, said phenyl is substituted with one to three substituents selected from $R^1$, $R^2$ and $R^3$.

6. The method as recited in claim 5 wherein bone heating following facial reconstruction, maxillary reconstruction or mandibular reconstruction is treated, vertebral synostosis is induced or long bone extension is enhanced, the healing rate of a bone graft is enhanced or prosthetic ingrowth is enhanced.

7. The method as recited in claim 5 wherein a bone fracture is treated in a human.

* * * * *